(12) United States Patent
Kuppers-Munther

(10) Patent No.: US 10,913,932 B2
(45) Date of Patent: Feb. 9, 2021

(54) MATURATION OF MAMMALIAN HEPATOCYTES

(71) Applicant: Takara Bio Europe AB, Gothenburg (SE)

(72) Inventor: Barbara Kuppers-Munther, Gothenburg (SE)

(73) Assignee: TAKARA BIO EUROPE AB, Gothenburg (SE)

(*) Notice: Subject to any disclaimer, the term of this patent is extended or adjusted under 35 U.S.C. 154(b) by 257 days.

(21) Appl. No.: 15/578,899

(22) PCT Filed: Jun. 3, 2016

(86) PCT No.: PCT/EP2016/062670
§ 371 (c)(1),
(2) Date: Dec. 1, 2017

(87) PCT Pub. No.: WO2016/193441
PCT Pub. Date: Dec. 8, 2016

(65) Prior Publication Data
US 2019/0024044 A1    Jan. 24, 2019

(30) Foreign Application Priority Data

Jun. 3, 2015   (DK) .................. 2015 70345

(51) Int. Cl.
*C12N 5/071* (2010.01)

(52) U.S. Cl.
CPC .......... *C12N 5/067* (2013.01); *C12N 2500/25* (2013.01); *C12N 2500/30* (2013.01); *C12N 2500/36* (2013.01); *C12N 2500/38* (2013.01); *C12N 2501/02* (2013.01); *C12N 2501/06* (2013.01); *C12N 2501/11* (2013.01); *C12N 2501/12* (2013.01); *C12N 2501/16* (2013.01); *C12N 2501/237* (2013.01); *C12N 2501/385* (2013.01); *C12N 2501/39* (2013.01); *C12N 2501/405* (2013.01); *C12N 2501/415* (2013.01); *C12N 2501/727* (2013.01); *C12N 2501/999* (2013.01); *C12N 2506/02* (2013.01); *C12N 2506/45* (2013.01); *C12N 2533/52* (2013.01); *C12N 2533/54* (2013.01)

(58) Field of Classification Search
CPC .................................................. C12N 5/067
See application file for complete search history.

(56) References Cited

U.S. PATENT DOCUMENTS

| 8,148,151 B2 | 4/2012 | Zhao et al. | |
|---|---|---|---|
| 2005/0148073 A1* | 7/2005 | Hansen ................ | C07H 19/16 435/370 |
| 2010/0143313 A1 | 6/2010 | Yarmush et al. | |
| 2012/0021519 A1 | 1/2012 | Ichida et al. | |
| 2013/0071931 A1 | 3/2013 | Ishikawa | |

FOREIGN PATENT DOCUMENTS

| WO | WO 03/055992 | 7/2003 |
|---|---|---|
| WO | WO 2004/099394 | 11/2004 |
| WO | WO 2007/042225 | 4/2007 |
| WO | WO 2007/140968 | 12/2007 |
| WO | WO 2008/115390 | 9/2008 |
| WO | WO 2009/013254 | 1/2009 |
| WO | WO 2011/116930 | 9/2011 |
| WO | WO 2012/036344 | 3/2012 |
| WO | 2013/018851 A1 | 2/2013 |
| WO | 2014/083133 A1 | 6/2014 |
| WO | WO 2014/083132 | 6/2014 |

OTHER PUBLICATIONS

Src kinase inhibitors. Catalogue [online]. Torcis Bioscience, 2019 [retrieved on Nov. 13, 2019]. Retrieved from the Internet: <URL: https://www.tocris.com/pharmacology/src-kinases/inhibitors>. (Year: 2019).*
Woodcroft et al., Insulin Signaling in the transcriptional and post-transcriptional regulation of CYP2E1 expression, Herpetology, vol. 35, No. 2 (2002) pp. 263-273. (Year: 2002).*
Guo et al., Endothelial cell-derived matrix promotes the metabolic functional maturation of hepatocyte via integrin-SRC signaling. Journal of Cellular and Molecular Medicine, vol. 21, No. 11 (Nov. 2017) pp. 2809-2822. (Year: 2017).*
Asplund et al., *One Standardized Differentiation Procedure Robustly Generates Homogenous Hepatocyte Cultures Displaying Metabolic Diversity from a Large Panel of Human Pluripotent Stem Cells*, 12 Stem Cell Rev and Rep 90-104 (2016).
Behbahan et al., *New Approaches in the Differentiation of Human Embryonic Stem Cells and Induced Pluripotent Stem Cells toward Hepatocytes*, 7 Stem Cell Rev and Rep 748-759 (2011).
Brolén et al., *Hepatocyte-like cells derived from human embryonic stem cells specifically via definitive endoderm and a progenitor stage*, 145 Journal of Biotechnology 284-294 (2010).

(Continued)

*Primary Examiner* — Kara D Johnson

(74) *Attorney, Agent, or Firm* — Buchanan Ingersoll & Rooney P.C.

(57) ABSTRACT

The present invention relates to directed differentiation and maturation of mammalian hepatocytes, such as human hepatocytes. The hepatocyte obtained in accordance with the present invention show a phenotype which is more similar to that of primary hepatocytes than previously shown. In particular, the present invention relates to exposure of mammalian hepatocytes, such as human hepatocytes, to at least one maturation factor selected from the group consisting of Src kinase inhibitors, vitamin D including precursors, metabolites and analogs thereof, hypoxia inducing compounds, sphingosine and sphingosine derivatives, activators of peroxisome proliferator-activated receptors (PPARs), platelet-activating factor (PAF), PKC inhibitors, and combinations thereof.

21 Claims, 52 Drawing Sheets

Specification includes a Sequence Listing.

(56) References Cited

OTHER PUBLICATIONS

Chen et al., *Rapid Generation of Mature Hepatocyte-Like Cells from Human Induced Pluripotent Stem Cells by an Efficient Three-Step Protocol*, 55(4) Hepatology 1193-1203 (Apr. 2012).

Chung et al., *Human Embryonic Stem Cell Lines Generated without Embryo Destruction*, 2 Cell Stem Cell 113-117 (Feb. 2008).

D'Amour et al., *Efficient differentiation of human embryonic stem cell to definitive endoderm*, 23(12) Nature Biotechnology 1534-1541 (Dec. 2005).

Duan et al., *Differentiation and Characterization of Metabolically Functioning Hepatocytes from Human Embryonic Stem Cells*, 28 Stem Cells 674-686 (2010).

Dunn et al., *Long-Term in Vitro Function of Adult Hepatocytes in a Collagen Sandwich Configuration*, 7 Biotechnol. Prog. 237-245 (1991).

Funakoshi et al., *Comparison of Hepatic-like Cell Production from Human Embryonic Stem Cells and Adult Liver Progenitor Cells: CAR Transduction Activates a Battery of Detoxification Genes*, 7 Stem Cell Rev and Rep 518-531 (2011).

Ghosheh et al., *Highly Synchronized Expression of Lineage-Specific Genes during In Vitro Hepatic Differentiation of Human Pluripotent Stem Cell Lines*, 2016 Stem Cells International 1-22 (2016).

Hay et al., *Direct Differentiation of Human Embryonic Stem Cells to Hepatocyte-like Cells Exhibiting Functional Activities*, 9(1) Cloning and Stem Cells 51-62 (2007).

Hay et al., *Efficient Differentiation of Hepatocytes from Human Embryonic Stem Cells Exhibiting Markers Recapitulating Liver Development In Vivo*, 26 Stem Cells 894-902 (2008).

Heins et al., *Derivation, Characterization, and Differentiation of Human Embryonic Stem Cells*, 22 Stem Cells 367-376 (2004).

Klimanskaya et al., *Human embryonic stem cell lines derived from single blastomeres*, 444(23) Nature Letters 481-485 (Nov. 2006).

Martin et al., *Human embryonic stem cells express an immunogenic nonhuman sialic acid*, 11(2) Nature Medicine 228-232 (Feb. 2005).

Mercader et al., *Human Embryo Culture*, Chapter 16 Essential Stem Cell Methods 341-357 (2009).

Page et al., *Gene Expression Profiling of Extracellular Matrix as an Effector of Human Hepatocyte Phenotype in Primary Cell Culture*, 97(2) ToxIcoL Sci. 384-397 (2007).

Siller et al., *Small-Molecule-Driven Hepatocyte Differentiation of Human Pluripotent Stem Cells*, 4 Stem Cell Reports 939-952 (May 12, 2015).

Si-Tayeb et al., *Highly Efficient Generation of Human Hepatocyte-like Cells from Induced Pluripotent Stem Cells*, 51(1) Hepatology 297-305 (Jan. 2010).

Song et al., *Efficient generation of hepatocyte-like cells from human induced pluripotent stem cells*, 19(11) Cell Research 1233-1242 (Nov. 2009).

Sullivan et al., *Generation of Functional Human Hepatic Endoderm from Human iPS cells*, 51(1) Hepatology 329-335 (Jan. 2010).

Takahashi et al., *Induction of Pluripotent Stem Cells from Adult Human Fibroblasts by Defined Factors*, 131 Cell 861-872 (Nov. 30, 2007).

Thomson et al., *Embryonic Stem Cell Lines Derived from Human Blastocysts*, 282 Science 1145-1147 (Nov. 6, 1998).

Turner et al., *Human Hepatic Stem Cell and Maturational Liver Lineage Biology*, 53(3) Hepatology 1035-1045 (Mar. 2011).

Vincenti et al., *v-src Activation of the Collagenase-1 (Matrix Metalloproteinase-1) Promoter through PEA3 and STAT: Requirement of Extracellular Signal-Regulated Kinases and Inhibition by Retinoic Acid Receptors*, 21 Molecular Carcinogenesis 194-204 (1998).

Wang et al., *Lineage Restriction of Human Hepatic Stem Cells to Mature Fates Is Made Efficient by Tissue-Specific Biomatrix Scaffolds*, 53(1) Hepatology 293-305 (2011).

Yu et al., *Induced Pluripotent Stem Cell Derivation*, Chapter 37 Essentials of Stem Cell Biology 331-337 (2009).

Zhou et al. *Generation of Induced Pluripotent Stem Cells Using Recombinant Proteins*, 4 Cell Stem Cell 381-384 (May 8, 2009).

Yao et al., *Quercetin protects human hepatocytes from ethanol-derived oxidative stress by inducing heme oxygenase-1 via the MAPK/Nrf2 pathways*, 47 Journal of Hepatology 253-261 (2007).

European Office Action dated Feb. 21, 2019, in corresponding European Patent Application No. 16728660.8.

Woodcroft et al., *Insulin Signaling in the Transcriptional and Posttranscriptional Regulation of CP2E1 Expression*, 35(2) Herpetology 263-273 (2002).

JP Office Action issued in corresponding JP Patent Application No. 2017-558431 dated Mar. 3, 2020 (with translation).

Office Action (Notification of Reason for Refusal) dated Sep. 2, 2020, by the Japanese Patent Office in corresponding Japanese Patent Application No. 2017-558431, and an English Translation of the Office Action. (13 pages).

Cayman Chemical, Product Information, PP1 (Src Inhibitor), May 1, 2014, 2 pages.

Okano et al."Mechanism of cell detachment from temperature-modulated, hydrophilichydrophobic polymer surfaces", Biomaterials, Elsevier, Amsterdam, vol. 16., No. 4, Jan. 1, 1995.

Jeon et al."Rosmarinic acid inhibits chemical hypoxia-induced cytotoxicity in primary cultured rat hepatocytes", Archives of Pharmacal Research, vol. 37, No. 7, 2 Oct. 2013.

Lodola et al. "Effects of Cobalt Chloride on Haem Synthesis in Isolated Hepatocytes", Febs Letters, Elsevier, Amsterdam, vol. 123, No. 1, Jan. 12, 1981.

Anavi et al."Oxidative stress impairs HIF1alpha-activation: a novel mechanisIn for increased vulnerability of steatotic hepatocytes to hypoxic stress" Free Radical Biology and Medicine Elsevier, Inc. vol. 52, No. 9, Feb. 7, 2012.

Regueira et al."HHypoxia inducible factor-1 alpha induction by tumour necrosis factor-alpha., but not by toll-like receptor agonists, modulates cellular respiration in cultured human hepatocytes" Liver International, vol. 29 No. 10, Nov. 1, 2009.

Zhi et al."PPhysiological Hypoxia Enhances Sternness Preservation,Proliferation, and Bidifferentiation of Induced Hepatic Stem CeUs" Oxidative Medicine and Cellular Longevity, vol. 2018, Jan. 1, 2018.

Ghosheh et al."Human Pluripotent Stem Cell-Derived Hepatocytes Show Higher Transcriptional Correlation with Adult Liver Tissue than with Fetal Liver Tissue", ACS Omega, vol. 5, No. 10, Mar. 2, 2020.

Extended European Search Report dated Oct. 2, 2020, issued by the European Patent Office in corresponding European Application No. 20188657.9-1118, (12 pages).

\* cited by examiner

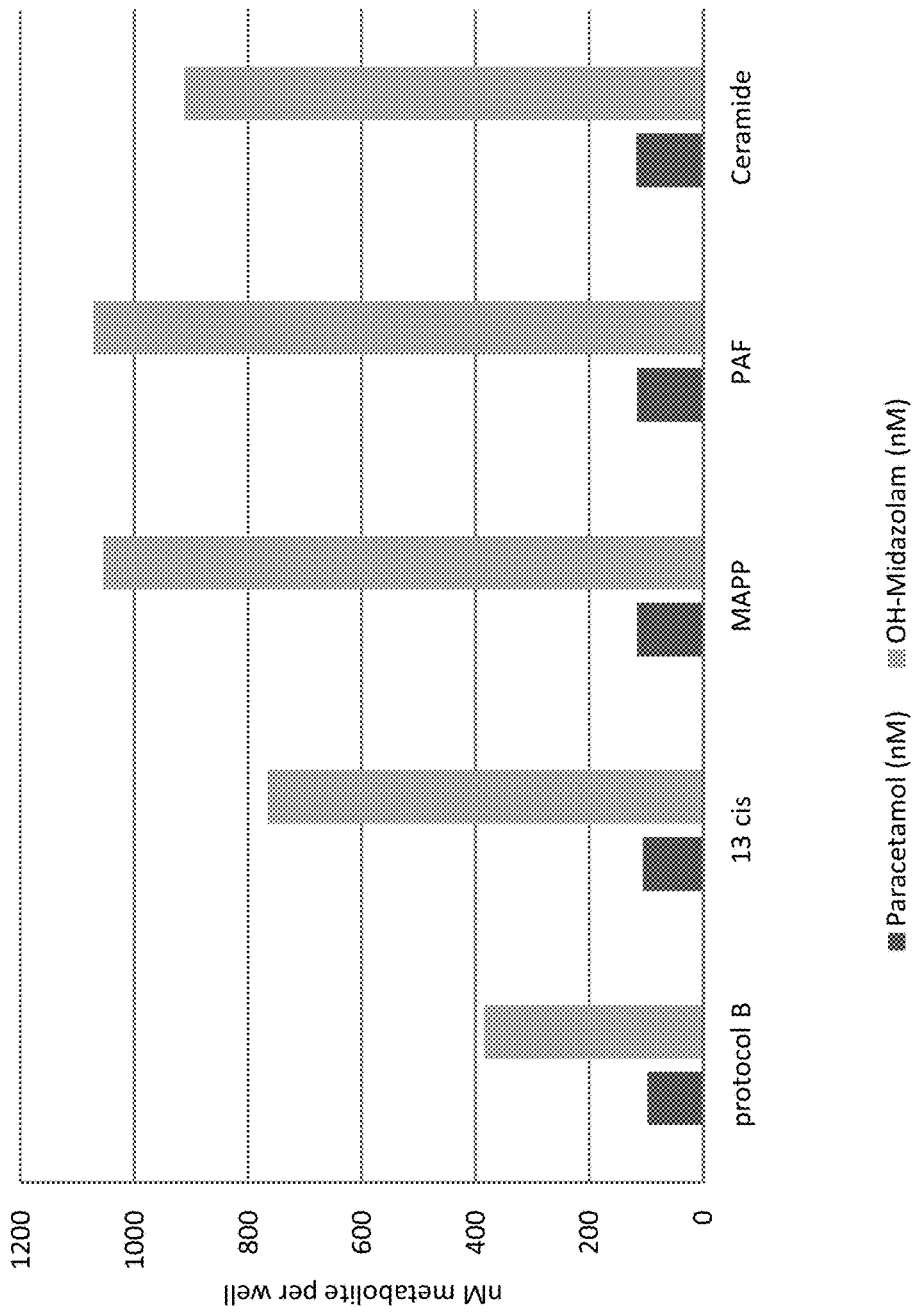

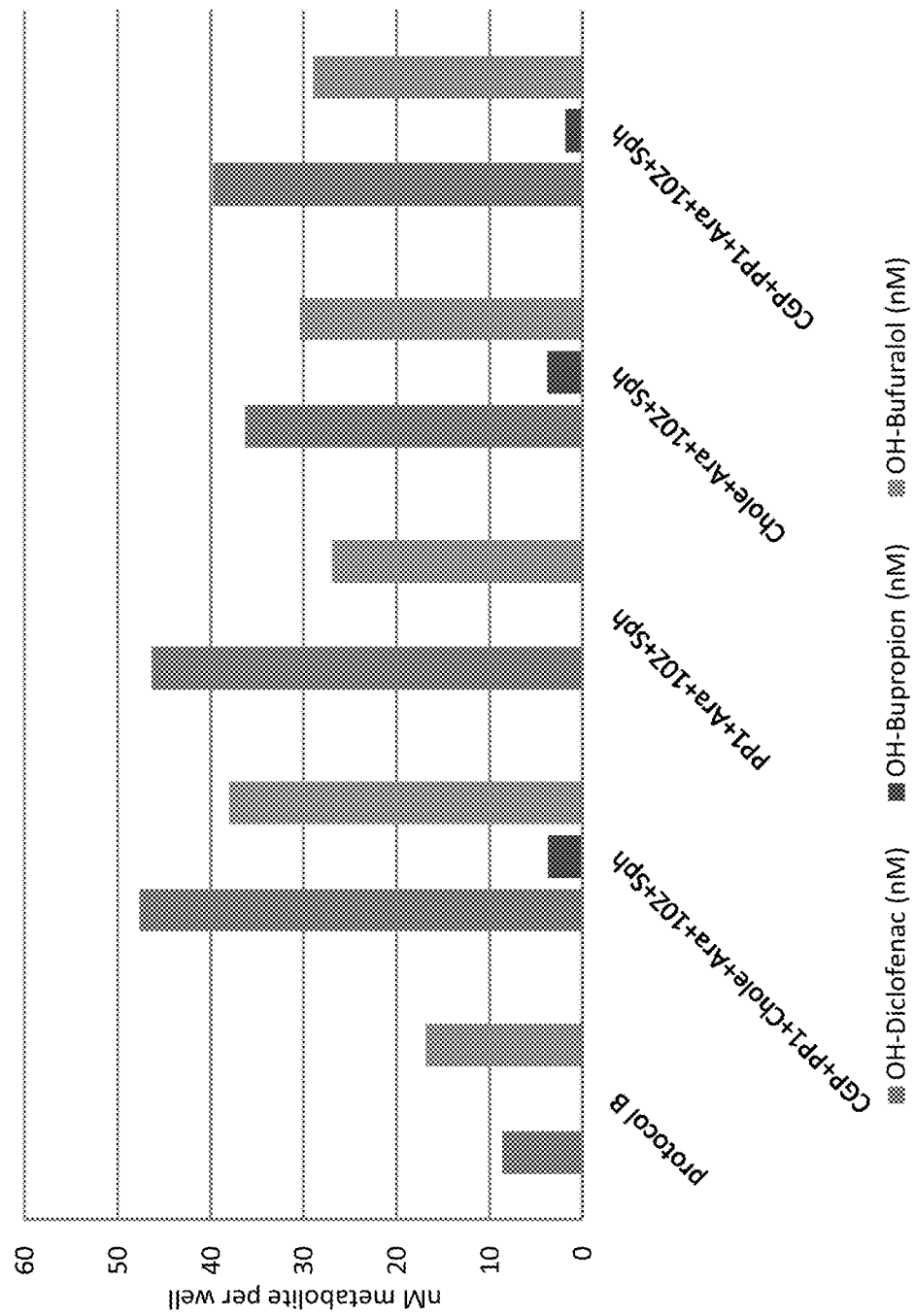

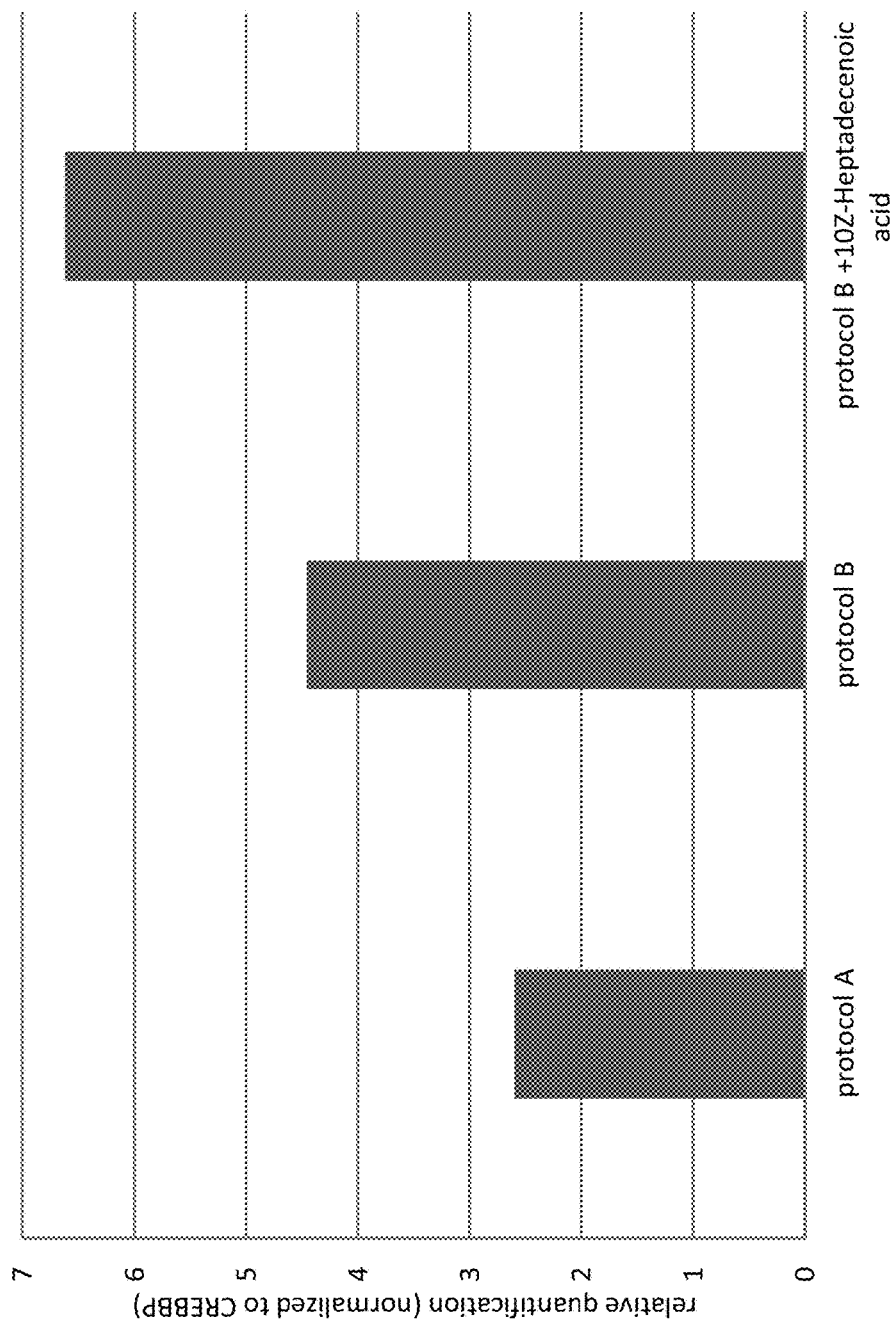

B) CYP activities in hepatocytes on day 36 with or without treatment with CGP 52608, PP1, Cholecalciferol, Arachidonic acid, 10Z-Heptadecenoic acid, Sphingosine, and Calcitriol starting on different time points of the differentiation protocol.

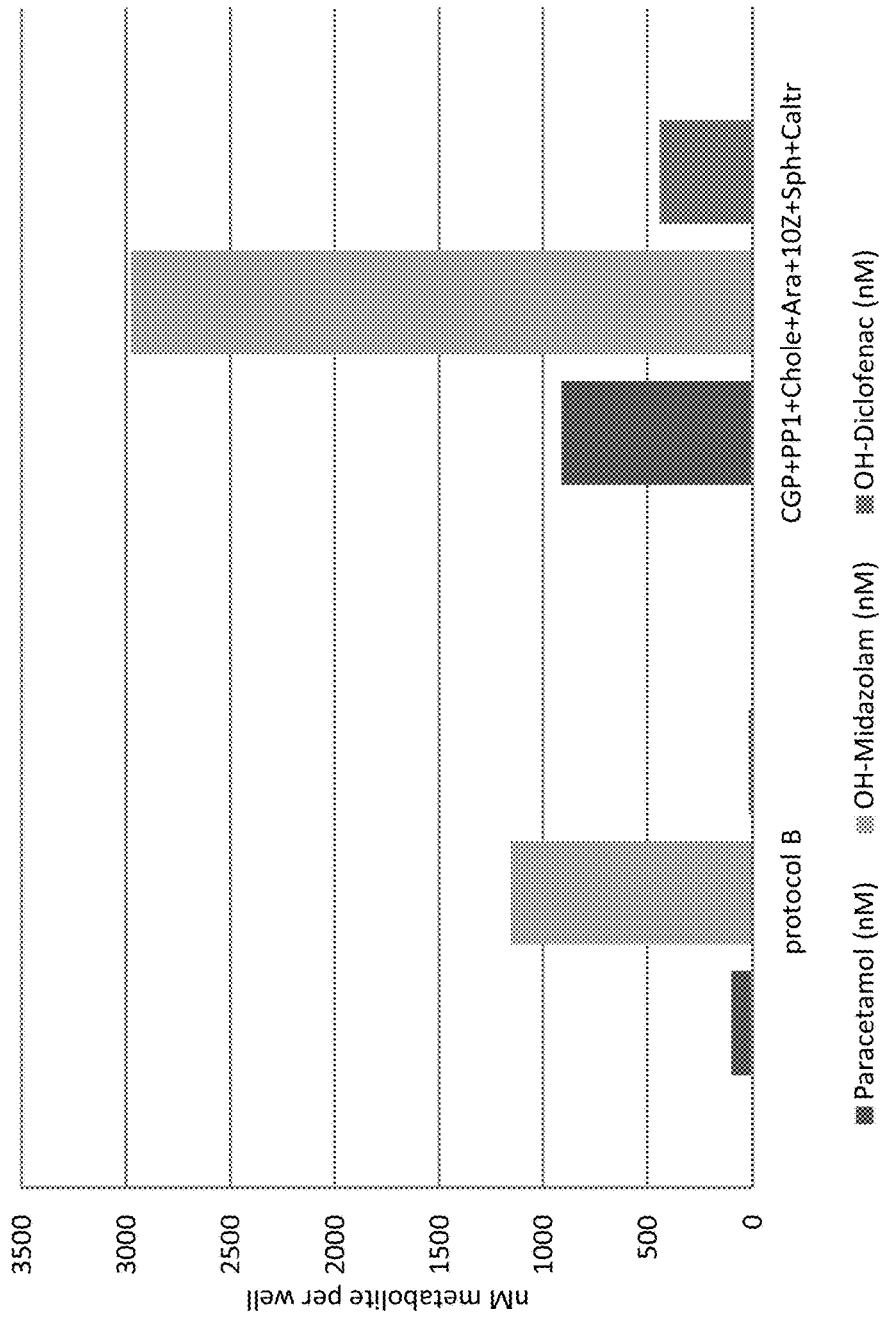

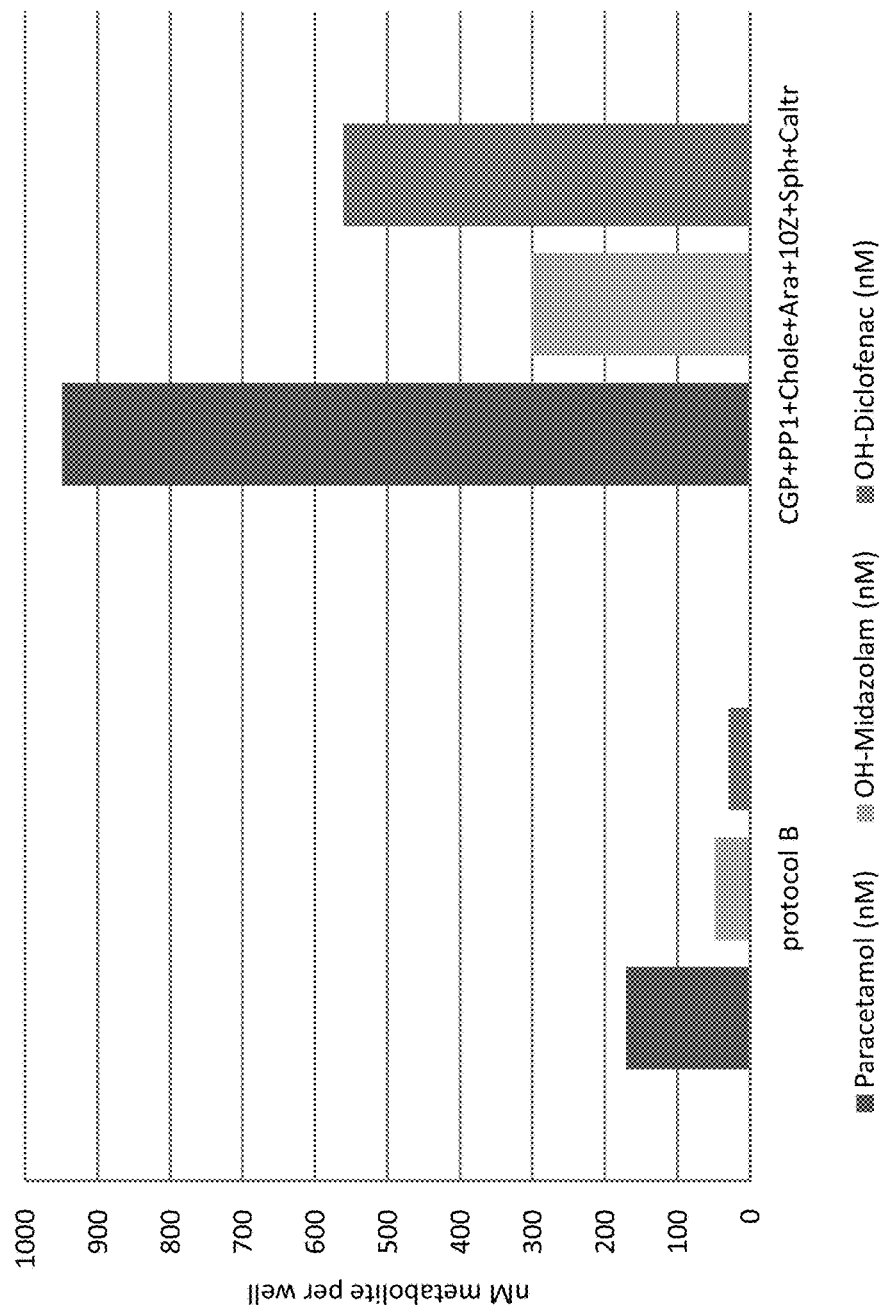

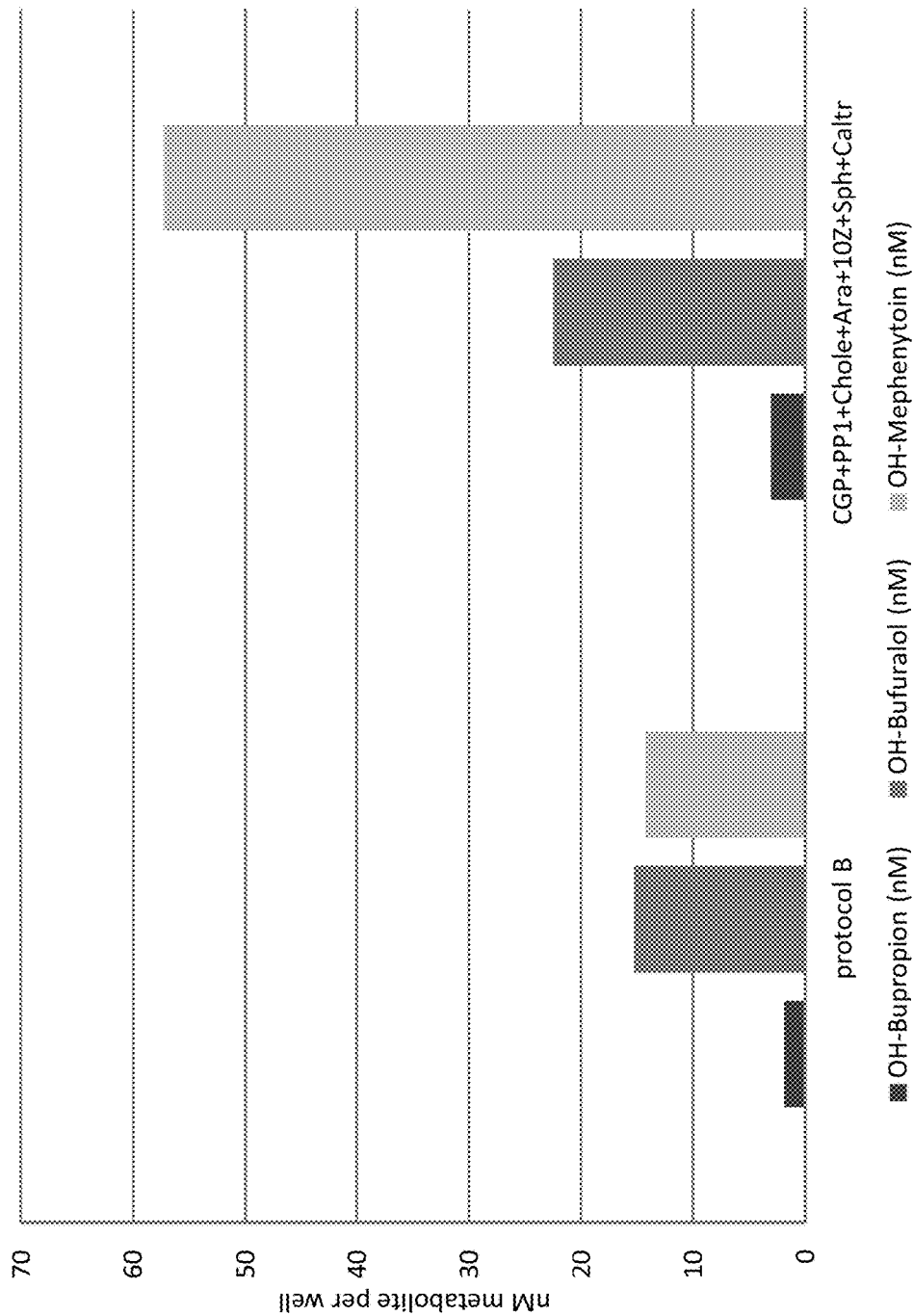

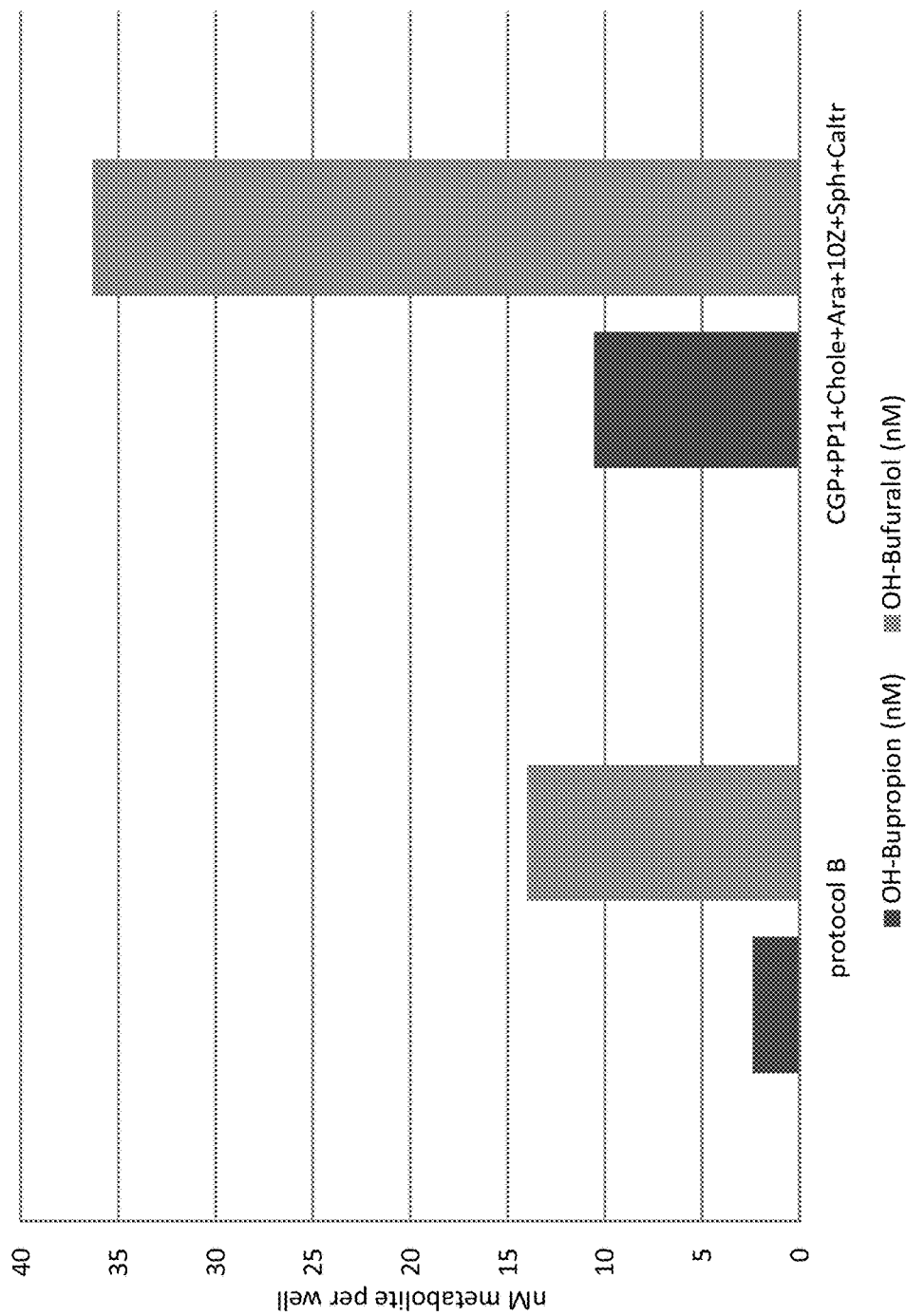

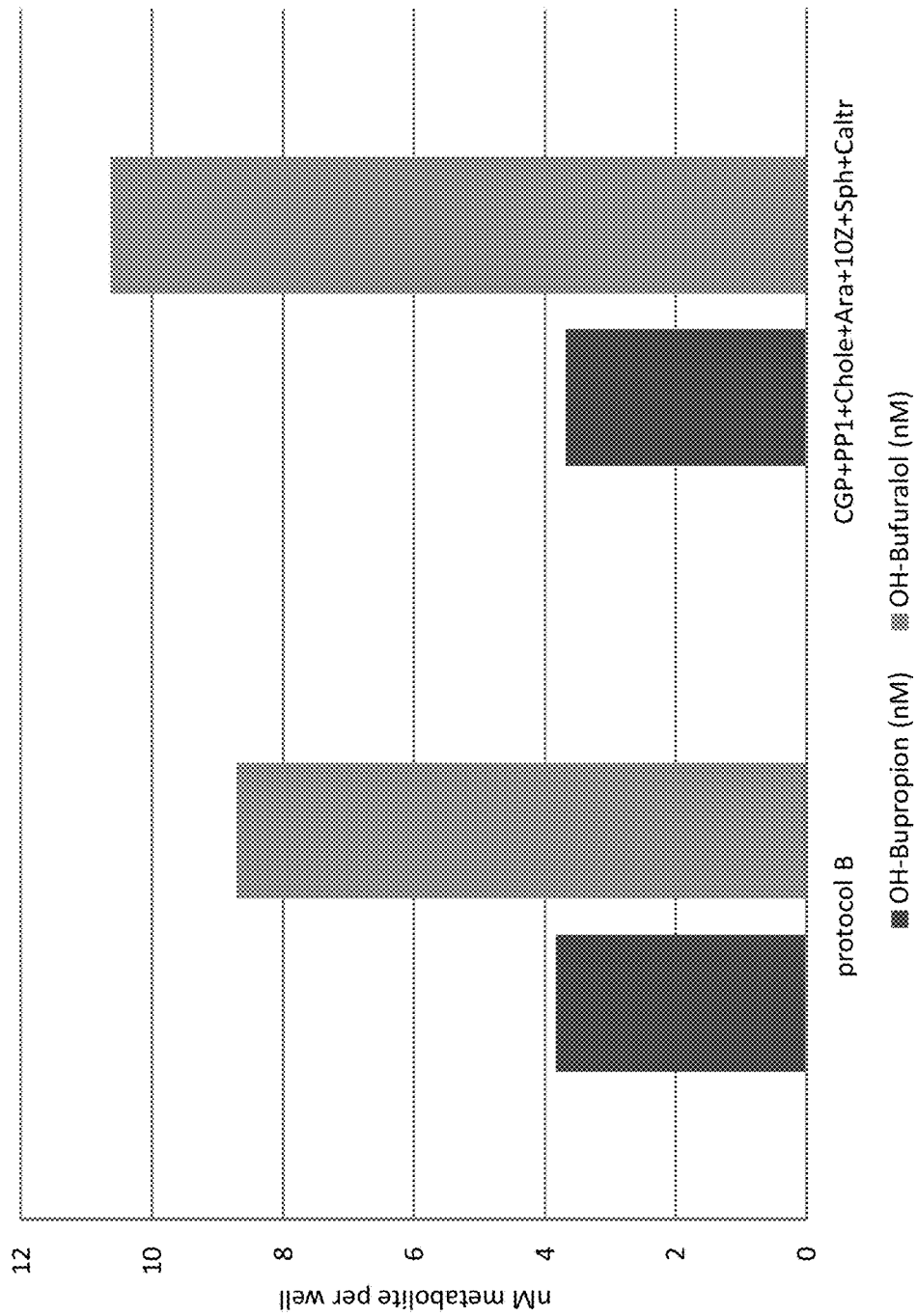

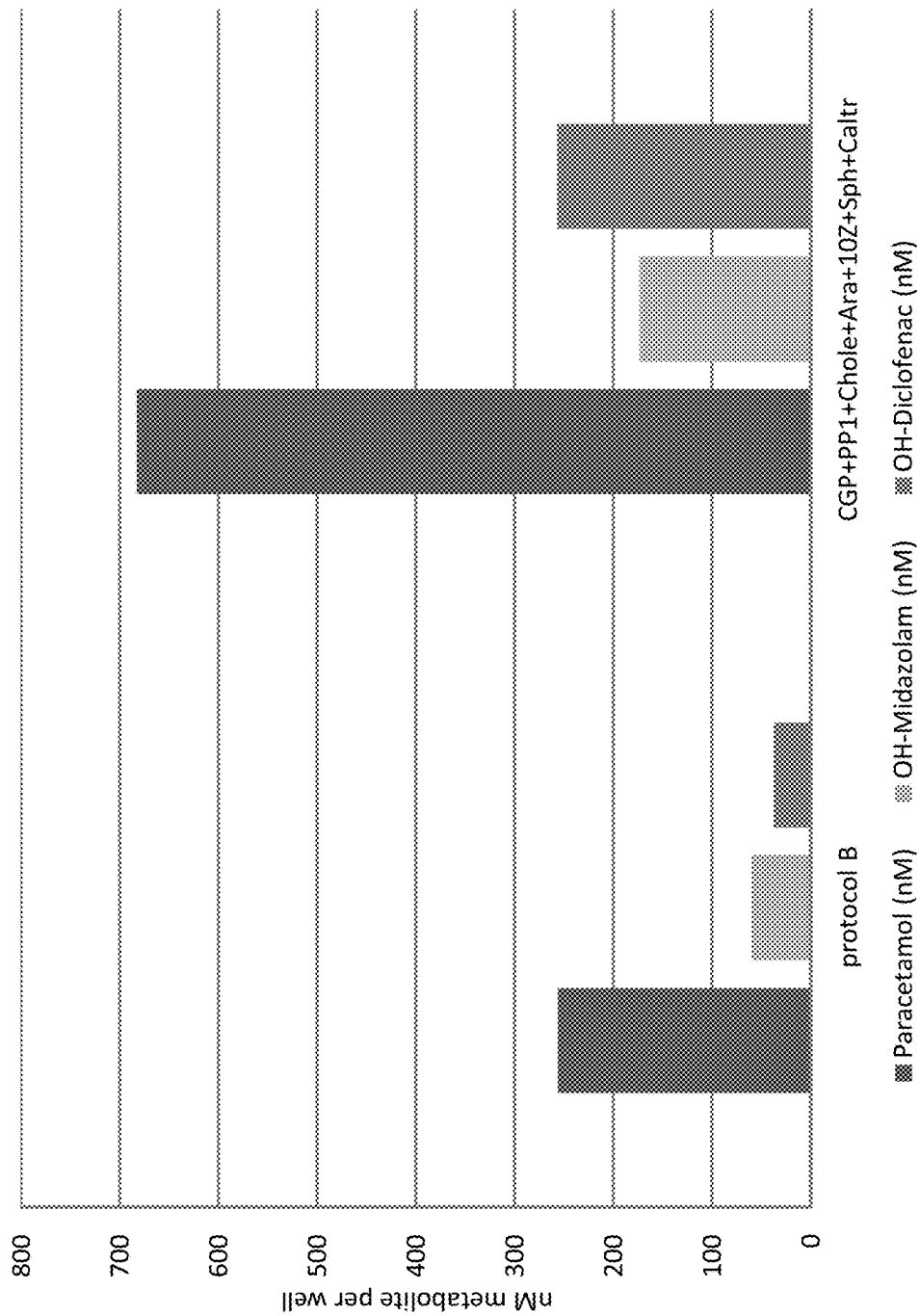

SEQUENCE LISTING

```
<160> NUMBER OF SEQ ID NOS: 1

<210> SEQ ID NO 1
<211> LENGTH: 5
<212> TYPE: PRT
<213> ORGANISM: Artificial Sequence
<220> FEATURE:
<223> OTHER INFORMATION: N-Acetyl-O-phosphono-Tyr-Glu-Glu-Ile-Glu
<220> FEATURE:
<221> NAME/KEY: MISC_FEATURE
<222> LOCATION: (1)..(1)
<223> OTHER INFORMATION: N-Acetyl-O-phosphono-

<400> SEQUENCE: 1

Tyr Glu Glu Ile Glu
1               5
```

MATURATION OF MAMMALIAN HEPATOCYTES

CROSS-REFERENCE TO RELATED APPLICATIONS

This application is a U.S. National Phase Application pursuant to 35 U.S.C. § 371 of International Patent Application No. PCT/EP2016/062670, filed on Jun. 3, 2016, and published as WO 2016/193441 on Dec. 8, 2016, which claims the benefit of Denmark Patent Application No. PA201570345, filed on Jun. 3, 2015, the entireties of which are incorporated herein by reference for all purposes.

TECHNICAL FIELD

The present invention relates to directed differentiation and maturation of mammalian hepatocytes, such as human hepatocytes. The hepatocyte obtained in accordance with the present invention show a phenotype which is more similar to that of primary hepatocytes than previously shown for stem cell derived hepatocytes. In particular, the present invention relates to exposure of mammalian hepatocytes, such as human hepatocytes, to at least one maturation factor selected from the group consisting of Src kinase inhibitors, vitamin D including precursors, metabolites and analogs thereof, hypoxia inducing compounds, sphingosine and sphingosine derivatives, activators of peroxisome proliferator-activated receptors (PPARs), platelet-activating factor (PAF), PKC inhibitors, and combinations thereof. The inventors have, as disclosed herein, found that exposing mammalian hepatocytes, such as human hepatocytes, to at least one maturation factor as disclosed herein leads to the development of more mature and functional features for the hepatocytes, compared to currently available state of the art methods.

BACKGROUND OF THE INVENTION

The development of novel pharmaceuticals faces a number of challenges, not least the problem of overcoming adverse toxicological effects. Indeed, adverse liver reactions remain the most prominent side effect. Metabolism and ultimate clearance of the majority of small molecule drugs occurs in the liver, and thus one of the main areas of focus in drug development concerns whether such compounds or their metabolites possess any hepatotoxic effect. Moreover, it is also of paramount importance to discover whether the secondary metabolites of such compounds also display any cytotoxic effects before the drug can begin clinical trial programmes.

Accordingly there is an urgent need for a hepatic model system that mimics mammalian liver cells, and especially human liver cells, and that is able to predict effects of candidate molecules in the development of new drugs or chemicals. Traditionally, researchers have been forced to rely on primary liver-derived hepatocytes for such screening but these have a number of serious drawbacks including difficulty of maintaining the cells in long term culture and difficulty of obtaining consistent, homogeneous cell populations. A solution to this has been offered in the form of hepatocytes derived from human pluripotent stem cells. Human pluripotent stem cells (hPS) have already begun to revolutionise the ways in which relevant human cell types can be obtained. The possibility to indefinitely propagate pluripotent human embryonic-derived stem (hES) cells and human induced pluripotent stem (hiPS) cells and subsequently differentiate them into the desired target cell types is now providing a stable and virtually unlimited supply of cells for a range of applications in vivo and in vitro.

Unfortunately, currently available hepatocyte cell types do not always accurately model the hepatic environment, due to differences in morphology and function. For example, one often used alternative to primary cells are hepatic cell lines which often contain very low levels of (or totally lack) metabolising enzymes and have expression of other important proteins substantially different from the native hepatocyte in vivo. This is of particular relevance in relation to drug metabolism since one of the major deficiencies in hepatic cell lines is the absence or abnormally high expression of drug transporter proteins which are essential for drug screening purposes. Other available hepatic cell lines suffer from having a morphology and physiology which is more reminiscent of fetal or juvenile hepatocytes than the more clinically relevant adult hepatocytes. For these reasons there is a strong need to develop hepatocyte cell lines which are not only easy to culture and propagate but which also possess a more mature phenotype and which behave in a manner more akin to adult primary hepatocytes.

Derivation of hepatocytes from pluripotent stem cells is well established in the art. For in vitro purposes, several groups have developed protocols for deriving hepatocytes from hES cells (Hay et al., 2007; Hay et al., 2008; Brolen et al. 2010; Funakoshi et al. 2011) as well from hiPS cells (U.S. Pat. No. 8,148,151B; Song et al. 2009; Sullivan et al. 2010; Si-Tayeb et al. 2010; Chen et al. 2012). However, common to all of these is a specific low mRNA and protein expression of genes typical for mature hepatocytes, like phase I and II genes (e.g. CYP1A2, 2B6, 2C9, 2D6, 3A4), nuclear receptors (e.g. CAR and PXR), and other adult hepatic markers (e.g. Albumin). In addition, these hESC- and hiPSC-derived hepatocytes have high expression of fetal hepatic genes like α-fetoprotein (AFP) and CYP3A7, with the result that the cell types described therein have a fetal and not adult phenotype (for overview see e.g. Baxter et al. 2010). Furthermore, in most of the published studies on hESC- and hiPSC-derived hepatocytes, expression and functionality of drug transporters has not been investigated at all.

It has recently been shown that exposure of hepatocytes to an activator of a retinoic acid responsive receptor leads to the development of more mature and functional features for the hepatocytes as well as to more pure and homogenous populations of hepatocytes (WO2014/083132).

However, there remains the need for further improving the maturation of developing hepatocyte.

SUMMARY OF THE INVENTION

The above objective has been addressed by the present inventors in that maturation factors have been identified which improve the levels of mature hepatic markers such as CYP1A, CYP3A4, CYP2C9, CYP2C19, CYP2B6 and CYP2D6.

The present invention thus provides inter alia improved methods, compositions and kits by which mammalian hepatocytes, such as human hepatocytes, derived from e.g. pluripotent stem (PS) cells, may be further matured into hepatocytes possessing a phenotype more closely resembling that of ex vivo primary liver hepatocytes. More specifically, the present invention may be summarized by the following items:

1. A method for promoting the maturation of mammalian hepatocytes, such as human hepatocytes, the method comprising:

Exposing said hepatocytes to at least one maturation factor selected from the group consisting of Src kinase inhibitors, vitamin D including precursors, metabolites and analogs thereof, hypoxia inducing compounds, sphingosine and sphingosine derivatives, activators of peroxisome proliferator-activated receptors (PPARs), platelet-activating factor (PAF), PKC inhibitors, and combinations thereof.

2. The method according to item 1, comprising culturing mammalian hepatic progenitor cells under differentiation conditions to obtain said hepatocytes.

3. A method for producing mammalian hepatocytes, the method comprising:
Culturing mammalian hepatic progenitor cells under differentiation conditions to obtain hepatocytes, and
Exposing said hepatocytes to at least one maturation factor selected from the group consisting of Src kinase inhibitors, vitamin D including precursors, metabolites and analogs thereof, hypoxia inducing compounds, sphingosine and sphingosine derivatives, activators of peroxisome proliferator-activated receptors (PPARs), platelet-activating factor (PAF), PKC inhibitors, and combinations thereof.

4. The method according to item 2 or 3, further comprising initially culturing cells of the definitive endoderm (DE) under differentiation conditions to obtain said hepatic progenitor cells.

5. The method according to item 2 or 3, further comprising initially culturing mammalian pluripotent stem (PS) cells under differentiation conditions to obtain said hepatic progenitor cells.

6. The method according to item 5, wherein the initial culturing of PS cells includes culturing the mammalian PS cells under differentiation conditions to obtain cells of the definitive endoderm (DE cells) and further culturing the obtained cells under differentiation conditions to obtain said hepatic progenitor cells.

7. The method according to item 5 or 6, wherein said mammalian pluripotent stem cells are embryonic stem (ES) cells.

8. The method according to item 5 or 6, wherein said mammalian pluripotent stem cells are artificial pluripotent stem cells.

9. The method according to item 8, wherein said artificial pluripotent stem cells are induced pluripotent stem (iPS) cells.

10. The method according to any one of items 1 to 9, wherein said mammalian cells are human cells.

11. The method according to any one of items 1 to 10, wherein said mammalian hepatocytes are exposed to at least one Src kinase inhibitor.

12. The method according to item 11, wherein said mammalian hepatocytes are exposed to at least one Src kinase inhibitor selected from the group consisting of PP1, PP2, 1-NA PP1, 1-NM-PP1, Src Inhibitor-1 (Src-I1), Src Kinase Inhibitor I, Src Kinase Inhibitor II, A-419529, A-770041, AZM 475271, bosutinib, CGP77675, Damnacanthal, dasatinib, dasatinib monohydrate, ER 27319 maleate, Fingolimod (FTY720), Geldanamycin, Herbimycin A, KB SRC 4, KX2-391, KX1-004, Lavendustin A, Lavendustin C, LCK inhibitor 2, Lyn peptide inhibitor, MLR-1023, MNS, N-Acetyl-O-phosphono-Tyr-Glu Dipentylamide, N-Acetyl-O-phosphono-Tyr-Glu-Glu-Ile-Glu, NVP-BHG712, PD 166285, PD173952, PD 180970, Piceatannol, pp60 c-src, quercetin, radicicol from *Dihet-erospora chlamydosporia* solid, saracatinib, SU 6656, TC-S 7003, TG 100572, WH-4-023, ZM 306416, and combinations thereof.

13. The method according to item 11 or 12, wherein said mammalian hepatocytes are exposed to PP1 or PP2.

14. The method according to any one of items 11 to 13, wherein said mammalian hepatocytes are exposed to said Src kinase inhibitor at a concentration in the range of 0.05 to 50 µM.

15. The method according to any one of items 1 to 14, wherein said mammalian hepatocytes are exposed to at least one vitamin D, vitamin D precursor, vitamin D metabolite or vitamin D analog.

16. The method according to item 15, wherein said mammalian hepatocytes are exposed to at least one vitamin D3, vitamin D3 precursor, vitamin D3 metabolite or vitamin D3 analog.

17. The method according to item 15 or 16, wherein said mammalian hepatocytes are exposed to at least one vitamin D3 selected from the group consisting of cholecalciferol, calcifediol, calcitriol, and combinations thereof.

18. The method according to any one of items 15 to 17, wherein said mammalian hepatocytes are exposed to cholecalciferol, calcitriol or a combination thereof.

19. The method according to any one of items 15 to 18, wherein said mammalian hepatocytes are exposed to said at least one vitamin D, vitamin D precursor, vitamin D metabolite or vitamin D analog at a concentration of 0.05 to 15 µM.

20. The method according to any one of items 1 to 19, wherein said mammalian hepatocytes are exposed to at least one hypoxia inducing compound.

21. The method according to any one of items 1 to 20, wherein said mammalian hepatocytes are exposed to at least one hypoxia inducing compound selected from the group consisting of retinoic acid receptor (RAR)-related orphan receptor alpha (ROR-alpha) ligands, $CoCl_2$, and $NaN_3$.

22. The method according to item 21, wherein said mammalian hepatocytes are exposed to at least one RAR-related orphan receptor alpha (ROR-alpha) ligand.

23. The method according to item 21 or 22, wherein said mammalian hepatocytes are exposed to at least one RAR-related orphan receptor alpha (ROR-alpha) ligand selected from the group consisting of CGP52608, a CGP52608 analog, melatonin, melatonin analogs, cholesterol, cholesterol derivatives, and combinations thereof.

24. The method according to item 22 or 23, wherein said mammalian hepatocytes are exposed to CGP52608 or a CGP52608 analog.

25. The method according to any one of items 22 to 24, wherein said mammalian hepatocytes are exposed to said RAR-related orphan receptor alpha (ROR-alpha) ligand at a concentration in the range of 0.05 to 50 µM.

26. The method according to any one of items 1 to 25, wherein said mammalian hepatocytes are exposed to at least one sphingosine or sphingosine derivative.

27. The method according to item 26, wherein said sphingosine is D-erythro-sphingosine.

28. The method according to item 26, wherein said sphingosine derivative is sphingosine-1-phosphate.

29. The method according to item 26, wherein said sphingosine derivative is a sphingolipid.

30. The method according to item 29, wherein said sphingolipid is a ceramide or a ceramide analog.

31. The method according to any one of items 26 to 30, wherein said mammalian hepatocytes are exposed to a D-erythro-ceramide or an analog thereof.
32. The method according to item 31, wherein said D-erythro-ceramide is N-palmitoyl-D-erythro-sphingosine.
33. The method according to item 30, wherein said ceramide analogue is L-erythro MAPP or D-erythro MAPP.
34. The method according to any one of items 26 to 33, wherein said mammalian hepatocytes are exposed to said sphingosine or sphingosine derivative at a concentration of 0.05 to 15 µM.
35. The method according to any one of items 1 to 34, wherein said mammalian hepatocytes are exposed to at least one activator of peroxisome proliferator-activated receptors (PPARs).
36. The method according to item 35, wherein said mammalian hepatocytes are exposed to at least one activator of peroxisome proliferator-activated receptors (PPARs) selected from the group consisting of thiazolidinediones, free fatty acids (FFAs), eicosanoids including eicosanoid precursors and eicosanoid analog, and combinations thereof.
37. The method according to item 35 or 36, wherein said mammalian hepatocytes are exposed to at least one thiazolidinedione.
38. The method according to item 37, wherein said mammalian hepatocytes are exposed to at least one thiazolidinedione selected from the group consisting of CGP52608, CGP52608 analogs, ciglitazone, rosiglitazone, pioglitazone, lobeglitazone, troglitazone, TS5444, and combinations thereof.
39. The method according to any one of items 35 to 38, wherein said mammalian hepatocytes are exposed to at least one free fatty acid.
40. The method according to item 39, wherein said at least one free fatty acid is a saturated fatty acid selected from the group consisting of dodecanoic acid, tridecanoic acid, tetradecanoic acid, pentadecanoic acid, hexadecanoic acid, heptadecanoic acid, eicosanoic acid, heneicosanoic acid, docosanoic acid, tricosanoic acid, tetracosanoic acid, pentacosanoic acid, hexacosanoic acid, and combinations thereof.
41. The method according to item 39 or 40, wherein said mammalian hepatocytes are exposed to tetradecanoic acid.
42. The method according to item 39, wherein said at least one free fatty acid is an unsaturated fatty acid selected from the group consisting of 10Z-heptadecenoic acid, arachidonic acid (AA), 9(Z),11(E)-Conjugated Linoleic Acid, eicosadienoic acid, eicosatrienoic acid (ETE), eicosapentaenoic acid (EPA), docosapentaenoic acid (DPA), docosahexaenoic acid (DHA), linoleic acid, gamma-linolenic acid, dihomo-gamma-linolenic acid, docosadiennoic acid, adrenic acid, mead acid, ricinoleic acid, docosatrienoic acid, and combinations thereof.
43. The method according to any one of items 39 to 42, wherein said mammalian hepatocytes are exposed to 10Z-heptadecenoic acid.
44. The method according to any one of items 39 to 43, wherein said mammalian hepatocytes are exposed to arachidonic acid (AA).
45. The method according to any one of items 39 to 44, wherein said mammalian hepatocytes are exposed to Docosahexaenoic acid (DHA).
46. The method according to any one of items 1 to 45, wherein said mammalian hepatocytes are exposed to at least one eicosanoid, eicosanoid precursor or eicosanoid analog.
47. The method according to item 46, wherein said mammalian hepatocytes are exposed to at least one eicosanoid, eicosanoid precursor or eicosanoid analog selected from the group consisting of Diacylglycerol, Eicosapentaenoic acid, Dihomo-gamma-linolenic acid, Arachidonic acid, ETYA (5,8,11,14-eicosatetraynoic acid), members of the hydroxyeicosatetraenoic acid (HETE) family, including 5-HETE and 15-HETE, members of the hydroxyoctadecadieonic acid (HODE) family, including 9-HODE and 13-HODE, classic eicosanoids, and non-classic eicosanoids.
48. The method according to item 46 or 47, wherein said mammalian hepatocytes are exposed to at least one classic eicosanoid selected from the group consisting of prostaglandins, prostacyclines, leukotriens, eoxins, thromboxanes, and analogs thereof.
49. The method according to item 48, wherein said prostaglandins are selected from the group consisting of $pgd_2$, $pgd_3$, $pge_1$, $pge_2$, $pge_3$, $pgf_{1c}$, $pgf_{2a}$, $pgf_3$, and $pgj_2$.
50. The method according to item 48, wherein said prostacyclins are selected from the group consisting of $pgi_2$ and $pgi_3$.
51. The method according to item 48, wherein said leukotriens are selected from the group consisting of $Lta_4$, $Lta_5$, $Ltb_4$, $Ltb_5$, $Ltc_4$, $Ltc_5$, $Ltd_4$, $Ltd_5$, $Lte_4$, and $Lte_5$.
52. The method according to item 48, wherein said eoxins are selected from the group consisting of 14,15-leukotriene A4, 14,15-leukotriene C4, 14,15-leukotriene D4, and 14,15-leukotriene E4.
53. The method according to item 48, wherein said thromboxanes are selected from the group consisting of $Txa_1$, $Txa_2$, and $Txa_3$.
54. The method according to any one of items 46 to 53, wherein said mammalian hepatocytes are exposed to at least one nonclassic eicosanoid selected from the group consisting of endocannabinoids, hepoxilins, resolvins, isofurans, isoprastanes, lipoxins, epi-lipoxins, epoxyeicosatrieonic acids (EETs).
55. The method according to item 54, wherein said endocannabionoids are selected from the group consisting of anandamides, WIN55, 212-2, palmitylethanolamide, mead ethanolamid, R-mathandamide, BML-190, N-arachidonylglycine, and arachidonamide.
56. The method according to any one of items 35 to 55, wherein said mammalian hepatocytes are exposed to said activator of peroxisome proliferator-activated receptors (PPARs) at a concentration of 0.05 to 15 µM.
57. The method according to any one of items 1 to 56, wherein said mammalian hepatocytes are exposed to at least one platelet-activating factor (PAF).
58. The method according to item 57, wherein said mammalian hepatocytes are exposed to said platelet-activating factor at a concentration of 0.05 to 50 µM.
59. The method according to any one of items 1 to 58, wherein said mammalian hepatocytes are exposed to at least one protein kinase C (PKC) inhibitor.
60. The method according to item 60, wherein said mammalian hepatocytes are exposed to said PKC inhibitor at a concentration of 0.05 to 50 µM.
61. The method according to any one of items 1 to 60, comprising the exposure of said mammalian hepatocytes to a matrix overlay.

62. The method according to item 61, wherein said matrix overlay comprises fibronectin and collagen I.
63. The method according to item 62, wherein the concentration of fibronectin is from 2 to 10 µg/cm$^2$ and the concentration of collagen I is from 30 to 150 µg/cm$^2$.
64. The method according to any one of items 2 to 63, wherein said mammalian hepatic progenitor cells are exposed to said at least one maturation factor and/or matrix overlay.
65. The method according to any one of items 1 to 64, wherein the mammalian hepatocytes obtained are for therapeutic use.
66. Use of at least one maturation factor selected from the group maturation factor selected from the group consisting of Src kinase inhibitors, vitamin D including precursors, metabolites and analog thereof, hypoxia inducing compounds, sphingosine and sphingosine derivatives, activators of peroxisome proliferator-activated receptors (PPARs), platelet-activating factor (PAF), PKC inhibitors, and combinations thereof, for maturing mammalian hepatocytes.
67. A composition comprising at least one maturation factor selected from the group Src kinase inhibitors, vitamin D including precursors, metabolites and analog thereof, hypoxia inducing compounds, sphingosine and sphingosine derivatives, activators of peroxisome proliferator-activated receptors (PPARs), platelet-activating factor (PAF), PKC inhibitors, and combinations thereof.
68. The composition according to item 67, wherein said composition comprises at least one Src kinase inhibitor.
69. The composition according to item 68, wherein said at least one Src kinase inhibitor is selected from the group consisting of PP1, PP2, 1-NA PP1, 1-NM-PP1, Src Inhibitor-1 (Src-I1), Src Kinase Inhibitor I, Src Kinase Inhibitor II, A-419529, A-770041, AZM 475271, bosutinib, CGP77675, Damnacanthal, dasatinib, dasatinib monohydrate, ER 27319 maleate, Fingolimod (FTY720), Geldanamycin, Herbimycin A, KB SRC 4, KX2-391, KX1-004, Lavendustin A, Lavendustin C, LCK inhibitor 2, Lyn peptide inhibitor, MLR-1023, MNS, N-Acetyl-O-phosphono-Tyr-Glu Dipentylamide, N-Acetyl-O-phosphono-Tyr-Glu-Glu-Ile-Glu, NVP-BHG712, PD 166285, PD173952, PD 180970, Piceatannol, pp60 c-src, quercetin, radicicol from *Diheterospora chlamydosporia* solid, saracatinib, SU 6656, TC-S 7003, TG 100572, WH-4-023, ZM 306416, and combinations thereof.
70. The composition according to item 68 or 69, wherein said at least one Src kinase inhibitor is PP1.
71. The composition according to any one of items 68 to 70, wherein the concentration of said at least one Src kinase inhibitor Is in the range of 0.05 to 50 µM.
72. The composition according to item 71, wherein the concentration of said at least one Src kinase inhibitor Is in the range of 0.1 to 10 µM, such as 2.5 to 7.5 µM.
73. The composition according to any one of items 67 to 72, wherein said composition comprises at least one vitamin D, vitamin D precursor, vitamin D metabolite or vitamin D analog.
74. The composition according to item 73, wherein said vitamin D is a vitamin D3.
75. The composition according to item 74, wherein said vitamin D3 is selected from cholecalciferol, calcifediol, calcitriol, and combinations thereof.
76. The composition according to any one of items 73 to 75, wherein the concentration of said at least one vitamin D is in the range of 0.05 to 15 µM.
77. The composition according to item 76, wherein the concentration of said at least one vitamin D is in the range of 0.1 to 10 µM, such as in the range of 0.1 to 1 µM.
78. The composition according to any one of items 67 to 77, wherein said composition comprises at least one hypoxia inducing compound.
79. The composition according to item 78, wherein said hypoxia inducing compound is at least one RAR-related orphan receptor alpha (ROR-alpha) ligand.
80. The composition according to item 79, wherein said at least one RAR-related orphan receptor alpha (ROR-alpha) ligand is selected from the group consisting of CGP52608, CGP52608 analogs, melatonin, melatonin analogs, cholesterol, cholesterol derivatives, and combinations thereof.
81. The composition according to item 79 or 80, wherein said at least one RAR-related orphan receptor alpha (ROR-alpha) ligand is CGP52608 or a CGP52608 analog.
82. The composition according to any one of items 78 to 81, wherein the concentration of said at least one hypoxia inducing compound is in the range of 0.05 to 50 µM.
83. The composition according to item 82, wherein the concentration of said at least one hypoxia inducing compound is in the range of 0.1 to 10 µM, such as in the range of 2.5 to 7.5 µM.
84. The composition according to any one of items 67 to 83, wherein said composition comprises a sphingosine or sphingosine derivative.
85. The composition according to item 84, wherein said sphingosine is D-erythro-sphingosine.
86. The composition according to item 85, wherein said sphingosine derivative is shingosine-1-phosphate.
87. The composition according to item 85, wherein said sphingosine derivative is a sphingolipid.
88. The composition according to item 87, wherein said sphingolipid is a ceramide or a ceramide analog.
89. The composition according to item 88, wherein said ceramide is N-palmitoyl-D-erythro-sphingosine.
90. The composition according to item 88, wherein said ceramide analoge is L-erythro MAPP or D-erythro MAPP.
91. The composition according to any one of items 84 to 90, wherein the concentration of said a sphingosine or sphingosine derivative is in the range of such as 0.05 to 15 µM.
92. The composition according to item 91, wherein the concentration of said a sphingosine or sphingosine derivative is in the range of 0.1 to 10 µM, such as in the range of 0.1 to 1 µM.
93. The composition according to any one of items 67 to 92, wherein said composition comprises at least one activator of peroxisome proliferator-activated receptors (PPARs).
94. The composition according to item 93, wherein said at least one activator of peroxisome proliferator-activated receptors is selected from the group consisting of thiazolidinediones, free fatty acids (FFAs), eicosanoids including eicosanoid precursors and eicosanoid analog, and combinations thereof.
95. The composition according to item 93 or 94, wherein said at least one activator of peroxisome proliferator-activated receptors is at least one unsaturated fatty acid selected from the group consisting of 10Z-heptadecenoic acid, arachidonic acid (AA), 9(Z),11(E)-Conjugated Linoleic Acid, eicosadienoic acid, eicosatrienoic acid (ETE), eicosapentaenoic acid (EPA), docosapentaenoic acid (DPA), docosahexaenoic acid (DHA), linoleic acid, gamma-linolenic acid, dihomo-gamma-linolenic acid, docosadiennoic acid, adrenic acid, mead acid, ricinoleic acid, docosatrienoic acid, and combinations thereof.

96. The composition according to any one of items 93 to 95, wherein said composition comprises 10Z-heptadecenoic acid.

97. The composition according to any one of items 93 to 96, wherein said composition comprises arachidonic acid (AA).

98. The composition according to any one of items 93 to 97, wherein said composition comprises Docosahexaenoic acid (DHA).

99. The composition according to any one of items 93 to 98, comprising 10Z-heptadecenoic acid and arachidonic acid (AA).

100. The composition according to item 93 or 94, wherein said at least one activator of peroxisome proliferator-activated receptors is at least one saturated fatty acid selected from the group consisting of dodecanoic acid, tridecanoic acid, tetradecanoic acid, pentadecanoic acid, hexadecanoic acid, heptadecanoic acid, eicosanoic acid, heneicosanoic acid, docosanoic acid, tricosanoic acid, tetracosanoic acid, pentacosanoic acid, hexacosanoic acid, and combinations thereof.

101. The composition according to any one of items 93 to 100, wherein said composition comprises tetradecanoic acid.

102. The composition according to item 93 or 94, wherein said at least one activator of peroxisome proliferator-activated receptors is at least one eicosanoid, eicosanoid precursor or eicosanoid analog.

103. The composition according to item 102, wherein said at least one activator of peroxisome proliferator-activated receptors is at least an eicosanoid, eicosanoid precursor or eicosanoid analog selected from the group consisting of Diacylglycerol, Eicosapentaenoic acid, Dihomo-gamma-linolenic acid, Arachidonic acid, ETYA (5,8,11,14-eicosatetraynoic acid), members of the hydroxyeicosatetraenoic acid (HETE) family, including 5-HETE and 15-HETE, members of the hydroxyoctadecadieonic acid (HODE) family, including 9-HODE and 13-HODE, classic eicosanoids, and non-classic eicosanoids.

104. The composition according to item 103, wherein said classic eicosanoids are selected from the group consisting of prostaglandins, prostacyclines, leukotriens, eoxins, thromboxanes, and analogs thereof.

105. The composition according to item 104, wherein said prostaglandins are selected from the group consisting of $pgd_2$, $pgd_3$, $pge_1$, $pge_2$, $pge_3$, $pgf_{1c}$, $pgf_{2a}$, $pgf_3$, and $pgj_2$.

106. The composition according to item 104, wherein said prostacyclins are selected from the group consisting of $pgi_2$ and $pgi_3$.

107. The composition according to item 104, wherein said leukotriens are selected from the group consisting of $Lta_4$, $Lta_5$, $Ltb_4$, $Ltb_5$, $Ltc_4$, $Ltc_5$, $Ltd_4$, $Ltd_5$, $Lte_4$, and $Lte_5$.

108. The composition according to item 104, wherein said eoxins are selected from the group consisting of 14,15-leukotriene A4, 14,15-leukotriene C4, 14,15-leukotriene D4, and 14,15-leukotriene E4.

109. The composition according to item 104, wherein said thromboxanes are selected from the group consisting of $Txa_1$, $Txa_2$, and $Txa_3$.

110. The composition according item 103, wherein said nonclassic eicosanoids are selected from the group consisting of endocannabinoids, hepoxilins, resolvins, isofurans, isoprastanes, lipoxins, epi-lipoxins, epoxyeicosatrieonic acids (EETs).

111. The composition according to item 110, wherein said endocannabionoids are selected from the group consisting of anandamides, WIN55, 212-2, palmitylethanolamide, mead ethanolamid, R-mathandamide, BML-190, N-arachidonylglycine, and arachidonamide.

112. The composition according to any one of items 93 to 111, wherein the concentration of said at least one activator of peroxisome proliferator-activated receptors is in the range of 0.05 to 15 µM.

113. The composition according to item 112, wherein the concentration of said at least one activator of peroxisome proliferator-activated receptors is in the range of 0.1 to 10 µM, such as in the range of 0.1 to 1 µM.

114. The composition according to any one of items 67 to 113, wherein said composition comprises at least one platelet-activating factor (PAF).

115. The composition according to item 114, wherein said at least one PAF is C16-PAF.

116. The composition according to item 114 or 115, wherein the concentration of said at least one platelet-activating factor (PAF) is in the range of 0.05 to 50 µM.

117. The composition according to item 116, wherein the concentration of said at least one platelet-activating factor (PAF) is in the range of 0.1 to 10 µM, such as in the range of 2.5 to 7.5 µM.

118. The composition according to any one of items 67 to 117, wherein said composition comprises at least one PKC inhibitor.

119. The composition according to item 118, whereins said composition comprises at least one PKC inhibitor selected from the group consisting of Bisindolylmaleimide I, Bisindolylmaleimide II, Bisindolylmaleimide III, Bisindolylmaleimide V, Bisindolylmaleimide VI, Bisindolylmaleimide VII, Bisindolylmaleimide VIII, Bisindolylmaleimide X, HBDDE, Rottlerin, Palmitoyl-DL-carnitine, R-Stearoyl Carnitine Chloride, Piceatannol, H-9, H-8, 1-(5-Isoquinolinesulfonyl)-3-methylpiperazine, HA-100 dihydrochloride, HA-1004, HA-1077, 5-Iodotubericidin, Ro-32-0432, Ro-31-7549, Enzastaurin (LY317615), Sotrastaurin, Dequalinium Chloride, Go 6976, Go 6983, Go 7874, Myricitrin, 4-Hydroxy-Tamoxifen, N-Desmethyltamoxifen HCl, Safingol, Phloretin, UCN-01, 7-Oxostaurosporine, K-252a, K-252b, K-252c, Melittin, Hispidin, Calphostin C, Ellagic acid, PKC Inhibitor Peptide 19-31, PKC Inhibitor Peptide 19-36, PKC epsilon Translocation Inhibitor II, EGF-R Fragment 651-658, PKC beta inhibitor (CAS 257879-35-9), PKC 20-28, PKCβII/EGFR Inhibitor (CAS 145915-60-2), PKCθ Pseudosubstrate Inhibitor, PKCθ/δ Inhibitor, [Ala107]-MBP (104-118), [Ala113]-MBP (104-118), ZIP, C-1, Bryostatin 1, LY 333531 hydrochloride, CGP 53353, Chelerythrine Chloride, TCS 21311, CID 755673, Gossypol, ET-18-OCH3, 1-O-Hexadecyl-2-O-methyl-rac-glycerol, NPC-15437 dihydrochloride, NGIC-I, MDL-27, 032, DAPH-7, 7-Aminoindole, 5-Amino-2-methylindole, rac-2-Methoxy-3-hexadecanamido-1-propylphosphocholine, Copper bis-3,5-diisopropylsalicylate, D,L-3,4-Dihydroxymandelic Acid, rac-3-Octadecanamido-2-Methoxypropan-1-ol Phosphocholine, KRIBB3, Ilmofosine, rac-2-Methoxy-3-hexadecanamido-1-propylphosphocholine, and combinations thereof.

120. The composition according to item 118 or 119, wherein the concentration of said at least one PKC inhibitor is in the range of 0.01 to 50 µM.

121. The composition according to item 120, wherein the concentration of said at least one PKC inhibitor is in the range of about 0.5 to about 10 µM.

122. The composition according to any one of items 67 to 121, comprising PP1, CGP52608, 10Z-heptadecenoic acid, arachidonic acid (AA), cholecalciferol, calcitriol and D-erythro-sphingosine.
123. The composition according to any one of items 67 to 122, wherein said composition comprises at least one extracellular matrix (ECM) component or ECM component mixture.
124. The composition according to item 123, wherein said at least one extracellular matrix (ECM) component or ECM component mixture is selected from collagen, such as collagen I, II, III, IV, V or VI, fibronectin, elastin, chondroitin sulfate proteoglycan, dermatan sulfate proteoglycan, heparin proteoglycan, heparan sulfate proteoglycan, such as glypicans, syndecans or perlecans, glycosaminoglycans, nidogen/entactin, laminins, biglycan, tenascin, hyaluronans, and combinations thereof.
125. The composition according to item 123 or 124, wherein the composition comprises collagen I and fibronectin.
126. The composition according to item 125, wherein the concentration of collagen I is in the range of about 2 to about 150 μg/cm$^2$ culture area.
127. The composition according to item 125 or 126, wherein the concentration of fibronectin is in the range of about 2 to about 30 μg/cm$^2$ culture area.
128. A culture medium comprising the composition according to any one of items 67 to 127.
129. A kit comprising at least one maturation factor selected from the group Src kinase inhibitors, vitamin D including precursors, metabolites and analog thereof, hypoxia inducing compounds, sphingosine and sphingosine derivatives, activators of peroxisome proliferator-activated receptors (PPARs), platelet-activating factor (PAF), PKC inhibitors, and combinations thereof.
130. The kit according to item 129, comprising the composition according to any one of items 67 to 127 or the culture medium according to item 128.
131. The kit according to item 129 or 130 comprising at least one extracellular matrix (ECM) component or ECM component mixture.

DETAILED DESCRIPTION OF THE INVENTION

The invention provides methods for maturing mammalian hepatocytes, such as human hepatocytes, by exposing the cells to at least one maturation factor selected from the group Src kinase inhibitors, vitamin D including precursors, metabolites and analog thereof, hypoxia inducing compounds, sphingosine and sphingosine derivatives, activators of peroxisome proliferator-activated receptors (PPARs), platelet-activating factor (PAF), PKC inhibitors, and combinations thereof.

The methods may further comprise culturing of mammalian hepatic progenitor cells, such as human hepatic progenitor cells, in a supportive culture and differentiation medium to obtain said hepatocytes where the cells are exposed to at least one maturation factor selected from the group Src kinase inhibitors, vitamin D including precursors, metabolites and analogs thereof, hypoxia inducing compounds, sphingosine and sphingosine derivatives, activators of peroxisome proliferator-activated receptors (PPARs), platelet-activating factor (PAF), PKC inhibitors, and combinations thereof.

The method for promoting the maturation of mammalian hepatocytes, such as human hepatocytes, may thus be described as comprising the step:

Exposing said mammalian hepatocytes, such as said human hepatocytes, to at least one maturation factor selected from the group Src kinase inhibitors, vitamin D including precursors, metabolites and analogs thereof, hypoxia inducing compounds, sphingosine and sphingosine derivatives, activators of peroxisome proliferator-activated receptors (PPARs), platelet-activating factor (PAF), PKC inhibitors, and combinations thereof.

The method for promoting the maturation of human hepatocytes may further comprise the step of culturing mammalian hepatic progenitor cells, such as human hepatic progenitor cells, under differentiation conditions to obtain said hepatocytes.

The present invention also provides a method for producing mammalian hepatocytes, such as human hepatocytes, whereby mammalian hepatic progenitor cells, such as human hepatic progenitor cells, are cultured under differentiation conditions to obtain hepatocytes, and the obtained hepatocytes are exposed to at least one maturation factor selected from the group Src kinase inhibitors, vitamin D including precursors, metabolites and analogs thereof, hypoxia inducing compounds, sphingosine and sphingosine derivatives, activators of peroxisome proliferator-activated receptors (PPARs), platelet-activating factor (PAF), PKC inhibitors, and combinations thereof.

The method for producing mammalian hepatocytes, such as human hepatocytes, may thus be described as comprising the following steps:

Culturing mammalian hepatic progenitor cells, such as human hepatic progenitor cells, under differentiation conditions to obtain hepatocytes, and Exposing said hepatocytes to at least one maturation factor selected from the group consisting of Src kinase inhibitors, vitamin D including precursors, metabolites and analogs thereof, hypoxia inducing compounds, sphingosine and sphingosine derivatives, activators of peroxisome proliferator-activated receptors (PPARs), platelet-activating factor (PAF), PKC inhibitors, and combinations thereof.

Mammalian hepatic progenitor cells, such as human hepatic progenitor cells, may thus be used as starting material according to the invention. The hepatic progenitor starting material may, for example, be an established cell line of hepatic progenitor cells, hepatic progenitor cells de novo isolated from livers, such as human livers, or may be prepared de novo, such as from mammalian pluripotent stem (PS) cells, such as human pluripotent stem (hPS) cells or mammalian definitive endoderm (DE) cells, such as human definitive endoderm (DE) cells.

The differentiation and maturation of hepatocytes cells may be divided into two phases, i.e. a first phase where the hepatic progenitor cells differentiate into hepatocytes ("hepatic progenitor phase"), and a second phase where the obtained hepatocytes further mature (maturation phase). During the maturation phase the obtained hepatocytes exhibit an increased gene and protein expression of characteristic markers for mature hepatocytes.

Suitable conditions for differentiating hepatic progenitor cells into hepatocytes from human embryonic stem (hES) cells (Hay et al., 2007; Hay et al., 2008; Brolen et al. 2010; Funakoshi et al. 2011) and from human induced pluripotent stem (hiPS) cells (U.S. Pat. No. 8,148,151B; Song et al. 2009; Sullivan et al. 2010; Si-Tayeb et al. 2010; Chen et al. 2012) are known. WO 2009/013254 A1, for example, describes suitable basic protocols to obtain hepatocytes from hepatic progenitor cells (Embodiments 1 to 4).

Generally, hepatic progenitor cells are cultured in a differentiation medium comprising one or more growth factors, such as HGF, and/or one or more differentiation inducer, such as dimethylsulfoxide (DMSO), dexamethazone (DexM), omeprazole, Oncostatin M (OSM), rifampicin, desoxyphenobarbital, ethanol or isoniazide. The concentration of the one or more growth factors, such as HGF, is usually in the range of about 10 to about 50 ng/ml, such as about 10 to about 30 ng/ml. The concentration of the one or more differentiation inducer may vary depending on the particular compound used. The concentration of DMSO, for example, is usually in the range of about 0.1 to about 1% v/v, such as about 0.25 to about 0.75% v/v. The concentration of OSM, for example, is usually in the range of about 1 to about 20 ng/ml, such as about 5 to about 15 ng/ml. The concentration of DexM, for example, is usually in the range of about 0.05 to about 1 µM, such as about 0.05 to about 0.2 µM.

The differentiation medium may further comprise an albumin source, such as FBS, FCS or BSA. The concentration of the albumin source, if present, is usually in the range of about 0.1 to about 5% v/v, such as about 0.1 to about 1%, 0.2 to 3% v/v, about 0.5 to about 2.5% v/v, about 0.5 to 1% v/v or about 1 to about 2.5% v/v.

The differentiation medium may further comprise ascorbic acid. The concentration of ascorbic acid, if present, is usually in the range of about 0.01 to about 0.1 mg/ml, such as about 0.1 to about 0.05 mg/ml.

The differentiation medium may further comprise Hydrocortisone Hemisuccinate. The concentration of Hydrocortisone Hemisuccinate, if present, is usually in the range of about 0.1 to about 1 µg/ml, such as about 0.5 to 0.8 µg/ml.

The differentiation medium may further comprise transferrin. The concentration of transferrin, if present, is usually in the range of about 1 to 20 µg/ml, such as about 5 to 15 µg/ml.

The differentiation medium may further comprise Insulin. The concentration of Insulin, if present, is usually in the range of about 1 to about 10 µg/ml, such as about 2.5 to about 7.5 µg/ml.

The differentiation medium may further comprise epidermal growth factor (EGF). The concentration of EGF, if present, is usually in the range of about 0.001 to about 0.005 µg/ml, such as about 0.0025 to about 0.0035 µg/ml.

The differentiation medium may further comprise other supplements such as PEST and/or GlutaMAX. The concentration of PEST is usually in the range of about 0.1 to about 0.5% v/v, such as about 0.1 to about 0.25% v/v. The concentration of GlutaMAX is usually in the range of about 0.5 to about 1.5% v/v, such as about 0.75 to 1.25% v/v, e.g. about 1% v/v.

The differentiation medium may further comprise at least one activator of a retinoic acid responsive receptor, i.e. a compound capable of binding to and activating a human retinoic acid receptor (RAR) and/or human retinoid X receptor (RXR), such as, e.g., a compound capable of binding to and activating both RAR and RXR. A suitable activator of a retinoic acid responsive receptor for use in the differentiation medium is retinoic acid, such as 9-cis-retinoic acid, 13-cis-retinoic acid or other retinoic acid isomers, including all-trans-retinoic acid, 7-cis retinoic acid and 11-cis-retinoic acid, or an analogue of retinoic acid, such as TTNPB, AM580, retilloic acid or CBS-211A, or a retinoid. Accordingly, 9-cis-retinoic acid may be used as the activator of a retinoic acid responsive receptor. Alternatively, or in addition, 13-cis-retinoic acid may also be used as the activator of a retinoic acid responsive receptor. The concentration of the activator of a retinoic acid responsive receptor, if present, is usually in the range of about 0.1 to about 2.5 µM, such as, e.g., in the range of about 0.1 to about 0.5 µM, such as, e.g., at about 0.2 µM.

The differentiation medium may further comprise at least one GSK-3 inhibitor and/or CDK inhibitor.

Suitable GSK-3 inhibitors for use in the invention are 9-Bromo-7,12-dihydro-indolo [3,2-d]-[1]benzazepin-6 (5H)-one, also known as Kenpaullone or NSC 664704; 1-Aza-Kenpaullone (9-Bromo-7,12-dihydro-pyrido[3',2':2,3]azepino[4,5-b]indol-6(5H)-one); Alsterpaullone (9-Nitro-7,12-dihydroindolo-[3,2-d][1]benzazepin-6(5)-one); 4-(2,6-dichlorobenzamido)-N-(piperidin-4-yl)-1H-pyrazole-3-carboxamide also known as AT-7519; N-(5-((5-tert-butyloxazol-2-yl)methylthio)thiazol-2-yl)piperidine-4-carboxamide also known as SNS-032 (BMS-387032); 4-(1-isopropyl-2-methyl-1H-imidazol-5-yl)-N-(4-(methylsulfonyl)phenyl)pyrimidin-2-amine also known as AZD5438; (2'Z,3'£)-6-Bromoindirubin-3'-oxime, also known as BIO (GSK3 Inhibitor IX); (2'Z,3'E)-6-Bromoindirubin-3'-acetoxime, also known as BIO-Acetoxime (GSK3 Inhibitor X); (5-Methyl-IH-pyrazol-3-yl)-(2-phenylquinazolin-4-yl)amine (GSK3-Inhibitor XIII); Pyridocarbazole-cyclopenadienylruthenium complex (GSK3 Inhibitor XV); TDZD-8 4-Benzyl-2-methyl-I,2,4-thiadiazolidine-3,5-dione (GSK3beta Inhibitor I); 2-Thio(3-iodobenzyl)-5-(I-pyridyl)-[I,3,4]-oxadiazole (GSK3beta Inhibitor II); OTDZT 2,4-Dibenzyl-5-oxothiadiazolidine-3-thione (GSK3beta Inhibitor III); alpha-4-Dibromoacetophenone (GSK3beta Inhibitor VII); N-(4-Methoxybenzyl)-N'-(5-nitro-I,3-thiazol-2-yl)urea, also known as AR-AO 14418 (GSK-3beta Inhibitor VIII); 3-(I-(3-Hydroxypropyl)-IH-pyrrolo[2,3-b]pyridin-3-yl]-4-pyrazin-2-yl-pyrrole-2,5-dione (GSK-3beta Inhibitor XI); TWSI 19 pyrrolopyrimidine compound (GSK3beta Inhibitor XII); L803 H-KEAP-PAPPQSpP-NH2 or its myristoylated form (GSK3beta Inhibitor XIII); 2-Chloro-I-(4,5-dibromo-thiophen-2-yl)-ethanone (GSK3beta Inhibitor VI); Aminopyrimidine CHIR99021; 3-(2,4-Dichlorophenyl)-4-(1-methyl-1H-indol-3-yl)-1H-pyrrole-2,5-dione, also known as SB216763; Indirubin-3'-monoxime; 3F8 (5-Ethyl-7,8-dimethoxy-1H-pyrrolo[3,4-c]-isoquinoline-1,3-(2H)-dione), A1070722, anorganic ions like Beryllium, Copper, Lithium, Mercury, Tungstate (Wolfram), and Zinc, AR-A 014418, AZD2858, Axin GID-25 residues (peptide), bisindolylmaleimides, CHIR98014 (CT98014), CHIR98023 (CT98023), FRATide-39 residues (peptide), Halomethylketone derivatives, e.g. HMK-32, KT5720, L803-mts (peptide) and variants, LY20900314, NP-12 (Tideglusib, NP031112), NP00111, NP031115, Polyoxygenated bis-7-azaindolyl-maleimides, RO31-8220, SB415286 (maleimide), TC-G24, TCS2002, TCS21311, TDZD-8, TOS119 and TWS119 (difluoroacetate). The GSK-3 inhibitor may, for instance, be one chosen from Kenpaullone, 1-Aza-Kenpaullone, Alsterpaullone, Aminopyrimidine CHIR99021 and Indirubin-3'-monoxime.

Suitable CDK inhibitors for use in the invention are 9-Bromo-7,12-dihydro-indolo [3,2-d]-[1]benzazepin-6 (5H)-one, also known as Kenpaullone or NSC 664704; (R)-2-(6-(benzylamino)-9-isopropyl-9H-purin-2-ylamino) butan-1-ol also known as Roscovitine; 2-(2-chlorophenyl)-5,7-dihydroxy-8-((3S,4R)-3-hydroxy-1-methylpiperidin-4-yl)-4H-chromen-4-one also known as Flavopiridol; 4-(2,6-dichlorobenzamido)-N-(piperidin-4-yl)-1H-pyrazole-3-carboxamide also known as AT-7519; 6-acetyl-8-cyclopentyl-5-methyl-2-(5-(piperazin-1-yl)pyridin-2-ylamino)pyrido[2,3-d]pyrimidin-7(8H)-one hydrochloride also known as PD 0332991 HCl; N-(5-((5-tert-butyloxazol- 2-yl)methylthio)thiazol-2-yl)piperidine-4-carboxamide also known as SNS-032 (BMS-387032); JNJ-7706621; N-(6,6-dimethyl-5-(1-methylpiperidine-4-carbonyl)-1,4,5,6-tetrahydropyrrolo[3,4-c]pyrazol-3-yl)-3-methylbutanamide also known as PHA-793887; Dinaciclib (SCH727965); (4-butoxy-1H-pyrazolo[3,4-b]pyridin-5-yl)(2,6-difluoro-4-methylphenyl)methanone also known as BMS-265246; N,1,4,4-tetramethyl-8-(4-(4-methylpiperazin-1-yl)phenylamino)-4,5-dihydro-1H-pyrazolo[4,3-h]quinazoline-3-carboxamide also known as PHA-848125; 2-(pyridin-4-yl)-6,7-dihydro-1H-pyrrolo[3,2-c]pyridin-4(5H)-one also known as PHA-767491; SCH 900776; 2-(2-chlorophenyl)-5,7-dihydroxy-8-((3S,4R)-3-hydroxy-1-methylpiperidin-4-yl)-4H-chromen-4-one hydrochloride also known as Flavopiridol HCl; (4-amino-2-(1-(methylsulfonyl)piperidin-4-ylamino)pyrimidin-5-yl)(2,3-difluoro-6-methoxyphenyl)methanone also known as R547; (2S)-1-(5-(3-methyl-1H-indazol-5-yl)pyridin-3-yloxy)-3-phenylpropan-2-amine also known as A-674563; 4-(1-isopropyl-2-methyl-1H-imidazol-5-yl)-N-(4-(methylsulfonyl)phenyl)pyrimidin-2-amine also known as AZD5438; N5-(6-aminohexyl)-N7-benzyl-3-isopropylpyrazolo[1,5-a]pyrimidine-5,7-diamine hydrochloride also known as BS-181 HCl; CY-202; AG-024322; P276-00; ZK 304709; GPC-286199; and BAY 80-3000, 2-hydroxybohemine, A674563, Aminopurvanolol, BAY1000394, BMS-265246, BS-181 Butyrolactone I, CR8 S-isomer, Diaciclib (SCH727965), JNJ-7706621, N9-isopropyl-olomoucine, NU6140, NU6102, Olomoucine II, Oxindole I, P276-00, PD332991, PHA-793887, PHA-767491, PHA-848125, PNU112455A, Purvanolol A and B, R547, (R)-DRF053 and SCH900776 (MK-8776). The GSK-3 inhibitor may, for instance, be one chosen from Kenpaullone, 1-Aza-Kenpaullone, Indirubin-3'-monoxime, Alsterpaullone, SNS-032 (BMS-387032), AT-7519 and AZD5438.

The concentration of the GSK3 inhibitor and/or CDK inhibitor, if present, is usually in the range of about 0.01 to about 10 µM. In case that, for instance, Kenpaullone is employed as the CDK inhibitor, the hepatocytes may be exposed to it at a concentration in the range of about 0.05 to about 5 µM, such as, e.g., in the range of about 0.5 to about 1.5 µM. Similar concentrations may be used in case that, for instance, 1-Aza-Kenpaullone or Alsterpaullone is used.

The culture medium forming the basis for the differentiation medium may be any culture medium suitable for culturing mammalian hepatic progenitor cells such as such as RPMI 1640 medium, RPMI 1640 advanced medium, Iscove's Modified Dulbeccos Medium (IMDM), Minimum Essential Medium (e.g., MEM, EMEM or GMEM), Dulbecco's Modified Eagle Medium (e.g., DMEM or DMEM/F-12), Ham's medium (e.g., Ham's F12 or Ham's F10), HCM medium, HBM medium, or Williams E medium. Thus, the base medium may, for example, be RPMI 1640 medium or RPMI 1640 advanced medium. Alternatively, the base medium may be Williams E medium.

The differentiation of mammalian hepatic progenitor cells, such as human hepatic progenitor cells, and further maturation of the obtained hepatocytes ("differentiation and maturation") may take up to 35 days in total. Thus, in order to obtain hepatocytes, the mammalian hepatic progenitor cells, such as human hepatic progenitor cells, are cultured in differentiation medium for up to 35 days. For example, the mammalian hepatic progenitor cells, such as human hepatic progenitor cells, may be cultured in differentiation medium for any time between about 7 to about 35 days. They may thus also be cultured for about 10 to about 30 days. They may also be cultured for about 10 to about 25 days. Alternatively, they may be cultured for about 10 to about 20 days or for about 10 to about 15 days. They may also be cultured for about 15 to about 35 days. Thus, they may also be cultured for about 15 to about 30 days. Alternatively, they may be cultured for about 15 to about 25 days. They may also be cultured for about 15 to about 20 days. During the culturing the differentiation medium is usually exchanged for fresh medium every second or third day.

Under the above described conditions, hepatocytes are obtained from hepatic progenitor cells on or after 7 days of culture. Thus, the differentiation and maturation of hepatocytes may be divided into a hepatic progenitor phase of 7 days, whereby hepatic progenitor cells differentiate into hepatocytes, and a maturation phase lasting until the end of the total culture period (e.g., until day 35), whereby the obtained hepatocytes further mature.

The at least one maturation factor employed in the methods of the invention may by any compound selected from the group consisting of Src kinase inhibitors, vitamin D including precursors, metabolites and analogs thereof, hypoxia inducing compounds, sphingosine and sphingosine derivatives, activators of peroxisome proliferator-activated receptors (PPARs), platelet-activating factor (PAF), PKC inhibitors, and combinations thereof.

Thus, the at least one maturation factor employed in the methods of the invention may be at least one Src kinase inhibitor, such as at least one (such as at least two) Src kinase inhibitor(s) selected from the group consisting of PP1 (1-(1,1-Dimethylethyl)-1-(4-methylphenyl)-1H-pyrazolo[3,4-d]pyrimidin-4-amine), PP2 (3-(4-chlorophenyl) 1-(1,1-dimethylethyl)-1H-pyrazolo[3,4-d]pyrimidin-4-amine), 1-NA PP1 (1-Naphthyl PP1; 1-(1,1-dimethylethyl)-3-(1-naphthalenyl)-1H-pyrazolo[3,4-d]pyrimidin-4-amine), 1-NM-PP1 (1-(1, 1-dimethylethyl)-3-(1-naphthalenylmethyl)-1H-pyrazolo[3,4-d]pyrimidin-4-amine), Src Inhibitor-1 (Src-I1; 6,7-Dimethoxy-N-(4-phenoxyphenyl)-4-quinazolinamine), Src Kinase Inhibitor I (CAS 179248-59-0), Src Kinase Inhibitor II (CAS 459848-35-2), A-419529, A-770041, AZM 475271, bosutinib, CGP77675, Damnacanthal, dasatinib, dasatinib monohydrate, ER 27319 maleate, Fingolimod (FTY720), Geldanamycin, Herbimycin A, KB SRC 4, KX2-391, KX1-004, Lavendustin A, Lavendustin C, LCK inhibitor 2, Lyn peptide inhibitor, MLR-1023, MNS, N-Acetyl-O-phosphono-Tyr-Glu Dipentylamide, N-Acetyl-O-phosphono-Tyr-Glu-Glu-Ile-Glu, NVP-BHG712, PD 166285, PD173952, PD 180970, Piceatannol, pp60 c-src, quercetin, radicicol from *Diheterospora chlamydosporia* solid, saracatinib, SU 6656, TC-S 7003, TG 100572, WH-4-023, ZM 306416, and combinations thereof.

Accordingly, the mammalian hepatocytes may be exposed to at least PP1. The mammalian hepatocytes may be exposed to at least PP2. The mammalian hepatocytes may be exposed to at least 1-NA PP1. The mammalian hepatocytes may be exposed to at least 1-NM-PP1. The mammalian hepatocytes may be exposed to at least Src Inhibitor-1. The mammalian hepatocytes may be exposed to at least Src Kinase Inhibitor I (CAS 179248-59-0). The mammalian hepatocytes may be exposed to at least Src Kinase Inhibitor II (CAS 459848-35-2). The mammalian hepatocytes may be exposed to at least A-419529. The mammalian hepatocytes may be exposed to at least A-770041. The mammalian hepatocytes may be exposed to at least AZM 475271. The mammalian hepatocytes may be exposed to at least bosutinib. The mammalian hepatocytes may be exposed to at least CGP77675. The mammalian hepatocytes may be exposed to at least Damnacanthal. The mammalian hepatocytes may be exposed to at least dasatinib. The mammalian hepatocytes may be exposed to at least dasatinib monohydrate. The mammalian hepatocytes may be exposed to at least ER 27319 maleate. The mammalian hepatocytes may be exposed to at least Fingolimod (FTY720). The mammalian hepatocytes may be exposed to at least Geldanamycin. The mammalian hepatocytes may be exposed to at least Herbimycin A. The mammalian hepatocytes may be exposed to at least KB SRC 4. The mammalian hepatocytes may be exposed to at least KX2-391. The mammalian hepatocytes may be exposed to at least KX1-004. The mammalian hepatocytes may be exposed to at least Lavendustin A. The mammalian hepatocytes may be exposed to at least Lavendustin C. The mammalian hepatocytes may be exposed to at least LCK inhibitor 2. The mammalian hepatocytes may be exposed to at least Lyn peptide inhibitor. The mammalian hepatocytes may be exposed to at least MLR-1023. The mammalian hepatocytes may be exposed to at least MNS, N-Acetyl-O-phosphono-Tyr-Glu Dipentylamide. The mammalian hepatocytes may be exposed to at least N-Acetyl-O-phosphono-Tyr-Glu-Glu-Ile-Glu. The mammalian hepatocytes may be exposed to at least NVP-BHG712. The mammalian hepatocytes may be exposed to at least PD 166285. The mammalian hepatocytes may be exposed to at least PD173952. The mammalian hepatocytes may be exposed to at least PD 180970. The mammalian hepatocytes may be exposed to at least Piceatannol. The mammalian hepatocytes may be exposed to at least pp60 c-src. The mammalian hepatocytes may be exposed to at least quercetin. The mammalian hepatocytes may be exposed to at least radicicol from *Diheterospora chlamydosporia* solid. The mammalian hepatocytes may be exposed to at least saracatinib. The mammalian hepatocytes may be exposed to at least SU 6656. The mammalian hepatocytes may be exposed to at least TC-S 7003. The mammalian hepatocytes may be exposed to at least TG 100572. The mammalian hepatocytes may be exposed to at least WH-4-023. The mammalian hepatocytes may be exposed to at least ZM 306416.

The mammalian hepatocytes may be exposed to any combinations of Src kinase inhibitors, such as any combination of the afore-mentioned compounds. For example, the mammalian hepatocytes may be exposed to at least PP1 and PP2.

Generally, the concentration of said at least one Src kinase inhibitor, when employed in accordance with the present invention, is in the range of about 0.05 to about 50 µM, such as, e.g., in the range of about 0.5 to about 10 µM.

The mammalian hepatocytes, such as human hepatocytes, may thus be exposed to said at least one Src kinase inhibitor at a concentration in the range of about 0.05 to about 25 µM. The mammalian hepatocytes may be exposed to said at least one Src kinase inhibitor at a concentration in the range of about 0.05 to about 15 µM. The mammalian hepatocytes may be exposed to said at least one Src kinase inhibitor at a concentration in the range of about 0.05 to about 10 µM. The mammalian hepatocytes may be exposed to said at least one Src kinase inhibitor at a concentration in the range of about 0.05 to about 7.5 µM. The mammalian hepatocytes may be exposed to said at least one Src kinase inhibitor at a concentration in the range of about 0.1 to about 25 µM. The mammalian hepatocytes may be exposed to said at least one Src kinase inhibitor at a concentration in the range of about 0.1 to about 15 µM. The mammalian hepatocytes may be exposed to said at least one Src kinase inhibitor at a concentration in the range of about 0.1 to about 15 µM. The mammalian hepatocytes may be exposed to said at least one Src kinase inhibitor at a concentration in the range of about 0.1 to about 10 µM. The mammalian hepatocytes may be exposed to said at least one Src kinase inhibitor at a concentration in the range of about 0.1 to about 7.5 µM. The mammalian hepatocytes may be exposed said at least one Src kinase inhibitor at a concentration in the range of about 0.5 to about 25 µM. The mammalian hepatocytes may be exposed to said at least one Src kinase inhibitor at a concentration in the range of about 0.5 to about 15 µM. The mammalian hepatocytes may be exposed to said at least one Src kinase inhibitor at a concentration in the range of about 0.5 to about 10 µM. The mammalian hepatocytes may be exposed to said at least one Src kinase inhibitor at a concentration in the range of about 0.5 to about 7.5 µM. The mammalian hepatocytes may be exposed to said at least one Src kinase inhibitor at a concentration in the range of about 1 to about 10 µM. The mammalian hepatocytes may be exposed to said at least one Src kinase inhibitor at a concentration in the range of about 1 to about 7.5 µM. The mammalian hepatocytes may be exposed to said at least one Src kinase inhibitor at a concentration in the range of about 1.5 to about 7.5 µM. The mammalian hepatocytes may be exposed to said at least one Src kinase inhibitor at a concentration in the range of about 2.5 to about 7.5 µM. The mammalian hepatocytes may be exposed to said at least one Src kinase inhibitor at a concentration in the range of about 3.5 to about 6.5 µM. The mammalian hepatocytes may be exposed to said at least one Src kinase inhibitor at a concentration in the range of about 4 to about 6 µM. The mammalian hepatocytes may be exposed said at least one Src kinase inhibitor at a concentration in the range of about 4.5 to about 5.5 µM. For example, The mammalian hepatocytes may be exposed to about 5 µM of said at least one Src kinase inhibitor.

In case that, for instance, PP1 is employed according to the invention, it may be employed at a concentration in the range of about 0.05 to about 50 µM, such as, e.g., in the range of about 0.5 to about 10 µM, such as, e.g., at about 5 µM.

Similar concentrations may be used in case that, for instance, PP2 is employed.

The at least one maturation factor employed in the methods of the invention may also be at least one vitamin D, vitamin D precursor, vitamin D metabolite or vitamin D analog, such as vitamin D1, D2, D3, D4 or D5, including precursors, metabolites and analogs thereof.

Accordingly, the mammalian hepatocytes may be exposed to at least vitamin D3 (cholecalciferol), a vitamin D3 precursor (such as 7-dehydrocholesterol), a vitamin D3 metabolite (such as calcifediol or calcitriol) and/or a vitamin D3 analog (such as calcipotriol, tacalcitol, ZK191784 or ZK203278)

The mammalian hepatocytes may be exposed to at least one vitamin D3 selected from the group consisting of cholecalciferol, calcifediol, calcitriol, and combinations thereof. The mammalian hepatocytes may be exposed to at least one vitamin D3 selected from the group consisting of cholecalciferol, calcitriol, and combinations thereof.

The mammalian hepatocytes may be exposed to at least cholecalciferol. The mammalian hepatocytes may be exposed to at least calcifediol. The mammalian hepatocytes may be exposed to at least calcitriol.

The mammalian hepatocytes may be exposed to at least cholecalciferol and calcifediol. The mammalian hepatocytes may be exposed to at least cholecalciferol and calcitriol. The mammalian hepatocytes may be exposed to at least calcifediol and calcitriol. The mammalian hepatocytes may be exposed to at least cholecalciferol, calcifediol and calcitriol.

The mammalian hepatocytes may be exposed to at least one vitamin D3 precursor, such as at least 7-dehydrocholesterol.

The mammalian hepatocytes may be exposed to at least one vitamin D3 analog selected from the group consisting of 22-oxacalcitriol (OCT), paricalcitol, doxercalciferol, calcipotriol, tacalcitol, ZK191784 and ZK203278. The mammalian hepatocytes may be exposed to at least calcipotriol.

Generally, the concentration of said at least one vitamin D, vitamin D precursor, vitamin D metabolite or vitamin D analog, when employed in accordance with the present invention, is in the range of about 0.05 to about 15 µM, such as, e.g., in the range of about 0.1 to about 5 µM.

The mammalian hepatocytes, such as human hepatocytes, may thus be exposed to said at least one vitamin D, vitamin D precursor, vitamin D metabolite or vitamin D analog at a concentration in the range of about 0.05 to about 10 µM. The mammalian hepatocytes may be exposed to said at least one vitamin D, vitamin D precursor, vitamin D metabolite or vitamin D analog at a concentration in the range of about 0.05 to about 7.5 µM. The mammalian hepatocytes may be exposed to said at least one vitamin D, vitamin D precursor, vitamin D metabolite or vitamin D analog at a concentration in the range of about 0.05 to about 5 µM. The mammalian hepatocytes may be exposed to said at least one vitamin D, vitamin D precursor, vitamin D metabolite or vitamin D analog at a concentration in the range of about 0.1 to about 10 µM. The mammalian hepatocytes may be exposed to said at least one vitamin D, vitamin D precursor, vitamin D metabolite or vitamin D analog at a concentration in the range of about 0.1 to about 7.5 µM. The mammalian hepatocytes may be exposed to said at least one vitamin D, vitamin D precursor, vitamin D metabolite or vitamin D analog at a concentration in the range of about 0.1 to about 5 µM. The mammalian hepatocytes may be exposed to said at least one vitamin D, vitamin D precursor, vitamin D metabolite or vitamin D analog at a concentration in the range of about 0.1 to about 2.5 µM. The mammalian hepatocytes may be exposed to said at least one vitamin D, vitamin D precursor, vitamin D metabolite or vitamin D analog at a concentration in the range of about 0.1 to about 1 µM. The mammalian hepatocytes may be exposed to said at least one vitamin D, vitamin D precursor, vitamin D metabolite or vitamin D analog at a concentration in the range of about 0.1 to about 0.75 µM. The mammalian hepatocytes may be exposed said at least one vitamin D, vitamin D precursor, vitamin D metabolite or vitamin D analog at a concentration in the range of about 0.25 to about 10 µM. The mammalian hepatocytes may be exposed to said at least one vitamin D, vitamin D precursor, vitamin D metabolite or vitamin D analog at a concentration in the range of about 0.25 to about 7.5 µM. The mammalian hepatocytes may be exposed to said at least one vitamin D, vitamin D precursor, vitamin D metabolite or vitamin D analog at a concentration in the range of about 0.25 to about 5 µM. The mammalian hepatocytes may be exposed to said at least one vitamin D, vitamin D precursor, vitamin D metabolite or vitamin D analog at a concentration in the range of about 0.25 to about 2.5 µM. The mammalian hepatocytes may be exposed to said at least one vitamin D, vitamin D precursor, vitamin D metabolite or vitamin D analog at a concentration in the range of about 0.25 to about 1 µM. The mammalian hepatocytes may be exposed to said at least one vitamin D, vitamin D precursor, vitamin D metabolite or vitamin D analog at a concentration in the range of about 0.25 to about 0.75 µM.

In case that, for instance, cholecalciferol is employed according to the invention, it may be employed at a concentration in the range of about 0.05 to about 15 µM, such as, e.g., in the range of about 0.1 to about 5 µM, about 0.1 to about 2.5 µM, about 0.1 to about 1 µM or about 0.1 to about 0.5, such as, e.g., at about 0.2 µM.

In case that, for instance, calcifediol is employed according to the invention, it may be employed at a concentration in the range of about 0.05 to about 15 µM, such as, e.g., in the range of about 0.1 to about 5 µM, about 0.1 to about 2.5 µM, about 0.1 to about 1 µM or about 0.25 to about 0.75, such as, e.g., at about 0.5 µM.

In case that, for instance, calcitriol is employed according to the invention, it may be employed at a concentration in the range of about 0.05 to about 15 µM, such as, e.g., in the range of about 0.1 to about 5 µM, about 0.1 to about 2.5 µM, about 0.1 to about 1 µM or about 0.25 to about 0.75, such as, e.g., at about 0.5 µM.

The at least one maturation factor employed in the methods of the invention may be at least one hypoxia inducing compound, such as, e.g, hypoxia inducing compound selected from the group consisting of RAR-related orphan receptor alpha (ROR-alpha) ligands, $CoCl_2$, and $NaN_3$.

Accordingly, the mammalian hepatocytes may be exposed to at least one RAR-related orphan receptor alpha (ROR-alpha) ligand, such as at least one RAR-related orphan receptor alpha (ROR-alpha) ligand selected from the group consisting of CGP52608, CGP52608 analogs, melatonin, melatonin analogs, cholesterol, cholesterol derivatives, and combinations thereof.

The mammalian hepatocytes may thus be exposed to at least CGP52608 or a CGP52608 analog. The mammalian hepatocytes may thus be exposed to at least CGP52608. The mammalian hepatocytes may also be exposed to at least a CGP52608 analog, such as CGP 53065, CGP 52528, CGP 53079, CGP 58238, CGP 52113, CGP 52749, CGP 55644, CGP 55706, CGP 55707, CGP 56753, CGP 55066 or GP 50468.

The mammalian hepatocytes may thus be exposed to at least melatonin or a melatonin analog. The mammalian hepatocytes may thus be exposed to at least melatonin. The mammalian hepatocytes may also be exposed to at least a melatonin analog, such as 6-methoxybenzoxazolinone, ramelteon ((S)—N-[2-(1,6,7,8-tetrahydro-2H-indeno[5,4-b]furan-8-yl)-ethyl]propionamide), agomelatine (N-(2-[7-methoxy-1-naphthalenyl]ethyl) acetamide) or synthetic kynurenines, such as 2-acetamide-4-(3-methoxyphenyl)-4-oxobutyric acid, 2-acetamide-4-(2-amino-5-methoxyphenyl)-4-oxobutyric acid, 2-butyramide-4-(3-methoxy-phenyl)-4-oxobutyric acid or 2-butyramide-4-(2-amino-5-methoxyphenyl)-4-oxobutyric acid.

The mammalian hepatocytes may thus be exposed to at least cholesterol or a cholesterol derivative.

The mammalian hepatocytes may thus be exposed to at least $CoCl_2$ or $NaN_3$

Generally, the concentration of said at least one hypoxia inducing compound, and in particularly said at least one RAR-related orphan receptor alpha (ROR-alpha) ligand, when employed in accordance with the present invention, is in the range of about 0.05 to about 50 µM, such as, e.g., in the range of about 0.5 to about 10 µM.

The mammalian hepatocytes, such as human hepatocytes, may thus be exposed to said at least one hypoxia inducing compound, and in particularly to said at least one RAR-related orphan receptor alpha (ROR-alpha) ligand, at a concentration in the range of about 0.05 to about 25 µM. The mammalian hepatocytes may be exposed to said at least one hypoxia inducing compound, and in particularly to said at least one RAR-related orphan receptor alpha (ROR-alpha) ligand, at a concentration in the range of about 0.05 to about 15 µM. The mammalian hepatocytes may be exposed to said at least one hypoxia inducing compound, and in particularly to said at least one RAR-related orphan receptor alpha (ROR-alpha) ligand, at a concentration in the range of about 0.05 to about 10 µM. The mammalian hepatocytes may be exposed to said at least one hypoxia inducing compound, and in particularly to said at least one RAR-related orphan receptor alpha (ROR-alpha) ligand, at a concentration in the range of about 0.05 to about 7.5 µM. The mammalian hepatocytes may be exposed to said at least one hypoxia inducing compound, and in particularly to said at least one RAR-related orphan receptor alpha (ROR-alpha) ligand, at a concentration in the range of about 0.1 to about 25 µM. The mammalian hepatocytes may be exposed to said at least one hypoxia inducing compound, and in particularly to said at least one RAR-related orphan receptor alpha (ROR-alpha) ligand, at a concentration in the range of about 0.1 to about 15 µM. The mammalian hepatocytes may be exposed to said at least hypoxia inducing compound, and in particularly to said at least one RAR-related orphan receptor alpha (ROR-alpha) ligand, at a concentration in the range of about 0.1 to about 15 µM. The mammalian hepatocytes may be exposed to said at least one hypoxia inducing compound, and in particularly to said at least one RAR-related orphan receptor alpha (ROR-alpha) ligand, at a concentration in the range of about 0.1 to about 10 µM. The mammalian hepatocytes may be exposed to said at least one hypoxia inducing compound, and in particularly to said at least one RAR-related orphan receptor alpha (ROR-alpha) ligand, at a concentration in the range of about 0.1 to about 7.5 µM. The mammalian hepatocytes may be exposed said at least one hypoxia inducing compound, and in particularly to said at least one RAR-related orphan receptor alpha (ROR-alpha) ligand, at a concentration in the range of about 0.5 to about 25 µM. The mammalian hepatocytes may be exposed to said at least one hypoxia inducing compound, and in particularly to said at least one RAR-related orphan receptor alpha (ROR-alpha) ligand, at a concentration in the range of about 0.5 to about 15 µM. The mammalian hepatocytes may be exposed to said at least one hypoxia inducing compound, and in particularly to said at least one RAR-related orphan receptor alpha (ROR-alpha) ligand, at a concentration in the range of about 0.5 to about 10 µM. The mammalian hepatocytes may be exposed to said at least one hypoxia inducing compound, and in particularly to said at least one RAR-related orphan receptor alpha (ROR-alpha) ligand, at a concentration in the range of about 0.5 to about 7.5 µM. The mammalian hepatocytes may be exposed to said at least one hypoxia inducing compound, and in particularly to said at least one RAR-related orphan receptor alpha (ROR-alpha) ligand, at a concentration in the range of about 1 to about 10 µM. The mammalian hepatocytes may be exposed to said at least one hypoxia inducing compound, and in particularly to said at least one RAR-related orphan receptor alpha (ROR-alpha) ligand, at a concentration in the range of about 1 to about 7.5 µM. The mammalian hepatocytes may be exposed to said at least one hypoxia inducing compound, and in particularly to said at least one RAR-related orphan receptor alpha (ROR-alpha) ligand, at a concentration in the range of about 1.5 to about 7.5 µM. The mammalian hepatocytes may be exposed to said at least one hypoxia inducing compound, and in particularly to said at least one RAR-related orphan receptor alpha (ROR-alpha) ligand, at a concentration in the range of about 2.5 to about 7.5 µM. The mammalian hepatocytes may be exposed to said at least one hypoxia inducing compound, and in particularly to said at least one RAR-related orphan receptor alpha (ROR-alpha) ligand, at a concentration in the range of about 3.5 to about 6.5 µM. The mammalian hepatocytes may be exposed to said at least one hypoxia inducing compound, and in particularly to said at least one RAR-related orphan receptor alpha (ROR-alpha) ligand, at a concentration in the range of about 4 to about 6 µM. The mammalian hepatocytes may be exposed said at least one hypoxia inducing compound, and in particularly to said at least one RAR-related orphan receptor alpha (ROR-alpha) ligand, at a concentration in the range of about 4.5 to about 5.5 µM. For example, The mammalian hepatocytes may be exposed to about 5 µM of said at least one hypoxia inducing compound, and in particularly of said at least one RAR-related orphan receptor alpha (ROR-alpha) ligand.

In case that, for instance, CGP52608 is employed according to the invention, it may be employed at a concentration in the range of about 0.05 to about 50 µM, such as, e.g., in the range of about 0.5 to about 10 µM, such as, e.g., at about 5 µM.

The at least one maturation factor employed in the methods of the invention may also be at least one sphingosine, such as D-erythro-sphingosine or L-erythro-sphingosine, or a sphingosine derivative, such as sphingosine-1-phosphate or a sphingolipid.

Accordingly, the mammalian hepatocytes may be exposed to at least one sphingosine. More specifically, the mammalian hepatocytes may be exposed to at least D-erythro-sphingosine. The mammalian hepatocytes may be exposed to at least L-erythro-sphingosine.

The mammalian hepatocytes may be exposed to at least a sphingosine derivative.

The mammalian hepatocytes may be exposed to at least a sphingosine derivative selected from the group consisting of sphingosine-1-phosphate, dihydrosphingosine, such as DL-erythro-dihydrosphingosine, L-threo-sphingosine C-18, Azido-erythro-sphingosine, 3-O-(tert-Butyldimethylsilyloxy)-erythro-sphingosine, (2S,3R,4E)-2-Azido-3-(tert-butyldimethylsilyl)-1-pivaloyl-erythro-sphingosine, 3-O-(tert-Butyldimethylsilyloxy)-2-Fmoc-erythro-sphingosine, (2S,3R,4E)-2-Azido-3-(tert-butyldimethylsilyl)-erythro-sphingosine, N-Boc-erythro-sphingosine, Safingol, and ceramides.

The mammalian hepatocytes may thus be exposed to at least sphingosine-1-phosphate, such as D-erythro-sphingosine or L-erythro-sphingosine. The mammalian hepatocytes may be exposed to at least D-erythro-sphingosine-1-phosphate. The mammalian hepatocytes may be exposed to at least L-erythro-sphingosine-1-phosphate.

The mammalian hepatocytes may be exposed to at least a sphingolipid, such as a ceramide or a ceramide analog. The ceramide may, for instance, be a $N-C_{2-24}$-ceramide, such as a N-C12-, N-C14-, N-C16- or N-C18-ceramide. More specifically, the ceramide may be a D-erythro-ceramide, such as a N-C16-D-erythro-ceramide. The ceramide may be a L-erythro-ceramide, such as a N-C16-L-erythro-ceramide. The ceramide analog may be MAPP, such as L-erythro MAPP or D-erythro MAPP.

The mammalian hepatocytes may thus be exposed to at least a ceramide or ceramide analog. The mammalian hepatocytes may be exposed to at least a ceramide. The mammalian hepatocytes may be exposed to at least a ceramide analog. The mammalian hepatocytes may thus be exposed to at least a $N-C_{2-24}$-ceramide, such as a N-C10-, N-C12-, N-C14-, N-C16-, N-C18- or N-C20-ceramide. The mammalian hepatocytes may be exposed to at least a N-C16-ceramide, such as N-C16-D-erythro-ceramide (N-palmitoyl-D-erythro-sphingosine).

Generally, the concentration of said at least one sphingosine or sphingosine derivative, when employed in accordance with the present invention, is in the range of about 0.05 to about 15 µM, such as, e.g., in the range of about 0.1 to about 5 µM.

The mammalian hepatocytes, such as human hepatocytes, may thus be exposed to said at least one sphingosine or sphingosine derivative at a concentration in the range of about 0.05 to about 10 µM. The mammalian hepatocytes may be exposed to said at least one sphingosine or sphingosine derivative at a concentration in the range of about 0.05 to about 7.5 µM. The mammalian hepatocytes may be exposed to said at least one sphingosine or sphingosine derivative at a concentration in the range of about 0.05 to about 5 µM. The mammalian hepatocytes may be exposed to said at least one sphingosine or sphingosine derivative at a concentration in the range of about 0.1 to about 10 µM. The mammalian hepatocytes may be exposed to said at least one sphingosine or sphingosine derivative at a concentration in the range of about 0.1 to about 7.5 µM. The mammalian hepatocytes may be exposed to said at least one sphingosine or sphingosine derivative at a concentration in the range of about 0.1 to about 5 µM. The mammalian hepatocytes may be exposed to said at least one sphingosine or sphingosine derivative at a concentration in the range of about 0.1 to about 2.5 µM. The mammalian hepatocytes may be exposed to said at least one sphingosine or sphingosine derivative at a concentration in the range of about 0.1 to about 1 µM. The mammalian hepatocytes may be exposed to said at least one sphingosine or sphingosine derivative at a concentration in the range of about 0.1 to about 0.75 µM. The mammalian hepatocytes may be exposed said at least one sphingosine or sphingosine derivative at a concentration in the range of about 0.25 to about 10 µM. The mammalian hepatocytes may be exposed to said at least one sphingosine or sphingosine derivative at a concentration in the range of about 0.25 to about 7.5 µM. The mammalian hepatocytes may be exposed to said at least one sphingosine or sphingosine derivative at a concentration in the range of about 0.25 to about 5 µM. The mammalian hepatocytes may be exposed to said at least one sphingosine or sphingosine derivative at a concentration in the range of about 0.25 to about 2.5 µM. The mammalian hepatocytes may be exposed to said at least one sphingosine or sphingosine derivative at a concentration in the range of about 0.25 to about 1 µM. The mammalian hepatocytes may be exposed to said at least one sphingosine or sphingosine derivative at a concentration in the range of about 0.25 to about 0.75 µM.

In case that, for instance, sphingosine, such as D-erythro-sphingosine, is employed according to the invention, it may be employed at a concentration in the range of about 0.05 to about 15 µM, such as, e.g., in the range of about 0.1 to about 5 µM, about 0.1 to about 2.5 µM, about 0.1 to about 1 µM or about 0.25 to about 0.75, such as, e.g., at about 0.5 µM.

In case that, for instance, a sphingosine-1-phosphate, such as D-erythro-sphingosine-1-phosphate, is employed according to the invention, it may be employed at a concentration in the range of about 0.05 to about 15 µM, such as, e.g., in the range of about 0.1 to about 5 µM, about 0.1 to about 2.5 µM, about 0.1 to about 1 µM or about 0.25 to about 0.75, such as, e.g., at about 0.5 µM.

In case that, for instance, a ceramide, such as N-C16-D-erythro-ceramide, is employed according to the invention, it may be employed at a concentration in the range of about 0.05 to about 15 µM, such as, e.g., in the range of about 0.1 to about 5 µM, about 0.1 to about 2.5 µM, about 0.1 to about 1 µM or about 0.25 to about 0.75, such as, e.g., at about 0.5 µM.

The at least one maturation factor employed in the methods of the invention may also be at least one activator of peroxisome proliferator-activated receptors (PPARs), such as at least one activator of peroxisome proliferator-activated receptors (PPARs) selected from the group consisting of thiazolidinediones, free fatty acids (FFAs), eicosanoids including eicosanoid precursors and eicosanoid analog, and combinations thereof.

Accordingly, the mammalian hepatocytes, such as human hepatocytes, may be exposed to at least one thiazolidinedione, such as at least one thiazolidinedione selected from the group consisting of CGP52608, CGP52608 analogs, ciglitazone, rosiglitazone, pioglitazone, lobeglitazone, troglitazone, TS5444, and combinations thereof.

The mammalian hepatocytes, such as human hepatocytes, may be exposed to at least one free fatty acid, such as a saturated or unsaturated fatty acid.

The mammalian hepatocytes may be exposed to at least one saturated fatty acid, such as at least one saturated fatty acid selected from the group consisting of dodecanoic acid, tridecanoic acid, tetradecanoic acid, pentadecanoic acid, hexadecanoic acid, heptadecanoic acid, eicosanoic acid, heneicosanoic acid, docosanoic acid, tricosanoic acid, tetracosanoic acid, pentacosanoic acid, hexacosanoic acid, and combinations thereof.

The mammalian hepatocytes may be exposed, for instance, to at least tetradecanoic acid.

The mammalian hepatocytes may be exposed to at least one unsaturated fatty acid, such as at least one unsaturated fatty acid selected from the group consisting of 10Z-heptadecenoic acid, arachidonic acid (AA), 9(Z),11(E)-Conjugated Linoleic Acid, eicosadienoic acid, eicosatrienoic acid (ETE), eicosapentaenoic acid (EPA), docosapentaenoic acid (DPA), docosahexaenoic acid (DHA), linoleic acid, gamma-linolenic acid, dihomo-gamma-linolenic acid, docosadienoic acid, adrenic acid, mead acid, ricinoleic acid, docosatrienoic acid, and combinations thereof.

The mammalian hepatocytes may be exposed, for instance, to at least one unsaturated fatty acid selected from the group consisting of 10Z-heptadecenoic acid, arachidonic acid (AA), Docosahexaenoic acid (DHA), and combinations thereof. The mammalian hepatocytes may thus be exposed to at least 10Z-heptadecenoic acid. The mammalian hepatocytes may thus be exposed to at least arachidonic acid (AA). The mammalian hepatocytes may be exposed to at least Docosahexaenoic acid (DHA). The mammalian hepatocytes may thus be exposed to at least 10Z-heptadecenoic acid and arachidonic acid (AA). The mammalian hepatocytes may thus be exposed to at least 10Z-heptadecenoic acid and Docosahexaenoic acid (DHA). The mammalian hepatocytes may thus be exposed to at least arachidonic acid (AA) and Docosahexaenoic acid (DHA). The mammalian hepatocytes may thus be exposed to at least 10Z-heptadecenoic acid, arachidonic acid (AA) and Docosahexaenoic acid (DHA).

The mammalian hepatocytes may be exposed to at least one eicosanoid, eicosanoid precursor or eicosanoid analog, such as at least one eicosanoid, eicosanoid precursor or eicosanoid analog selected from the group consisting of Diacylglycerol, Eicosapentaenoic acid, Dihomo-gamma-linolenic acid, Arachidonic acid, ETYA (5,8,11,14-eicosatetraynoic acid), members of the hydroxyeicosatetraenoic acid (HETE) family, including 5-HETE and 15-HETE, members of the hydroxyoctadecadieonic acid (HODE) family, including 9-HODE and 13-HODE, classic eicosanoids, and non-classic eicosanoids.

The mammalian hepatocytes may be exposed, for instance, to at least one classic eicosanoid, such as at least one classic eicosanoid selected from the group consisting of prostaglandins, prostacyclines, leukotriens, eoxins, thromboxanes, and analogs, precursors or derivatives thereof.

The mammalian hepatocytes may be exposed to at least one prostaglandin, such as at least one prostaglandin selected from the group consisting of $pgd_2$, $pgd_3$, $pge_1$, $pge_2$, $pge_3$, $pgf_{1c}$, $pgf_{2a}$, $pgf_3$, and $pgj_2$.

The mammalian hepatocytes may be exposed to at least one prostacyclin, such as at least one prostacyclins selected from the group consisting of $pgi_2$ and $pgi_3$.

The mammalian hepatocytes may be exposed to at least one leukotriene, such as at least one are selected leukotriene from the group consisting of $Lta_4$, $Lta_5$, $Ltb_4$, $Ltb_5$, $Ltc_4$, $Ltc_5$, $Ltd_4$, $Ltd_5$, $Lte_4$, and $Lte_5$.

The mammalian hepatocytes may be exposed to at least one eoxin, such as at least one eoxin selected from the group consisting of 14,15-leukotriene A4, 14,15-leukotriene C4, 14,15-leukotriene D4, and 14,15-leukotriene E4.

The mammalian hepatocytes may be exposed to at least one thromboxane, such as at least one thromboxane selected from the group consisting of $Txa_1$, $Txa_2$, and $Txa_3$.

The mammalian hepatocytes may be exposed, for instance, to at least one non-classic eicosanoid, such as at least one nonclassic eicosanoid selected from the group consisting of endocannabinoids, hepoxilins, resolvins, isofurans, isoprastanes, lipoxins, epi-lipoxins, epoxyeicosatrieonic acids (EETs).

The mammalian hepatocytes may be exposed to at least one endocannabionoid, such as at least one endocannabionoid selected from the group consisting of anandamides, WIN55, 212-2, palmitylethanolamide, mead ethanolamid, R-mathandamide, BML-190, N-arachidonylglycine, and arachidonamide.

Generally, the concentration of said at least one activator of peroxisome proliferator-activated receptors (PPARs), when employed in accordance with the present invention, is in the range of about 0.05 to about 50 µM, such as, e.g., in the range of about 0.5 to about 10 µM.

The mammalian hepatocytes, such as human hepatocytes, may thus be exposed to said at least one activator of peroxisome proliferator-activated receptors (PPARs) at a concentration in the range of about 0.05 to about 10 µM. The mammalian hepatocytes may be exposed to said at least one activator of peroxisome proliferator-activated receptors (PPARs) at a concentration in the range of about 0.05 to about 7.5 µM. The mammalian hepatocytes may be exposed to said at least one activator of peroxisome proliferator-activated receptors (PPARs) at a concentration in the range of about 0.05 to about 5 µM. The mammalian hepatocytes may be exposed to said at least one activator of peroxisome proliferator-activated receptors (PPARs) at a concentration in the range of about 0.1 to about 10 µM. The mammalian hepatocytes may be exposed to said at least one activator of peroxisome proliferator-activated receptors (PPARs) at a concentration in the range of about 0.1 to about 7.5 µM. The mammalian hepatocytes may be exposed to said at least one activator of peroxisome proliferator-activated receptors (PPARs) at a concentration in the range of about 0.1 to about 5 µM. The mammalian hepatocytes may be exposed to said at least one activator of peroxisome proliferator-activated receptors (PPARs) at a concentration in the range of about 0.1 to about 2.5 µM. The mammalian hepatocytes may be exposed to said at least one activator of peroxisome proliferator-activated receptors (PPARs) at a concentration in the range of about 0.1 to about 1 µM. The mammalian hepatocytes may be exposed to said at least one activator of peroxisome proliferator-activated receptors (PPARs) at a concentration in the range of about 0.1 to about 0.75 µM. The mammalian hepatocytes may be exposed said at least one activator of peroxisome proliferator-activated receptors (PPARs) at a concentration in the range of about 0.25 to about 10 µM. The mammalian hepatocytes may be exposed to said at least one activator of peroxisome proliferator-activated receptors (PPARs) at a concentration in the range of about 0.25 to about 7.5 µM. The mammalian hepatocytes may be exposed to said at least one activator of peroxisome proliferator-activated receptors (PPARs) at a concentration in the range of about 0.25 to about 5 µM. The mammalian hepatocytes may be exposed to said at least one activator of peroxisome proliferator-activated receptors (PPARs) at a concentration in the range of about 0.25 to about 2.5 µM. The mammalian hepatocytes may be exposed to said at least one activator of peroxisome proliferator-activated receptors (PPARs) at a concentration in the range of about 0.25 to about 1 µM. The mammalian hepatocytes may be exposed to said at least one activator of peroxisome proliferator-activated receptors (PPARs) at a concentration in the range of about 0.25 to about 0.75 µM.

In case that, for instance, at least one thiazolidinedione is employed according to the invention, it may be employed at a concentration in the range of about 0.05 to about 50 µM, such as, e.g., in the range of about 0.5 to about 10 µM.

In case that, for instance, at least one saturated fatty acid, such as tetradecanoic acid, is employed according to the invention, it may be employed at a concentration in the range of about 0.05 to about 50 µM, such as, e.g., in the range of about 0.5 to about 10 µM, about 1 to about 10 µM, or about 2.5 to about 7.5 µM.

In case that, for instance, at least one unsaturated fatty acid, is employed according to the invention, it may be employed at a concentration in the range of about 0.05 to about 15 µM, such as, e.g., in the range of about 0.1 to about 5 µM, about 0.1 to about 2.5 µM, about 0.1 to about 1 µM or about 0.25 to about 0.75, such as, e.g., at about 0.5 µM.

More specifically, in case that, for instance, 10Z-heptadecenoic acid, is employed according to the invention, it may be employed at a concentration in the range of about about 0.05 to about 15 µM, such as, e.g., in the range of about 0.1 to about 5 µM, about 0.1 to about 2.5 µM, about 0.1 to about 1 µM or about 0.25 to about 0.75, such as, e.g., at about 0.5 µM.

In case that, for instance, arachidonic acid (AA), is employed according to the invention, it may be employed at a concentration in the range of about 0.05 to about 15 µM, such as, e.g., in the range of about 0.1 to about 5 µM, about 0.1 to about 2.5 µM, about 0.1 to about 1 µM or about 0.25 to about 0.75, such as, e.g., at about 0.5 µM.

In case that, for instance, Docosahexaenoic acid (DHA), is employed according to the invention, it may be employed at a concentration in the range of about 0.05 to about 15 µM, such as, e.g., in the range of about 0.1 to about 5 µM, about 0.1 to about 2.5 µM, about 0.1 to about 1 µM or about 0.25 to about 0.75, such as, e.g., at about 0.5 µM.

The at least one maturation factor employed in the methods of the invention may also be at least one platelet-activating factor (1-alkyl-2-acetyl-sn-glycero-3-phosphocholine; PAF), such as 1-$C_{1-24}$-alkyl-2-acetyl-sn-glycero-3-phosphocholine ($C_{1-24}$-PAF).

The mammalian hepatocytes, such as human hepatocytes, may be exposed to at least one 1-$C_{1-24}$-alkyl-2-acetyl-sn-glycero-3-phosphocholine ($C_{1-24}$-PAF), such as at least one 1-$C_{1-24}$-alkyl-2-acetyl-sn-glycero-3-phosphocholine ($C_{12-20}$-PAF). The mammalian hepatocytes may, for example, be exposed to 1-hexadecyl-2-acetyl-sn-glycero-3-phosphocholine (C16-PAF). The mammalian hepatocytes may, for example, be exposed to 1-octadecyl-2-acetyl-sn-glycero-3-phosphocholine (C18-PAF).

Generally, the concentration of said at least one platelet-activating factor, when employed in accordance with the present invention, is in the range of about 0.05 to about 15 µM, such as, e.g., in the range of about 0.1 to about 5 µM.

The mammalian hepatocytes, such as human hepatocytes, may thus be exposed to said at least one platelet-activating factor at a concentration in the range of about 0.05 to about 10 µM. The mammalian hepatocytes may be exposed to said at least platelet-activating factor at a concentration in the range of about 0.05 to about 7.5 µM. The mammalian hepatocytes may be exposed to said at least one platelet-activating factor at a concentration in the range of about 0.05 to about 5 µM. The mammalian hepatocytes may be exposed to said at least one platelet-activating factor at a concentration in the range of about 0.1 to about 10 µM. The mammalian hepatocytes may be exposed to said at least one platelet-activating factor at a concentration in the range of about 0.1 to about 7.5 µM. The mammalian hepatocytes may be exposed to said at least one platelet-activating factor at a concentration in the range of about 0.1 to about 5 µM. The mammalian hepatocytes may be exposed to said at least one platelet-activating factor at a concentration in the range of about 0.1 to about 2.5 µM. The mammalian hepatocytes may be exposed to said at least one platelet-activating factor at a concentration in the range of about 0.1 to about 1 µM. The mammalian hepatocytes may be exposed to said at least one platelet-activating factor at a concentration in the range of about 0.1 to about 0.75 µM. The mammalian hepatocytes may be exposed said at least one platelet-activating factor at a concentration in the range of about 0.25 to about 10 µM. The mammalian hepatocytes may be exposed to said at least one platelet-activating factor at a concentration in the range of about 0.25 to about 7.5 µM. The mammalian hepatocytes may be exposed to said at least one platelet-activating factor at a concentration in the range of about 0.25 to about 5 µM. The mammalian hepatocytes may be exposed to said at least one platelet-activating factor at a concentration in the range of about 0.25 to about 2.5 µM. The mammalian hepatocytes may be exposed to said at least one platelet-activating factor at a concentration in the range of about 0.25 to about 1 µM. The mammalian hepatocytes may be exposed to said at least one platelet-activating factor at a concentration in the range of about 0.25 to about 0.75 µM.

In case that, for instance, 1-hexadecyl-2-acetyl-sn-glycero-3-phosphocholine (C16-PAF), is employed according to the invention, it may be employed at a concentration in the range of about 0.05 to about 15 µM, such as, e.g., in the range of about 0.1 to about 5 µM, about 0.1 to about 2.5 µM, about 0.1 to about 1 µM or about 0.25 to about 0.75, such as, e.g., at about 0.5 µM.

The at least one maturation factor employed in the methods of the invention may also be at least one protein kinase C (PKC) inhibitor, such as at least one PKC inhibitor selected from the group consisting of Bisindolylmaleimide I, Bisindolylmaleimide II, Bisindolylmaleimide III, Bisindolylmaleimide V, Bisindolylmaleimide VI, Bisindolylmaleimide VII, Bisindolylmaleimide VIII, Bisindolylmaleimide X, HBDDE, Rottlerin, Palmitoyl-DL-carnitine, R-Stearoyl Carnitine Chloride, Piceatannol, H-9, H-8, 1-(5-Isoquinolinesulfonyl)-3-methylpiperazine, HA-100 dihydrochloride, HA-1004, HA-1077, 5-Iodotubericidin, Ro-32-0432, Ro-31-7549, Enzastaurin (LY317615), Sotrastaurin, Dequalinium Chloride, Go 6976, Go 6983, Go 7874, Myricitrin, 4-Hydroxy-Tamoxifen, N-Desmethyltamoxifen HCl, Safingol, Phloretin, UCN-01, 7-Oxostaurosporine, K-252a, K-252b, K-252c, Melittin, Hispidin, Calphostin C, Ellagic acid, PKC Inhibitor Peptide 19-31, PKC Inhibitor Peptide 19-36, PKC epsilon Translocation Inhibitor II, EGF-R Fragment 651-658, PKC beta inhibitor (CAS 257879-35-9), PKC 20-28, PKCβII/EGFR Inhibitor (CAS 145915-60-2), PKCθ Pseudosubstrate Inhibitor, PKCθ/δ Inhibitor, [Ala107]-MBP (104-118), [Ala113]-MBP (104-118), ZIP, C-1, Bryostatin 1, LY 333531 hydrochloride, CGP 53353, Chelerythrine Chloride, TCS 21311, CID 755673, Gossypol, ET-18-OCH3, 1-O-Hexadecyl-2-O-methyl-rac-glycerol, NPC-15437 dihydrochloride, NGIC-I, MDL-27.032, DAPH-7, 7-Aminoindole, 5-Amino-2-methylindole, rac-2-Methoxy-3-hexadecanamido-1-propylphosphocholine, Copper bis-3,5-diisopropylsalicylate, D,L-3,4-Dihydroxymandelic Acid, rac-3-Octadecanamido-2-Methoxypropan-1-ol Phosphocholine, KRIBB3, Ilmofosine, rac-2-Methoxy-3-hexadecanamido-1-propylphosphocholine, and combinations thereof.

Generally, the concentration of said at least one protein kinase C (PKC) inhibitor, when employed in accordance with the present invention, is in the range of about 0.01 to about 50 µM, such as, e.g., in the range of about 0.5 to about 10 µM.

The mammalian hepatocytes, such as human hepatocytes, may not only be exposed to one maturation factor, but may be exposed to a combination of maturation factors described herein, such as a combination comprising at least two, such as at least three, at least four, at least five, at least six, at least seven, or at last eight, of the maturation factors described herein.

Accordingly, the mammalian hepatocytes, such as human hepatocytes, may be exposed to a combination comprising at least two maturation factors. The mammalian hepatocytes, such as human hepatocytes, may be exposed to a combination comprising at least three maturation factors. The mammalian hepatocytes, such as human hepatocytes, may be exposed to a combination comprising at least four maturation factors. The mammalian hepatocytes, such as human hepatocytes, may be exposed to a combination comprising at least five maturation factors. The mammalian hepatocytes, such as human hepatocytes, may be exposed to a combination comprising at least six maturation factors. The mammalian hepatocytes, such as human hepatocytes, may be exposed to a combination comprising at least seven maturation factors. The mammalian hepatocytes, such as human hepatocytes, may be exposed to a combination comprising at least eight maturation factors.

The mammalian hepatocytes, such as human hepatocytes, may be exposed to any one of the combinations of the following items:

a) a combination comprising at least two maturation factor(s) selected from the group Src kinase inhibitors, vitamin D including precursors, metabolites and analog thereof, hypoxia inducing compounds, sphingosine derivatives, activators of peroxisome proliferator-activated receptors (PPARs), platelet-activating factor (PAF), PKC inhibitors, and combinations thereof;

b) a combination according to item a), comprising at least one (such as at least two) Src kinase inhibitor;
c) a combination according to item a) or b), comprising at least one (such as at least two) vitamin D, vitamin D precursor, vitamin D metabolite or vitamin D analog;
d) a combination according to any one of items a) to c), comprise at least one (such as at least two) sphingosine and sphingosine derivative;
e) a combination according to any one of items a) to d), comprising at least one (such as at least two) activator of peroxisome proliferator-activated receptors (PPARs);
f) a combination according to any one of items a) to e), comprising at least one (such as at least two) platelet-activating factor (PAF);
g) a combination according to any one of items a) to f), comprising at least one (such as at least two) PKC inhibitor.

The differentiating and maturing hepatic cells may, for example, be exposed to the at least one maturation factor for up to about 35 days. They may, for example, be exposed to the at least one maturation factor for about 2 days to about 30 days. They may be exposed to the at least one maturation factor for about 2 days to about 25 days. They may be exposed to the at least one maturation factor for about 2 days to about 20 days. They may be exposed to the at least one maturation factor for about 2 days to about 15 days. They may be exposed to the at least one maturation factor for about 7 days to about 35 days. They may be exposed to the at least one maturation factor for about 7 days to about 30 days. They may be exposed to the at least one maturation factor for about 7 days to about 25 days. They may be exposed to the at least one maturation factor for about 7 days to about 20 days. They may be exposed to the at least one maturation factor for about 10 days to about 35 days. They may be exposed to the at least one maturation factor for about 10 days to about 30 days. They may be exposed to the at least one maturation factor for about 10 days to about 25 days. They may be exposed to the at least one maturation factor for about 10 days to about 20 days.

In accordance with the invention, the at least one maturation factor may be added to the differentiation medium at any time point after initiation of culturing mammalian hepatic progenitor cells under differentiation conditions to obtain said mammalian hepatocytes, such as after 4 days of culturing. Thus, in addition to exposing said mammalian hepatocytes to said at least one maturation factor, said mammalian hepatic progenitor cells may also be exposed to said at least one maturation factor. However, usually, the at least one maturation factor is added to the differentiation medium at a time t≥day 7 after initiation of culturing mammalian hepatic progenitor cells under differentiation conditions to obtain said mammalian hepatocytes.

In addition to being exposed to at least one maturation factors as described herein, the mammalian hepatocytes (and optionally also said mammalian hepatic progenitor cells from which said mammalian hepatocytes are derived) may optionally also be exposed to an overlay of one or more components characteristic of the mammalian extracellular matrix (matrix overlay). Thus, the exposure to the at least one maturation factors is further combined with the exposure to a matrix overlay.

Matrix overlays consisting of Collagen I or Matrigel (a basement membrane mix extracted from the Engelbreth-Holm-Swarm mouse sarcoma) have been used for culturing primary hepatocytes for several decades (e.g. Dunn et al. 1991; Page et al. 2007), since it was found that primary hepatocytes maintain a better functionality and live longer in a so called sandwich configuration, with one extracellular matrix (ECM) layer below the cells and one ECM layer on top of the cells. Classically, Collagen I and Matrigel overlays are thick, containing e.g. 125 µg Matrigel/cm$^2$ or 50 µg Collagen I/cm$^2$. However, this is not reflecting the physiological composition or thickness of the liver ECM (compare e.g. Turner et al. 2011; Wang et al. 2011).

The matrix overlay employed in the methods of the invention is a novel, more physiological combination of component present in the ECM of the adult liver and comprises, or is composed of, one or more ECM components, which form part of the normal mammalian extracellular matrix environment. Suitable ECM components for use as matrix overlay in the present invention are collagen, such as collagen I, II, III, IV, V or VI, fibronectin, elastin, chondroitin sulfate proteoglycan, dermatan sulfate proteoglycan, heparin proteoglycan, heparan sulfate proteoglycan, such as glypicans, syndecans or perlecans, glycosaminoglycans, nidogen/entactin, laminins, biglycan, tenascin, hyaluronans, or other ECM components, or ECM component mixtures comprising, or consisting of, e.g., collagens, laminin, fibronectin, tenascin, proteoglycans, and glycosaminoglycans.

Accordingly, the mammalian hepatocytes (and optionally said mammalian hepatic progenitor cells from which said mammalian hepatocytes are derived) may be exposed to a matrix overlay comprising, or composed of, one or more, such as two, three, four, five, six, seven, eight, nine or ten, or up to 20 of the above mentioned ECM components. Thus, the mammalian hepatocytes may be exposed to a matrix overlay comprising, or composed of, two of the above mentioned ECM components.

For example, the mammalian hepatocytes may be exposed to a matrix overlay comprising, or composed of, collagen and fibronectin (collagen-fibronectin-matrix overlay), such as a matrix overlay comprising, or composed of, collagen I and fibronectin (collagen I-fibronectin-matrix overlay).

The matrix overlay employed in the methods of the invention is thin compared to the thick matrices so far used. The thickness of the matrix overlay thereby correlates with the concentration of the ECM components employed. Suitable concentrations for the matrix overlay are e.g. 0.01-35 µg, such as 0.01-20 µg, ECM component/cm$^2$ culture area. However, it is also contemplated that higher concentrations may be used.

Collagen I may, for example, be present in the matrix overlay at a concentration from about 2 to about 150 µg/cm$^2$ culture area, such as from about 30 to 150 µg/cm$^2$ culture area, such as about 31.25 µg/cm$^2$ culture area.

Fibronectin may, for example, be present in the matrix overlay at a concentration from about 2 to about 30 µg/cm$^2$ culture area, such as from about 2 to about 10 µg/cm$^2$ culture area, such as about 6 µg/cm$^2$ culture area.

It is to be understood that the above concentrations in "µg/cm$^2$ culture area" are with respect to the respective component in its dry state.

Further matrix overlays which can be employed in the methods of the invention are described in WO2014/083132 (page 43, line 7 to page 47, line 29), the content of which is hereby incorporated by reference.

Generally, cells may be cultured on a coating as growth support which covers the surface of the culture vessel. Gelatine or fibronectin based coating are widely used as growth support. Thus, the cells, in particular the hepatic progenitor cells and hepatocyte, may be cultured on a gelatin or fibronectin based coating. However, the cells may also be cultured on a coating which has a composition similar or identical to a matrix overlay as defined above. For example, when a matrix overlay is to be employed, the cells may be cultured on a coating which has a composition which is identical to that of the employed matrix overlay. Accordingly, a so-called "sandwich" type culture environment is provided. The cells may, for example, be cultured on Collagen I-fibronectin-based coating. Such Collagen I-Fibronectin-based coating may have a concentration of about 2 to about 10 µg, such as about 2 µg, Fibronectin and about 2 to about 12 µg, such as about 10 µg, Collagen I per cm$^2$ culture area.

The mammalian cells employed in the present invention may, for instance, be human cells, primate cells, mouse cells, rat cells, canine cells, feline cells, porcine cells, bovine cells or equine cells. Thus, the methods of the present invention may be based on and directed to human cells.

As an optional pre-step, the mammalian hepatic progenitor cells used in the methods of the invention may initially be derived from mammalian pluripotent stem (PS) cells, such as from mammalian embryonic stem (ES) cells or mammalian artificial pluripotent stem cells, such as mammalian induced pluripotent stem (iPS) cells. The methods of the invention may thus further comprise as an initial step the culturing of mammalian PS cells under differentiation conditions to obtain said hepatic progenitor cells. In accordance thereto, mammalian PS cells are initially differentiated into said hepatic progenitor cells. This step is referred to herein as initial hepatic differentiation.

The mammalian pluripotent stem cells employed in the present invention may, for instance, be human pluripotent stem cells, primate pluripotent stem cells, mouse pluripotent stem cells, rat pluripotent stem cells, canine pluripotent stem cells, feline pluripotent stem cells, porcine pluripotent stem cells, bovine pluripotent stem cells or equine pluripotent stem cells.

Especially, the mammalian pluripotent stem cells employed in the present invention may be any type of human pluripotent stem cells, such as human embryonic stem (hES) cells or human artificial pluripotent stem cells, such as human induced pluripotent stem (hiPS) cells.

As indicated above, pluripotent stem cells which may also be used as starting material to obtain endodermal and/or hepatic progenitor cells may be embryonic stem cells, such as human embryonic stem cells. Various techniques for obtaining ES cells, such as hES cells, are known to the skilled person. For example, hES cells for use according to the invention may be derived (or obtained) by employing the single blastomere removal technique described in e.g. Chung et al (2008), further described by Mercader et al. in Essential Stem Cell Methods (First Edition, 2009). Alternatively, established and publically available stem cells lines may be used. Suitable hES cell lines for use are those established by Klimanskaya et al. (2006), such as cell lines MA01 and MA09, and Chung et al. (2008), such as cell lines MA126, MA127, MA128 and MA129, which all are listed with the International Stem Cell Registry (assigned to Advanced Cell Technology, Inc. Worcester, Mass., USA). Other suitable hES cell lines for use are, for example, the cell lines SA167, SA181, SA461 (Takara Bio Europe AB, Göteborg, Sweden).

Alternatively, the pluripotent stem cells which may be used as starting material to obtain the definitive endodermal cells and/or hepatic progenitor cells may be artificial pluripotent stem cells. Various techniques for obtaining artificial pluripotent stem cells are known to the skilled person, and include artificial reprogramming methods such as somatic nuclear transfer (SCNT), ES cell fusion-mediated reprogramming (FMR), chemical stimulation of oocytes (parthenogenetic stem cells) and induced pluripotency (iPS). Techniques for obtaining hiPS cells are, for example, described in Takahashi et al. (2007); Zhou et al. (2009); Yu and Thomson in Essentials of Stem Cell Biology ($2^{nd}$ Edition].

It is also envisaged that the endodermal and/or hepatic progenitor cells may also be derived from other pluripotent stem cells such as adult stem cells, cancer stem cells or from other embryonic, fetal, juvenile or adult sources. For example, hepatic progenitor cells used in accordance with the invention may be hepatic progenitor derived from the liver, so-called LDPCs. Such LDPCs have been shown to be capable of hepatic differentiation both in vitro and in vivo.

Suitable conditions for differentiating mammalian pluripotent stem cells, especially hPS cells, into hepatic progenitor cells are known (see, e.g., Hay 2008, Brolen 2010 and Duan 2010). WO 2009/013254 A1, for example, describes suitable protocols to obtain cells of the hepatic progenitor cells from hPS cells (Embodiments 1 to 4).

The mammalian pluripotent stem cells, such as hPS cells, are cultured for up to 14 days in suitable differentiation medium in order to obtain hepatic progenitor cells. For example, the mammalian pluripotent stem cells, especially hPS cells, may be cultured in suitable differentiation medium for about 6 to about 14 days, such as for about 7 to 11 days.

The initial hepatic differentiation may be defined by including a pre-endodermal step, i.e. the culturing of the mammalian pluripotent stem cells, such as hPS cells, under differentiation conditions to obtain cells of the definitive endoderm (DE cells), which is followed by a pre-hepatic step, i.e. the culturing of the obtained DE cells under differentiation conditions to obtain the hepatic progenitor cells. Accordingly, hPS cells are first differentiated into definitive endoderm, followed by the further differentiation of the definitive endoderm into hepatic progenitor cells.

Suitable conditions for differentiating mammalian pluripotent stem cells, especially hPS cells, into DE cells are known (see, e.g., D'Amour 2005; Siller 2015). WO 2009/013254 A1, for example, describes suitable protocols to obtain cells of the definitive endoderm from hPS cells (Embodiments 1 to 4). An alternative protocol for differentiating mammalian pluripotent stem cells, especially hPS cells, into DE cells without using activin is described by Siller et al (2015).

Generally, in order to obtain DE cells, mammalian pluripotent stem cells, such as hPS cells, may be cultured in one or more differentiation media comprising one or more of activin, such as activin A or B, an albumin source, such as FBS, FCS, N2, B27 or BSA, a GSK3-inhibitor, such as, e.g., CHIR99021. One or more differentiation media may comprise activin, such as activin A. One or more differentiation medium may include a histone deacetylase (HDAC) inhibitor, such as Sodium Butyrate (NaB), Phenylbutyrate (PB), valproate, trichostatin A, Entinostat or Panobinstat. One or more differentiation media may comprise one or more growth factors, such as FGF1, FGF2 and FGF4. The differentiation media may comprise an albumin source, such as FBS, FCS, N2, B27 or BSA. One or more differentiation media may comprise a GSK3-inhibitor, such as, e.g., CHIR99021, or an activator of Wnt signalling, such as Wnt3A. One or more differentiation media may comprise a PI3K (Phosphoinositide 3-kinase) inhibitor, such as LY294002.

The concentration of activin, if present, is usually in the range of about 50 to about 150 ng/ml, such as about 80 to about 120 ng/ml. Activin may, for example, be present in the differentiation medium at a concentration of about 50 ng/ml or about 100 ng/ml. The concentration of the HDAC inhibitor, if present, is usually in the range of about 0.5 to about 2 mM. The HDAC inhibitor may, for example, be present in the differentiation medium at a concentration of about 0.5 mM or about 1 mM. The concentration of the one or more growth factors, if present, may vary depending on the particular compound used. The concentration of FGF2, for example, is usually in the range of about 2 to about 50 ng/ml, such as about 2 to about 10 ng/ml. FGF2 may, for example, be present in the differentiation medium at a concentration of about 4 or about 5 ng/ml. The concentration of FGF1, for example, is usually in the range of about 50 to about 200 ng/ml, such as about 80 to about 120 ng/ml. FGF1 may, for example, be present in the differentiation medium at a concentration of about 100 ng/ml. The concentration of FGF4, for example, is usually in the range of about 20 to about 40 ng/ml. FGF4 may, for example, be present in the differentiation medium at a concentration of about 30 ng/ml. The concentration of the albumin source, if present, is usually in the range of about 0.1 to about 2% v/v, such as about 0.1 to about 0.5%, about 0.2 to about 1.5% v/v, about 0.2 to about 1% v/v, about 0.5 to 1% v/v or about 0.5 to about 1.5% v/v. The albumin source may, for example, be present in the differentiation medium at a concentration of about 0.2% v/v, about 0.5% v/v or about 1% v/v. The concentration of the GSK3 inhibitor, if present, is usually in the range of about 0.1 to about 10 µM, such as about 0.05 to about 5 µM. The concentration of the activator of Wnt signalling, if present, is usually in the range of about 0.05 to about 10 ng/ml, such as about 0, 5 to about 5 µM. The concentration of the PI3K inhibitor, for example, is usually in the range of about 0.1 to 10 µM, such as about 1 to 5 µM.

The differentiation medium may further comprise other supplements such as PEST and/or GlutaMAX. The differentiation medium may also further comprise a ROCK inhibitor. The concentration of PEST is usually in the range of about 0.1 to about 0.5% v/v, such as about 0.1 to about 0.25% v/v. The concentration of GlutaMAX is usually in the range of about 0.5 to about 1.5% v/v, such as about 0.75 to 1.25% v/v, e.g. about 1% v/v. The differentiation medium may also further comprise a ROCK inhibitor. The concentration of the ROCK inhibitor is usually in the range of about 1 to about 10 µM, such as about 2.5 to about 7.5 µM, e.g., about 5 µM.

The culture medium forming the basis for the differentiation medium may be any culture medium suitable for culturing hPS cells such as such as such as RPMI 1640 medium, RPMI 1640 advanced medium, Iscove's Modified Dulbeccos Medium (IMDM), Minimum Essential Medium (e.g., MEM, EMEM or GMEM), Dulbecco's Modified Eagle Medium (e.g., DMEM or DMEM/F-12), Ham's medium (e.g., Ham's F12 or Ham's F10), HCM medium, HBM medium, or Williams E medium. Thus, the base medium may, for example, be RPMI 1640 medium or RPMI 1640 advanced medium. Alternatively, the base medium may be Williams E medium.

The differentiating mammalian pluripotent stem cells, such as hPS cells, may be exposed to a DNA demethylating agent. Cells may be exposed to (or treated with) said agent at any stage between pluripotent stem cell stage and definitive endodermal stage. Thus, the exposure to said DNA demethylating agent may take place during the differentiation of the PS cells into DE cells, i.e. during the pre-endodermal step. The cells are then cultured through endodermal stage until hepatic progenitor stage is reached, i.e. until hepatic progenitor cells are obtained, at which point the further differentiation and maturation into hepatocytes, including the exposure to the at least one maturation factor, is carried out.

The DNA demethylating agent may be any compound that interferes with DNA methyltransferase enzyme activity. Suitable DNA demethylating agents are ones of the nucleoside-analog type, such as cytidine analogues, e.g. 5-aza-2-deoxycytidine (decitabine), 5-azacytidine (azacitidine) or zebularine, and of the non-nucleoside type, such as procaine, RG108, S-5-adenosyl-L-homocysteine, Caffeic acid, Chlorogenic acid, Epogallocatechin gallate, Hydralazine hydrochloride, Procainamide hydrochloride or Psammaplin A.

The differentiating mammalian PS cells may generally be exposed to the DNA demethylating agent at a concentration in the range of about 1 nM to about 10 µM, such as in the range of about 1 nM to about 5 µM. In case that, for instance, 5-aza-2-deoxycytidine is employed as the DNA demethylating agent, the differentiating PS cells may be exposed to it at a concentration in the range of 1 nM to about 1 µM, such as in the range of 1 nM to 50 nM, such as at about 10 nM.

For endodermal differentiation, mammalian pluripotent stem cells, such as hPS cells, are normally cultured for up to 10 days in an activin containing differentiation medium as described above. The mammalian pluripotent stem cells, such as hPS cells, may, for example, be cultured in said differentiation medium for about 2 to about 10 days, such as for about 7 to about 9 days.

Instead of de novo preparation of DE cells from pluripotent stem cells, DE cells obtainable from commercial sources may be employed and used as starting material in accordance with the invention. Human definitive endoderm cells may, for example, be obtained upon request from Takara Bio Europe AB, Arvid Wallgrens Backe 20, 41346 Gothenburg, Sweden.

In order to obtain hepatic progenitor cells, DE cells are generally cultured in a differentiation medium comprising DMSO. Alternatively, the DE cells may be cultured in a differentiation medium comprising one or more growth factors, such as FGF1, FGF2 and FGF4, and optionally one or more bone morphogenic proteins, such as BMP2 and BMP4. The differentiation medium may further comprise HGF, EGF and/or serum.

The concentration of DMSO is usually in the range of about 0.1% to about 2% v/v, such as about 0.5% to about 1.5% v/v. DMSO may, for example, be present in the differentiation medium at a concentration of about 1%. The concentration of the one or more growth factors may vary depending on the particular compound used. The concentration of FGF2, for example, is usually in the range of about 2 to about 50 ng/ml, such as about 2 to about 10 ng/ml. FGF2 may, for example, be present in the differentiation medium at a concentration of 4 or 5 ng/ml. The concentration of FGF1, for example, is usually in the range of about 50 to about 200 ng/ml, such as about 80 to about 120 ng/ml. FGF1 may, for example, be present in the differentiation medium at a concentration of about 100 ng/ml. The concentration of FGF4, for example, is usually in the range of about 20 to about 40 ng/ml. FGF4 may, for example, be present in the differentiation medium at a concentration of about 30 ng/ml. The concentration of HGF, if present, is usually in the range of about 10 to about 30 ng/ml. HGF may, for example, be present in the differentiation medium at a concentration of about 20 ng/ml. The concentration of EGF, if present is usually in the range of about 5 to about 15 ng/ml. EGF may, for example, be present in the differentiation medium at a concentration of about 10 ng/ml. The concentration of serum, if present, is usually in the range of about 0.1 to about 2% v/v, such as such as about 0.1 to about 0.5%, about 0.2 to about 1.5% v/v, about 0.2 to about 1% v/v, about 0.5 to 1% v/v or about 0.5 to about 1.5% v/v. Serum may, for example, be present in the differentiation medium at a concentration of about 0.2% v/v, about 0.5% v/v or about 1% v/v.

The differentiation medium may further comprise other supplements such as PEST and/or GlutaMAX. The concentration of PEST is usually in the range of about 0.1 to about 0.5% v/v, such as about 0.1 to about 0.25% v/v. The concentration of GlutaMAX is usually in the range of about 0.5 to about 1.5% v/v, such as about 0.75 to 1.25% v/v, e.g. about 1% v/v.

The differentiation medium may further comprise other supplements such as Knockout-Serum Replacement, non-essential amino acids (NEAA) and/or beta-mercaptoethanol. The concentration of Knockout-Serum Replacement is usually in the range of about 10 to about 30% v/v, such as about 15 to about 25% v/v, e.g., about 20% v/v. The concentration of non-essential amino acids (NEAA) is usually in the range of about 0.5 to about 1.5% v/v, such as about 0.75 to 1.25% v/v, e.g. about 1% v/v. The concentration of non-essential amino acids (NEAA) is usually in the range of about 0.1 to about 0.5% v/v, such as about 0.1 to 0.3% v/v, e.g. about 0.2% v/v.

The culture medium forming the basis for the differentiation medium may be any culture medium suitable for culturing human endodermal cells such as such as such as RPMI 1640 medium, RPMI 1640 advanced medium, Iscove's Modified Dulbeccos Medium (IMDM), Minimum Essential Medium (e.g., MEM, EMEM or GMEM), Dulbecco's Modified Eagle Medium (e.g., DMEM or DMEM/F-12), Ham's medium (e.g., Ham's F12 or Ham's F10), HCM medium, HBM medium, or Williams E medium. Thus, the base medium may, for example, be RPMI 1640 medium or RPMI 1640 advanced medium. Alternatively, the base medium may be Williams E medium.

For differentiation into hepatic progenitor cells, DE cells are normally cultured for up to 7 days in differentiation medium as described above. The DE cells may, for example, be cultured in differentiation medium for about 4 to about 7 days.

Basic, non-limiting culture conditions for obtaining DE cells, hepatic progenitor cells and hepatocyte are also provided in Example 2 herein.

Further, the hepatocyte of the present invention may be obtained under xeno-free conditions. As such, the starting material employed in the methods of the invention may thus be xeno-free, such as xeno-free PS cells or cell lines, or xeno-free hepatic progenitor cells or cell lines which have been obtained or established under animal-free conditions.

Moreover, throughout the methods of the invention cells may be cultured completely under xeno-free conditions, giving rise to truly xeno-free hepatocyte. Such cells or cell line would be better suited to therapeutic or regenerative medicine applications and could be distinguished from a non-xeno free composition by the presence in non-xeno free cells of the non-human sialic acid Neu5Gc or other non-human markers (Martin et al 2005).

As a result of the methods of the present invention, mammalian hepatocytes are obtained with more mature and functional features compared to currently available state of the art methods.

The mammalian hepatocytes obtained by employing the methods of the invention show elevated expression of hepatocyte-associated genes such as e.g. CYP1A, CYP3A4, CYP2C9, CYP2C19, CYP2B6 and/or CYP2D6 (see FIGS. 1 to 4).

The mammalian hepatocyte obtained by employing the methods of the invention and principles as laid out in present invention may be used to a multitude of purposes comprising drug discovery processes, toxicity test, for studying drug transporters, drug metabolizing enzyme, as in vitro models for studying hepatogenesis, such as, e.g., early hepatogenesis, for studying human hepatoregenerative disorders, for in vitro hepatotoxicity testing.

Further the mammalian hepatocyte obtained by employing the methods of the invention may be used for therapeutic purposes comprising: in a medicament, for the manufacture of a medicament or medicinal product for the prevention and/or treatment of pathologies and/or diseases caused by tissue degeneration, such as, e.g., the degeneration of liver tissue. The mammalian hepatocytes of the present invention may also be used for the manufacture of a medicament or medicinal product for the treatment of liver disorders. Liver disorders are, for example, auto immune disorders including primary biliary cirrhosis; metabolic disorders including dyslipidemia; liver disorders caused by e.g. alcohol abuse; diseases caused by viruses such as, e.g., hepatitis B, hepatitis C, and hepatitis A; liver necrosis caused by acute toxic reactions to e. g. pharmaceutical drugs; and tumour removal in patients suffering from e. g. hepatocellular carcinoma.

Alternatively, the mammalian hepatocytes obtained by employing the methods of the invention may be used for the manufacture of a medicament or medicinal product for the treatment and/or prevention of metabolic pathologies and/or diseases. The medicament or medicinal product may, for example, be in the form of a replacement tissue or cell injection.

The differentiation and maturation of mammalian hepatocytes in accordance to the invention may be useful for obtaining metabolically improved hepatocytes, for studying maturation towards hepatocytes or for screening a compound for its ability to modulate hepatocellular function, comprising exposing in vitro derived hepatocytes obtained according to the directions provided herein to the compound, determining any phenotypic or metabolic changes in the cells that result from contact with the compound, and correlating the change with an ability to modulate hepatocellular function.

The present invention also provides compositions and kits. Such composition or kits are particularly useful in carrying out the methods of the invention, e.g, for maturing mammalian hepatocytes in accordance with the invention.

A composition of the invention comprises at least one maturation factor as described above. Thus, a composition of the invention comprises at least one (such as at least two) maturation factor(s) selected from the group Src kinase inhibitors, vitamin D including precursors, metabolites and analog thereof, hypoxia inducing compounds, sphingosine and sphingosine derivatives, activators of peroxisome proliferator-activated receptors (PPARs), platelet-activating factor (PAF), PKC inhibitors, and combinations thereof.

A composition of the invention may thus be any one of the following items:
a) A composition of the invention comprises at least one (such as at least two) maturation factor(s) selected from the group Src kinase inhibitors, vitamin D including precursors, metabolites and analog thereof, hypoxia inducing compounds, sphingosine and sphingosine derivatives, activators of peroxisome proliferator-activated receptors (PPARs), platelet-activating factor (PAF), PKC inhibitors, and combinations thereof;

b) a composition according to item a), comprising at least one (such as at least two) Src kinase inhibitor;

c) a composition according to item a) or b), comprising at least one (such as at least two) vitamin D, vitamin D precursor, vitamin D metabolite or vitamin D analog;

d) a composition according to any one of items a) to c), comprise at least one (such as at least two) sphingosine and sphingosine derivative;

e) a composition according to any one of items a) to d), comprising at least one (such as at least two) activator of peroxisome proliferator-activated receptors (PPARs);

f) a composition according to any one of items a) to e), comprising at least one (such as at least two) platelet-activating factor (PAF);

g) a composition according to any one of items a) to f), comprising at least one (such as at least two) PKC inhibitor.

It is understood that all details given above with respect to the maturation factors employed in the methods of the invention, including all combinations and embodiments, especially type of maturation factor and respective concentrations, also apply to maturation factors comprised by the composition of the invention.

Optionally, the composition may further comprise at least one (such as at least two) extracellular matrix (ECM) component or ECM component mixture as described above. The composition may, for instance, further comprise collagen I and fibronectin.

The present invention also provides a culture medium comprising a composition of the invention. Such culture medium is particularly useful in carrying out the methods of the invention, e.g, for maturing mammalian hepatocytes in accordance with the invention.

The culture medium may be based on any suitable culture medium such as such as RPMI 1640 medium, RPMI 1640 advanced medium, Iscove's Modified Dulbeccos Medium (IMDM), Minimum Essential Medium (e.g., MEM, EMEM or GMEM), Dulbecco's Modified Eagle Medium (e.g., DMEM or DMEM/F-12), Ham's medium (e.g., Ham's F12 or Ham's F10), HCM medium, HBM medium, or Williams E medium. Thus, the base medium may, for example, be RPMI 1640 medium or RPMI 1640 advanced medium. Alternatively, the base medium may be Williams E medium.

The culture medium, besides comprising a composition of the invention, may optionally comprise additional components, such as those optional components described above in the context of the differentiation medium for obtaining hepatocytes from hepatic progenitor cells.

The present invention further provides kits. Such kits are particularly useful in carrying out the methods of the invention, e.g, for maturing human hepatocyte-like cells in accordance with the invention. A kit according to the invention comprises at least one (such as at least two) maturation factor(s) selected from the group Src kinase inhibitors, vitamin D including precursors, metabolites and analog thereof, hypoxia inducing compounds, sphingosine and sphingosine derivatives, activators of peroxisome proliferator-activated receptors (PPARs), platelet-activating factor (PAF), PKC inhibitors, and combinations thereof.

It is understood that all details given above with respect to the maturation factors employed in the methods of the invention, including all combinations and embodiments, especially type of maturation factor and respective concentrations, also apply to maturation factors comprised by the kit of the invention.

A kit according to the present invention may comprise a composition of the present invention.

A kit according to the invention may comprise a culture medium of the present invention.

A kit according to the present invention may comprise the least one (such as at least two) maturation factor(s) at a concentration which is about to 2 to about 100 fold, such as about 10 to about 50 fold, higher than the concentration employed in the methods of the invention. In such case, the concentration may have to be adjusted to the actual concentration prior to use, such as by dilution.

A kit of the invention may further comprise mammalian definitive endoderm cells (DE cells), such as human DE cells. The DE cells may suitably be provided as a cell suspension, or may be provided in a frozen state.

A kit of the invention may further comprise mammalian pluripotent stem cells, such as human pluripotent stem cells. Hence, a kit of the invention may comprise mammalian embryonic stem cells or mammalian induced pluripotent stem cells. The mammalian pluripotent stem cells may suitably be provided as a cell suspension, or may be provided in a frozen state.

The components of a kit of the invention may be provided in the same or separate containers. For instance, the at least one (such as at least two) maturation factor(s) may be provided in the same container. If an at least one extracellular matrix (ECM) component or ECM component mixture is also comprised by the kit, such ECM component or ECM component mixture may be generally provided in a separate container.

Likewise, if mammalian definitive endoderm cells or mammalian pluripotent stem cells are comprised by a kit, DE cells or pluripotent stem cells are generally provide in a container which is different from the container(s) containing the other components.

Definitions

As used herein, "pluripotent" or "pluripotency" refers to the potential to form all types of specialized cells of the three germ layers (endoderm, mesoderm, and ectoderm); and is to be distinguished from "totipotent" or "totipotency", that is the ability to form a complete embryo capable of giving rise to offsprings.

As used herein, "pluripotent stem cells" (PSC) refers to cells that have the capacity, under appropriate conditions, to self-renew as well as the ability to form any type of specialized cells of the three germ layers (endoderm, mesoderm, and ectoderm). PS cells may have the ability to form a teratoma in 8-12 week old SCID mice and/or the ability to form identifiable cells of all three germ layers in tissue culture. Included in the definition of pluripotent stem cells are embryonic cells of various types including human embryonic stem (hES) cells, (see, e.g., Thomson et al. (1998), Heins et. al. (2004), as well as induced pluripotent stem cells [see, e.g. Takahashi et al., (2007); Zhou et al. (2009); Yu and Thomson in Essentials of Stem Cell Biology ($2^{nd}$ Edition]. The various methods described herein may utilise PS cells from a variety of sources. For example, PS cells, and especially human PS cells, suitable for use may have been obtained from developing embryos by use of a non-destructive technique such as by employing the single blastomere removal technique described in e.g. Chung et al (2008), further described by Mercader et al. in Essential Stem Cell Methods (First Edition, 2009). Additionally or alternatively, suitable PS cells may be obtained from established cell lines or may be adult stem cells.

As used herein "iPS cells" refers to induced pluripotent stem cells. iPS cells are a type of pluripotent stem cells derived from non-pluripotent cells—typically adult somatic cells—by induction of the expression of genes associated with pluripotency, such as SSEA-3, SSEA-4, TRA-1-60, TRA-1-81, Oct-4, Sox2, Nanog and Lin28.

As used herein "hiPS cells" refers to human induced pluripotent stem cells. hiPS cells are a type of pluripotent stem cells derived from non-pluripotent cells—typically adult somatic cells—by induction of the expression of genes associated with pluripotency, such as SSEA-3, SSEA-4, TRA-1-60, TRA-1-81, Oct-4, Sox2, Nanog and Lin28.

As used herein "definitive endoderm (DE)" and "definitive endoderm cells (DE cells)" refers to cells exhibiting protein and/or gene expression as well as morphology typical to cells of the definitive endoderm or a composition comprising a significant number of cells resembling the cells of the definitive endoderm. The definitive endoderm is the germ cell layer which gives rise to cells of the intestine, pancreas, liver and lung. DE cells may generally be characterized, and thus identified, by a positive gene and protein expression of the endodermal markers FOXA2, CXCR4, HHEX, SOX17, GATA4 and GATA6. The two markers SOX17 and CXCR4 are specific for DE and not detected in hPSC, hepatic progenitor cells or hepatocytes. Lastly, DE cells do not exhibit gene and protein expression of the undifferentiated cell markers Oct4, SSEA-3, SSEA-4, TRA-1-60, TRA-1-81, but can show low Nanog expression.

As used herein, "hepatic progenitors" or "hepatic progenitor cells" refers to cells which have entered the hepatic cell path and give rise to hepatocyte. "Hepatic progenitors" are thus distinguished from "endodermal cells" in that they have lost the potential to develop into cells of the intestine, pancreas and lung. "Hepatic progenitors" may generally be characterized, and thus identified, by a positive gene and protein expression of the early hepatic markers EpCAM, c-Met (HGF-receptor), AFP, CK19, HNF6, C/EBPα and β. They do not exhibit gene and protein expression of the DE-markers CXCR4 and SOX17. Lastly, "hepatic progenitors" do not exhibit gene and protein expression of the undifferentiated cell markers Oct4, SSEA-3, SSEA-4, TRA-1-60 and TRA-1-81 nor the mature hepatic markers CYP1A2, CYP2C9, CYP19, CYP3A4, CYP2B6 and PXR.

As used herein, "hepatocytes" refers to fully differentiated hepatic cells. "Hepatocytes" may generally be described, and thus identified, by a positive gene and protein expression of the mature hepatic markers CYP1A2, CYP3A4, CYP2C9, CYP2C19, CYP2B6, GSTA1-1, OATP-2, NTCP, Albumin, PXR, CAR, and HNF4a (isoforms 1+2) among others. Further, "hepatocytes" do not exhibit gene and protein expression of the undifferentiated cell markers Oct4, SSEA-3, SSEA-4, TRA-1-60 and TRA-1-81. Compared to DE cells, "hepatocytes" do not exhibit gene and protein expression of the DE cell markers SOX17 and CXCR4. Compared to "hepatic progenitors", "hepatocytes" do not exhibit gene and protein expression of the hepatic progenitor markers Cytokeratin 19 and AFP.

As meant herein, a gene or protein shall be interpreted as being "expressed", if in an experiment measuring the expression level of said gene or protein, the determined expression level is higher than three times the standard deviation of the determination, wherein the expression level and the standard deviation are determined in 10 separate determinations of the expression level. The determination of the expression level in the 10 separate determinations is preferably corrected for background-signal.

As used herein HDAC inhibitors refers to Histone deacetylase inhibitors, such as Sodium Butyrate ("NaB"), Phenyl Butyrate ("PB"), Trichostatin A and Valproic Acid ("VA").

As used herein, "GSK inhibitor" refers to a compound which inhibits GSK (especially GSK3, including GSK3alpha or GSK3beta).

As used herein, a DNA demethylating agent is intended to mean a compound that interferes with DNA methyltransferase enzyme activity, such as nucleoside analogues, like cytidine analogs, notably 5-aza-2-deoxycytidine (decitabine) and 5-azacytidine (azacitidine), and non-nucleoside types, such as RG108, S-5-Adenosyl-L-homocysteine, and procaine.

As used herein "CYP" is intended to mean Cytochrome P, and more specifically Cytochrome P 450, the major phase I metabolizing enzyme of the liver constituting of many different isoenzymes, such as CYP1A1, CYP1A2, CYP1B1, CYP2A6/2A7/2A13, CYP2B6, CYP2C8, CYP2C9, CYP2C19, CYP2D6, CYP2E1, CYP3A4, CYP3A5, CYP3A7 and CYP7A1.

As used herein, the term "GST" is intended to mean glutathione transferase, and examples of subtypes thereof are GST A1-1, GST M1-1, and GST P1-1.

As used herein the term "UGT" is intended to mean uridine diphosphoglucuronosyltransferase, which is a group of liver enzymes catalyzing glucuronidation activities.

As used herein the term "NTCP" is taken to mean Na+-taurocholate cotransporting polypeptide, a Sodium/bile acid co-transporter encoded by the gene SLC10A1

As used herein the term "CAR" is taken to mean Constitutive androstane receptor

The term "functional drug metabolising enzymes" is intended to mean functional enzymes belonging to the phase I and phase II enzymes that perform chemical modifications of xenobiotics and drugs, so called drug or xenobiotic metabolism.

As used herein, the term "functional activity" means effective measurable hepatic cell function, such as a measurable transportation of drugs for drug transporters and a measurable metabolism of enzymes for the Cytochrome P450s (CYPs), commonly detected in primary human hepatocytes.

As used herein, the term "extraembryonic endoderm (ExE)" is intended to mean the differentiated endodermal cells that, as to the opposite of the definitive endoderm, will constitute the compartments outside the embryo in the human development, such as the yolk sac.

As used herein, the term "AAT" is intended to mean the liver marker alpha-anti-trypsin.

As used herein, the term "AFP" is intended to mean the liver marker alpha-fetoprotein.

As used herein, the term "BSEP" is intended to mean the bile transporter bile salt export pump.

As used herein, the term "CK" is intended to mean the liver marker cytokeratin (used interchangeably) with different subtypes such as Cytokeratin 18 (CK18/KRT18), Cytokeratin 19 (CK19/KRT19), Cytokeratin 8 (CK8) and Cytokeratin 7 (CK7).

As used herein, the term "FGF" means fibroblast growth factor, preferably of human and/or recombinant origin, and subtypes belonging thereto are e.g. "bFGF" (means basic fibroblast growth factor, sometimes also referred to as FGF2) and FGF4. "aFGF" means acidic fibroblast growth factor (sometimes also referred to as FGF1).

As used herein, the term "BMP" means Bone Morphogenic Protein, preferably of human and/or recombinant origin, and subtypes belonging thereto are e.g. BMP4 and BMP2.

As used herein, the term "HGF" means Hepatocyte Growth Factor, preferably of human and/or recombinant origin.

As used herein, the term "EGF" means Epidermal Growth Factor, preferably or human and/or recombinant origin.

As used herein, the "HNF4alpha", or "HNF4a", used interchangeably are intended to mean hepatocyte nuclear factor 4 also known as NR2A1 (nuclear receptor subfamily 2, group A, member 1), a transcription factor regulating gene expression in endodermal derived tissue, e.g. the liver, pancreatic islets, and adipocytes. The encoded protein controls the expression of several genes, including hepatocyte nuclear factor 1 alpha.

As used herein, the term "MDR" is intended to mean multi-drug resistance transporter. MDR 1 and 3 are members of the ATP-binding cassette (ABC) family of transporters and both are drug efflux transporters. MDR 1 is important in regulating the traffic of drugs, peptides and xenobiotics into the body and in protecting the body against xenobiotic insults and drug toxicity, while MDR 3 is essential for phospholipid secretion into bile.

As used herein, the term "Activin" is intended to mean a TGF-beta family member that exhibits a wide range of biological activities including regulation of cellular proliferation and differentiation such as "Activin A" or "Activin B". Activin belongs to the common TGF-beta superfamiliy of ligands.

As used herein, the term "activator of a retinoic acid responsive receptor" is intended to mean a compound capable of binding to and activating a human retinoic acid receptor (RAR) and/or retinoid X receptor (RXRs).

As used herein, the term "retinoic acid receptor" or "RAR" is intended to mean a member of the family of retinoic acid receptors, in particular RAR-alpha, RAR-beta, and RAR-gamma, which are encoded by the RARA, RARB, RARG genes, respectively. Each receptor isoform has several splice variants: two for alpha, four for beta, and two for gamma. These isoforms are also included in the definition of a "retinoic acid receptor".

As used herein, the term "retinoic acid" is intended to mean a retinoic acid isomer, including but not limited to all-trans-retinoic acid, 7-cis-retinoic acid, 9-cis retinoic acid, 11-cis-retinoic acid and 13-cis retinoic.

As used herein, the term "inhibitor of a cyclin dependent kinase" or "CDK inhibitor" is intended to mean a compound capable of inhibiting the function (e.g., the activity) of a cyclin dependent kinase, such as cyclin dependent kinase 2 (CDK2).

As used herein, the term "ROCK inhibitor" is intended to mean an inhibitor of ROCK Rho-associated protein kinase activity As used herein, the term "matrix" is intended to refer to any component, either isolated or in combination, which forms part of the normal mammalian extracellular matrix environment. Such matrix components include, but are not limited to, collagen, fibronectin, and laminin and may be from natural or synthetic sources.

As used herein, the term "overlay" is intended to refer to a layer of, e.g., extracellular matrix components, which is applied on top of the cultured cells.

As used herein, the term "coating" is intended to refer to a layer of, e.g., extracellular matrix components, which covers the surface of a culture vessel and on which the cells are cultured.

As used herein the term "xeno-free" is intended to mean complete circumvention of direct or in-direct exposure to non-human animal components.

As used herein, the term "hepatocellular toxicity" indicates cellular responses such as necrotic toxicity, apoptosis, mitochondrial toxicity, phospholipidosis, steatosis and bile acid transport.

Figure 1A:
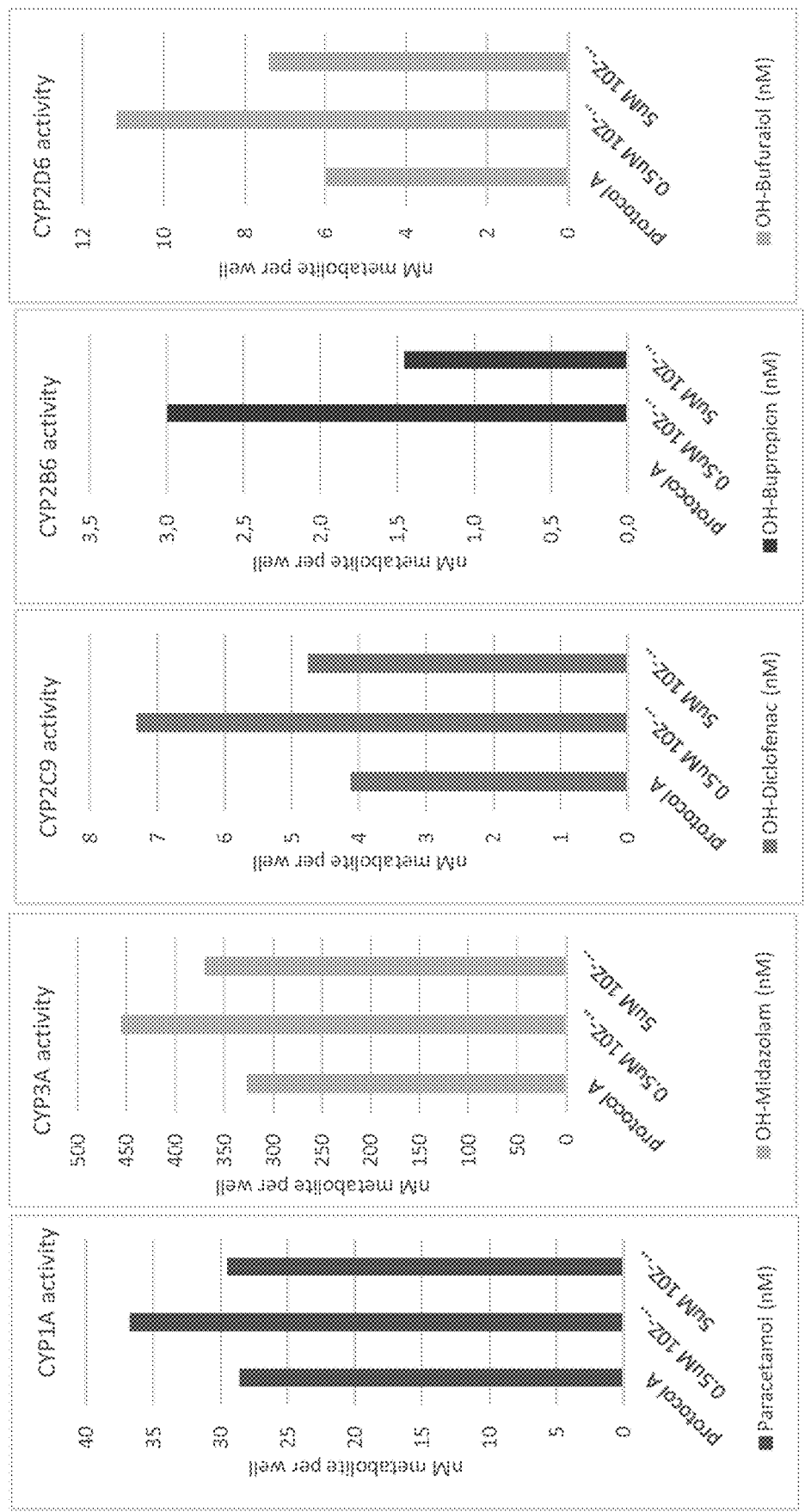
FIG. 1.
Figure 1B:
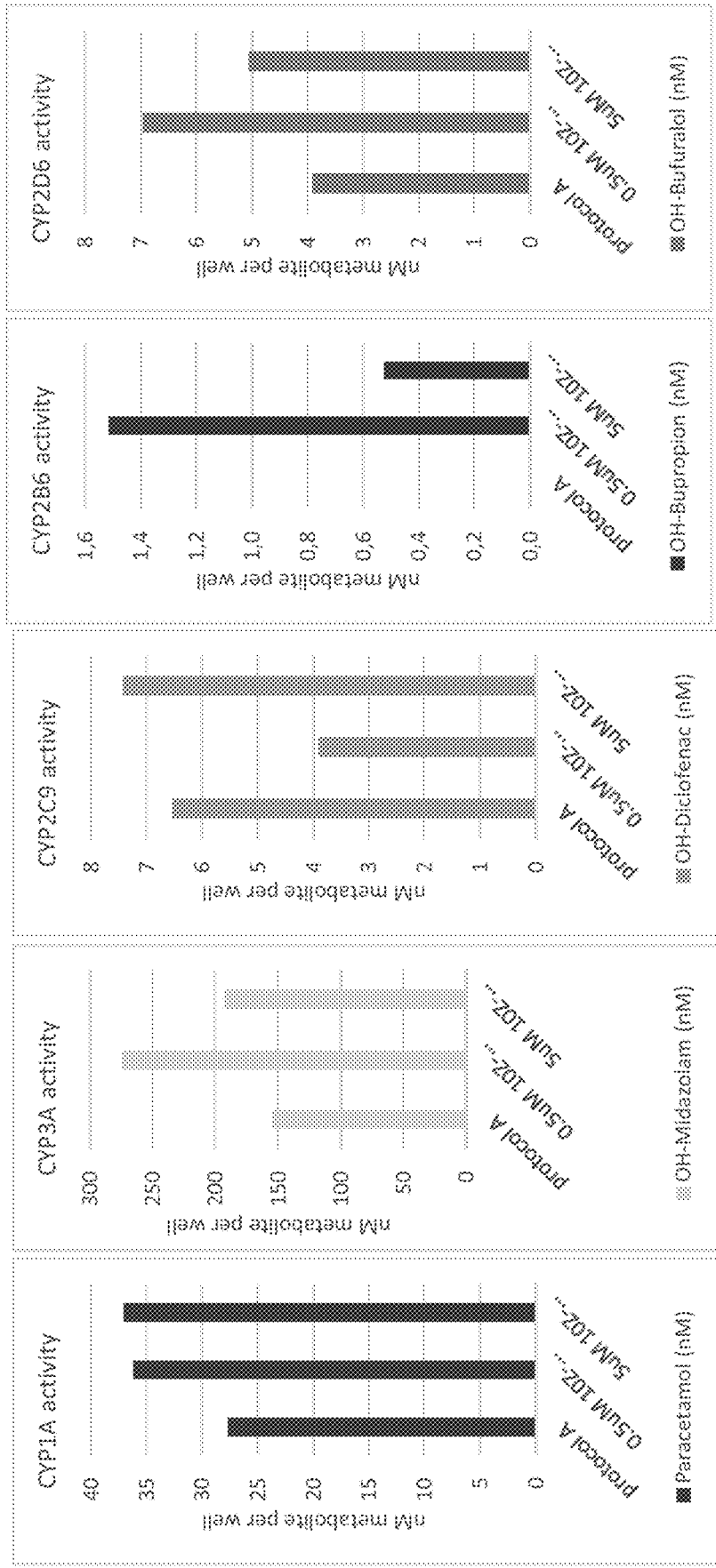
Figure 1C:
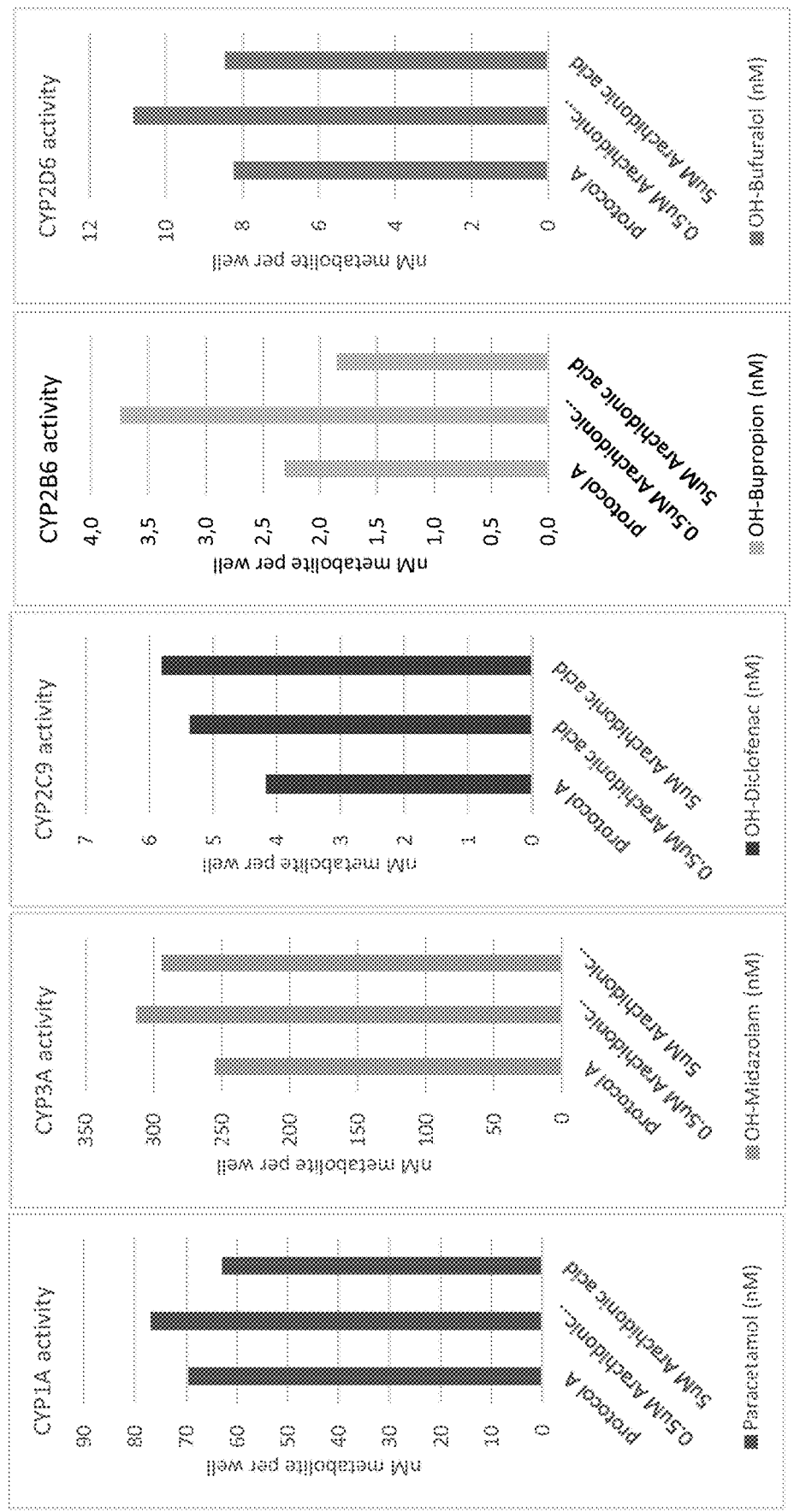
Figure 1D:
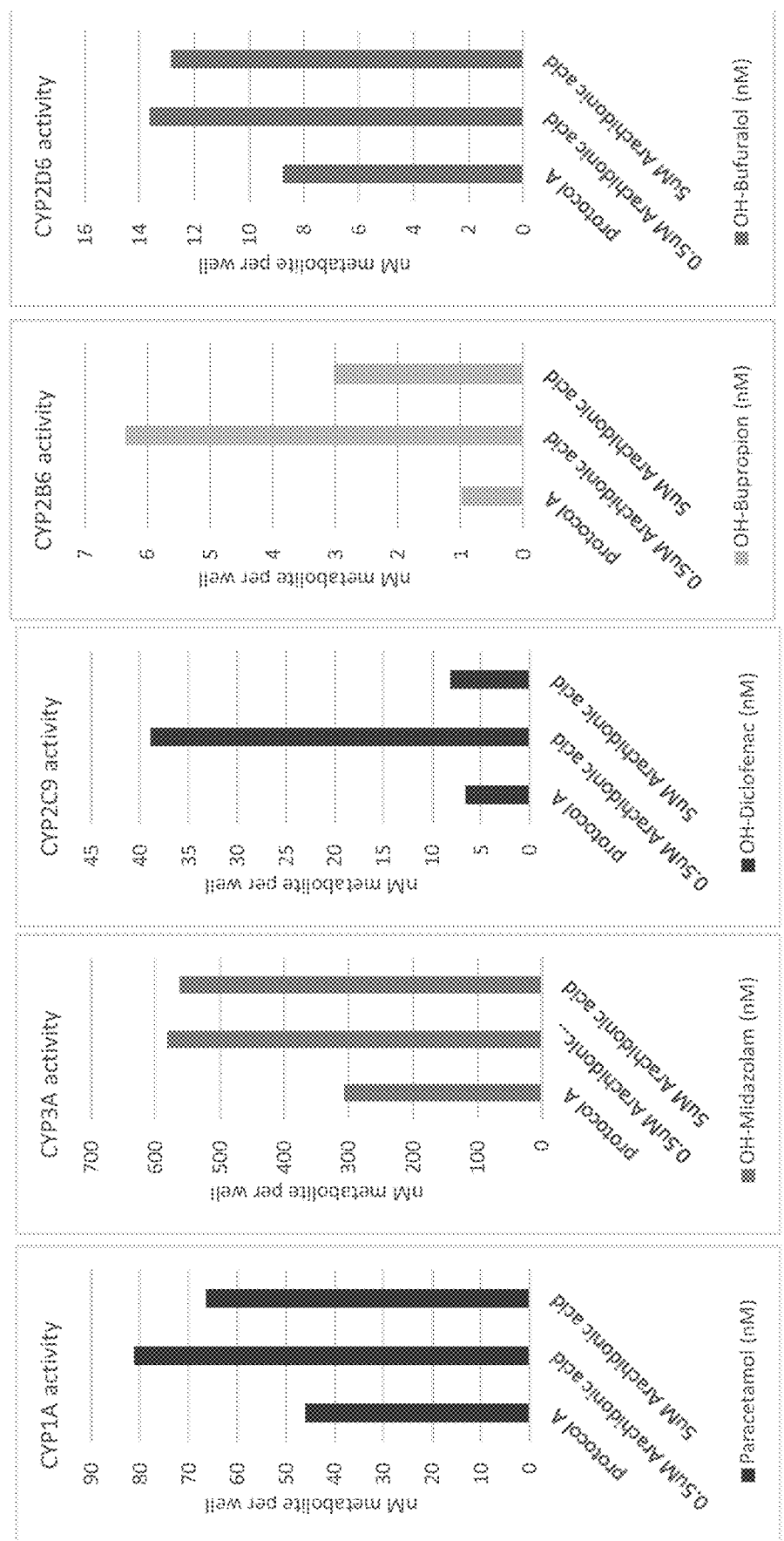
Figure 1E:
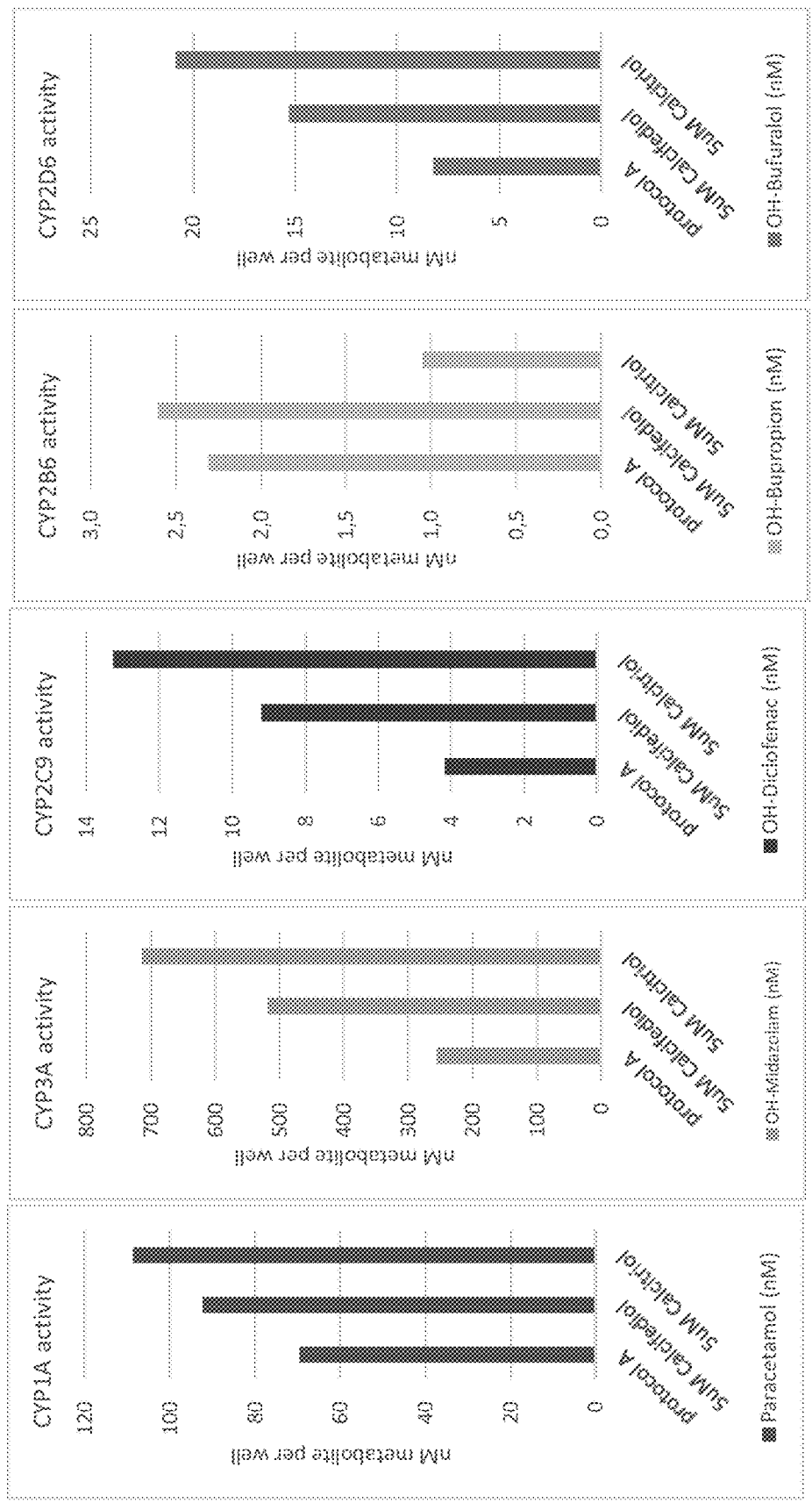
Figure 1F:
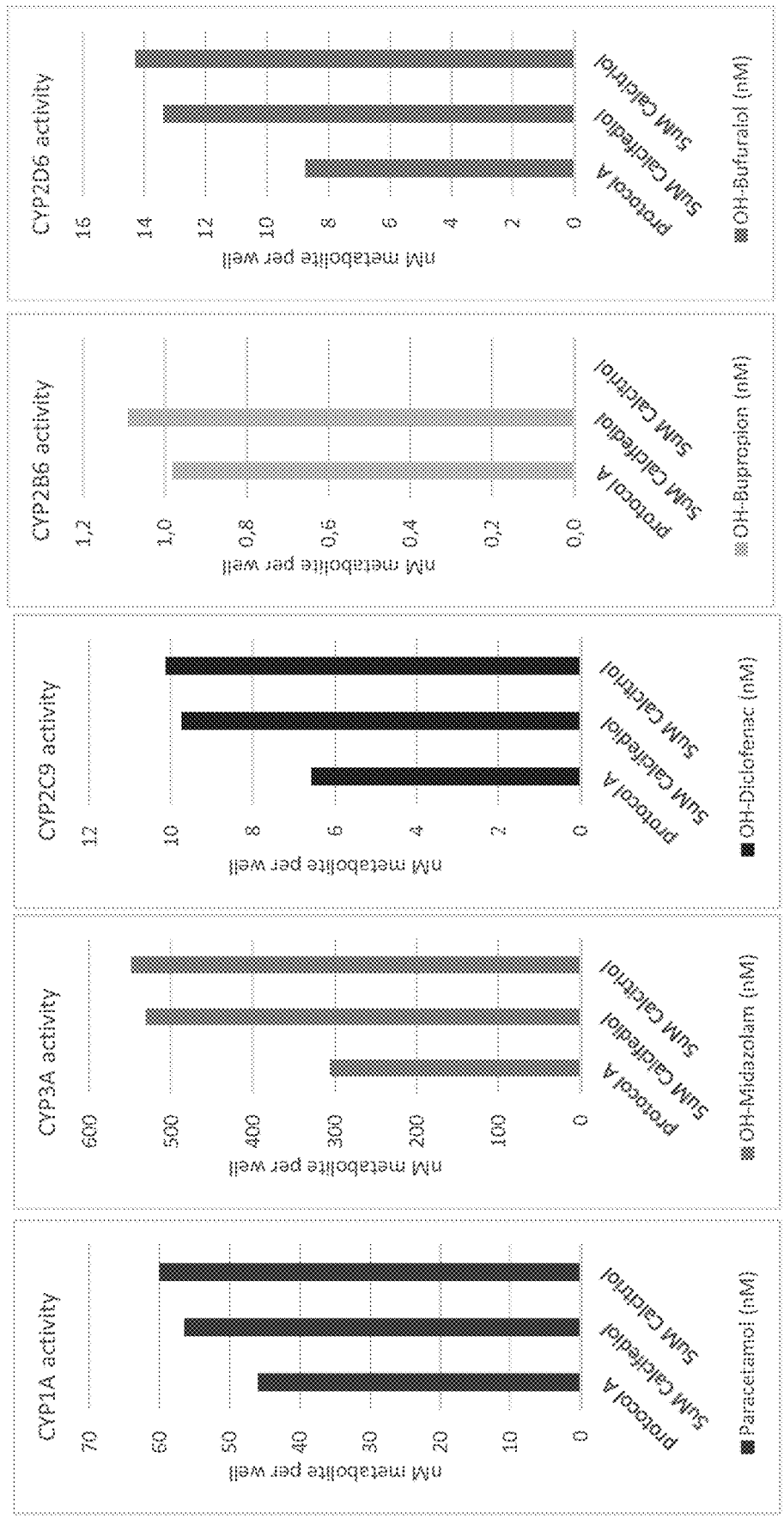
Figure 1G:
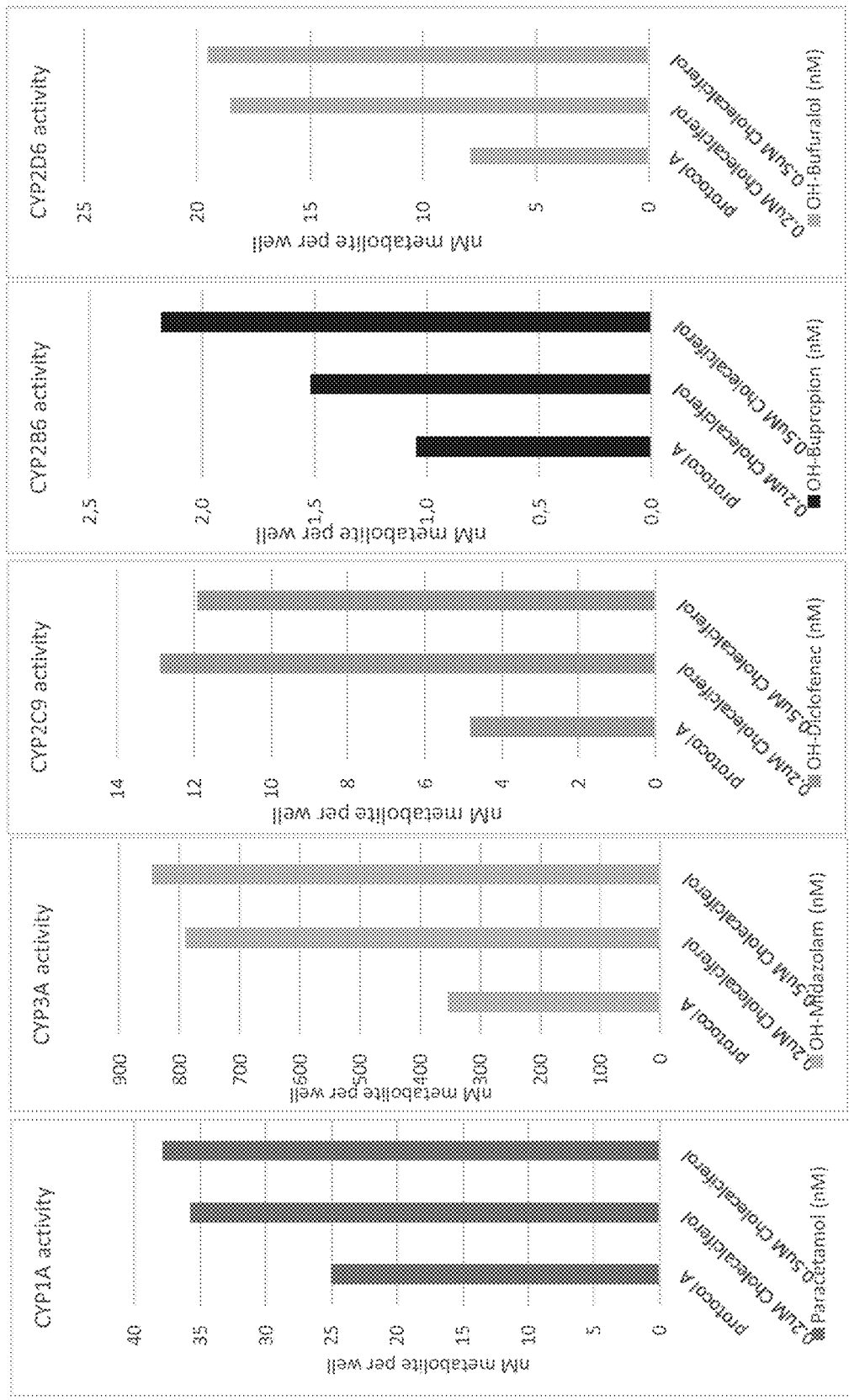
Figure 1H:
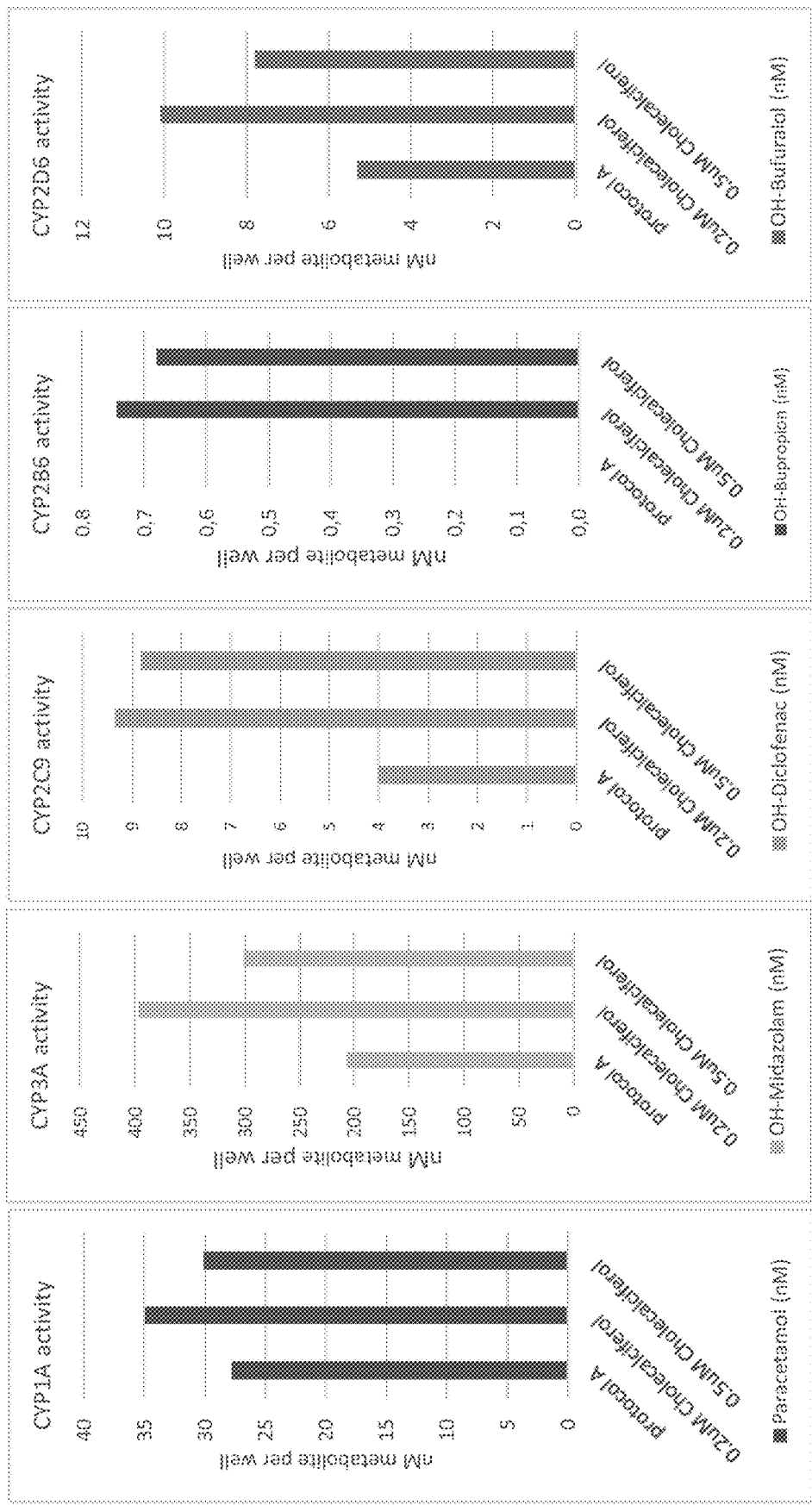
Figure 1I:
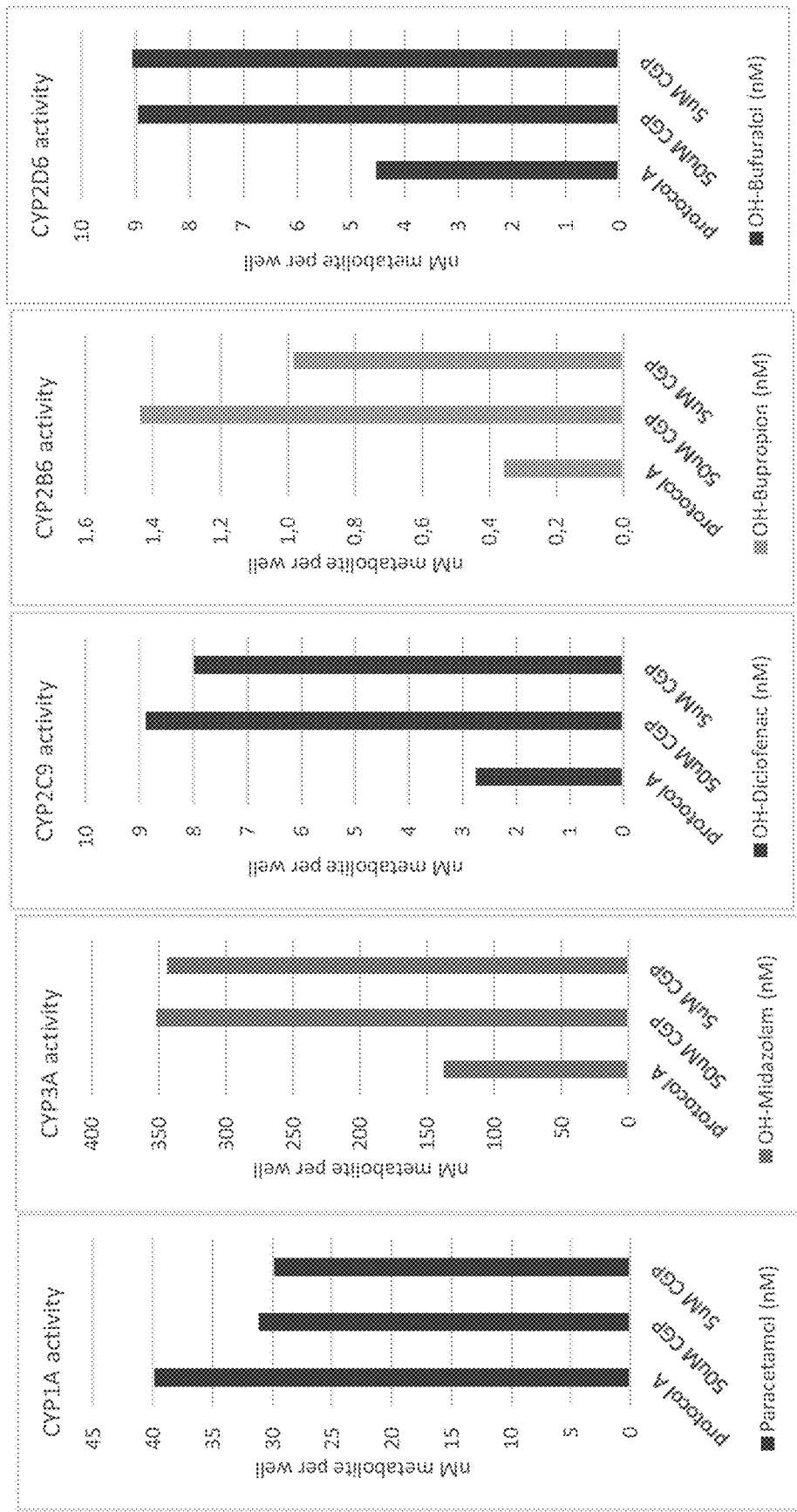
Figure 1J:
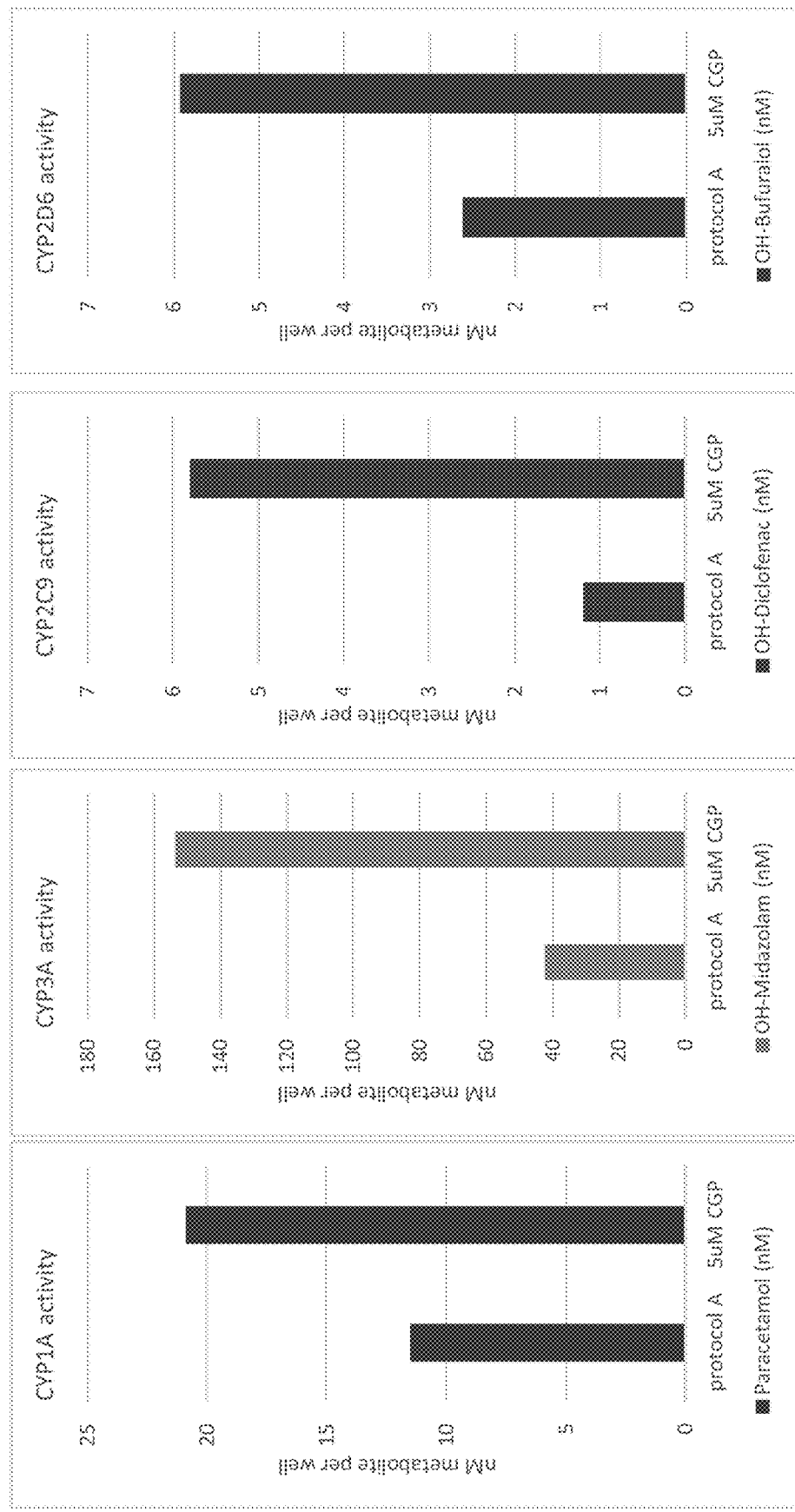
Figure 1K:
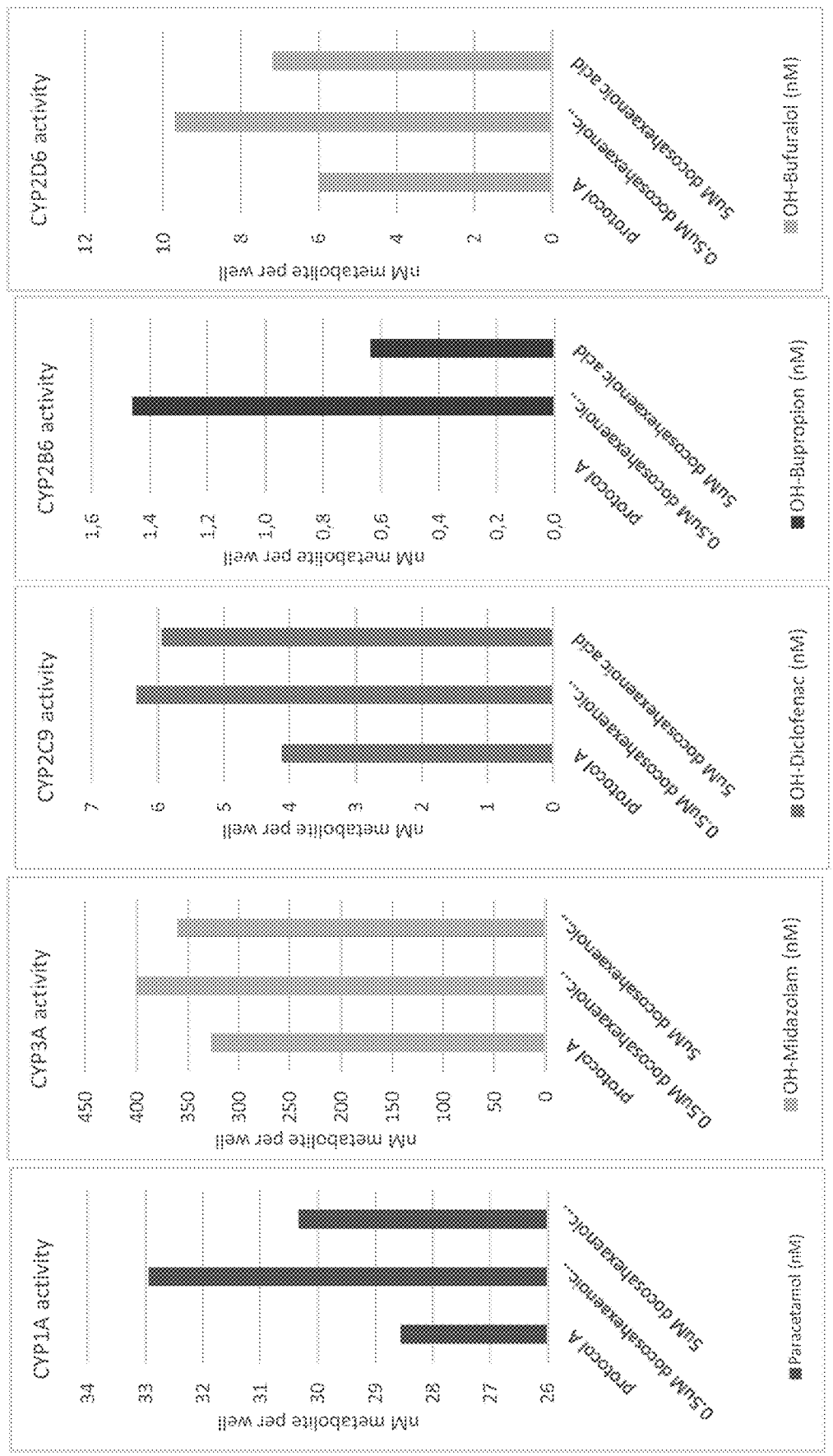
Figure 1L:
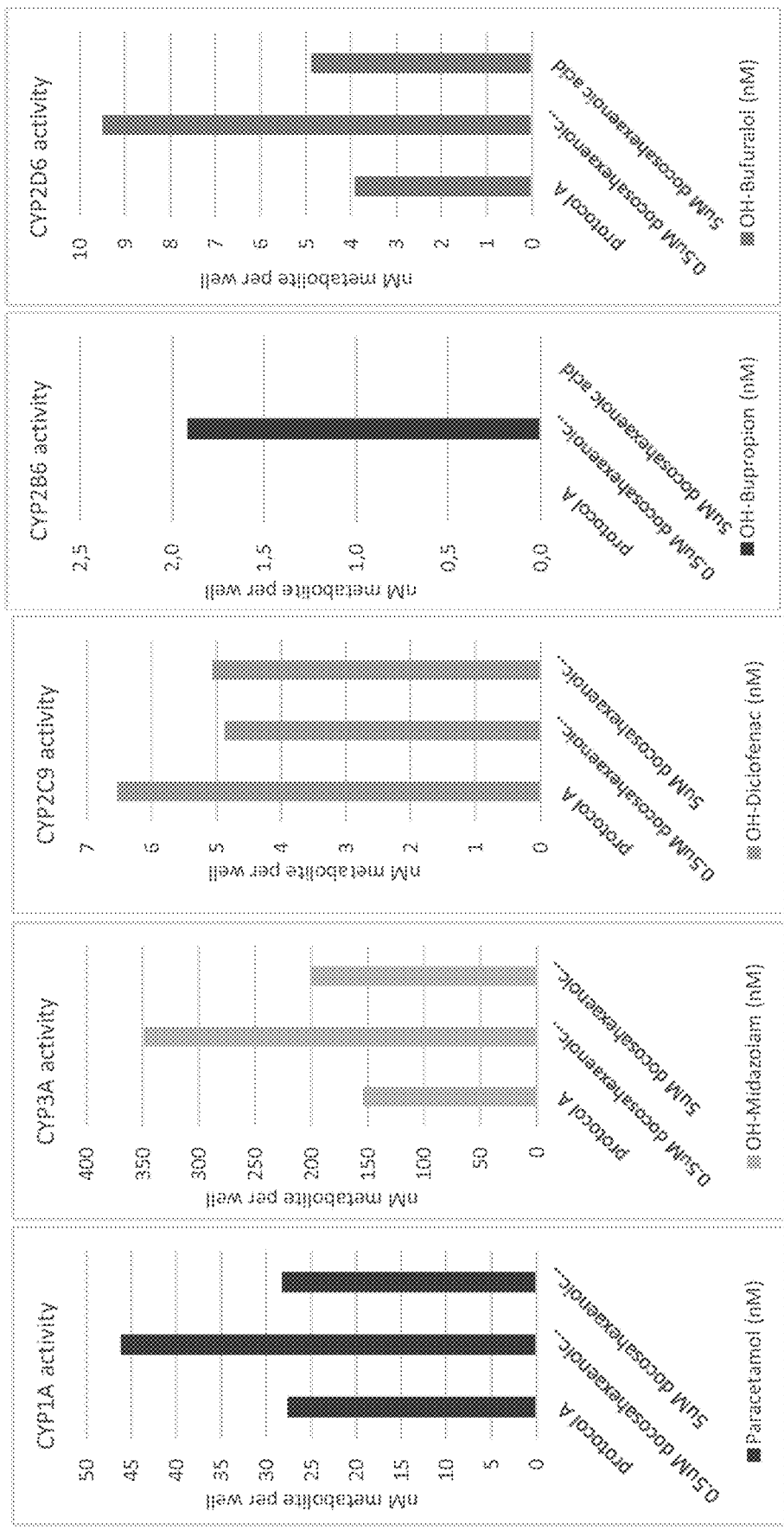
Figure 1M:
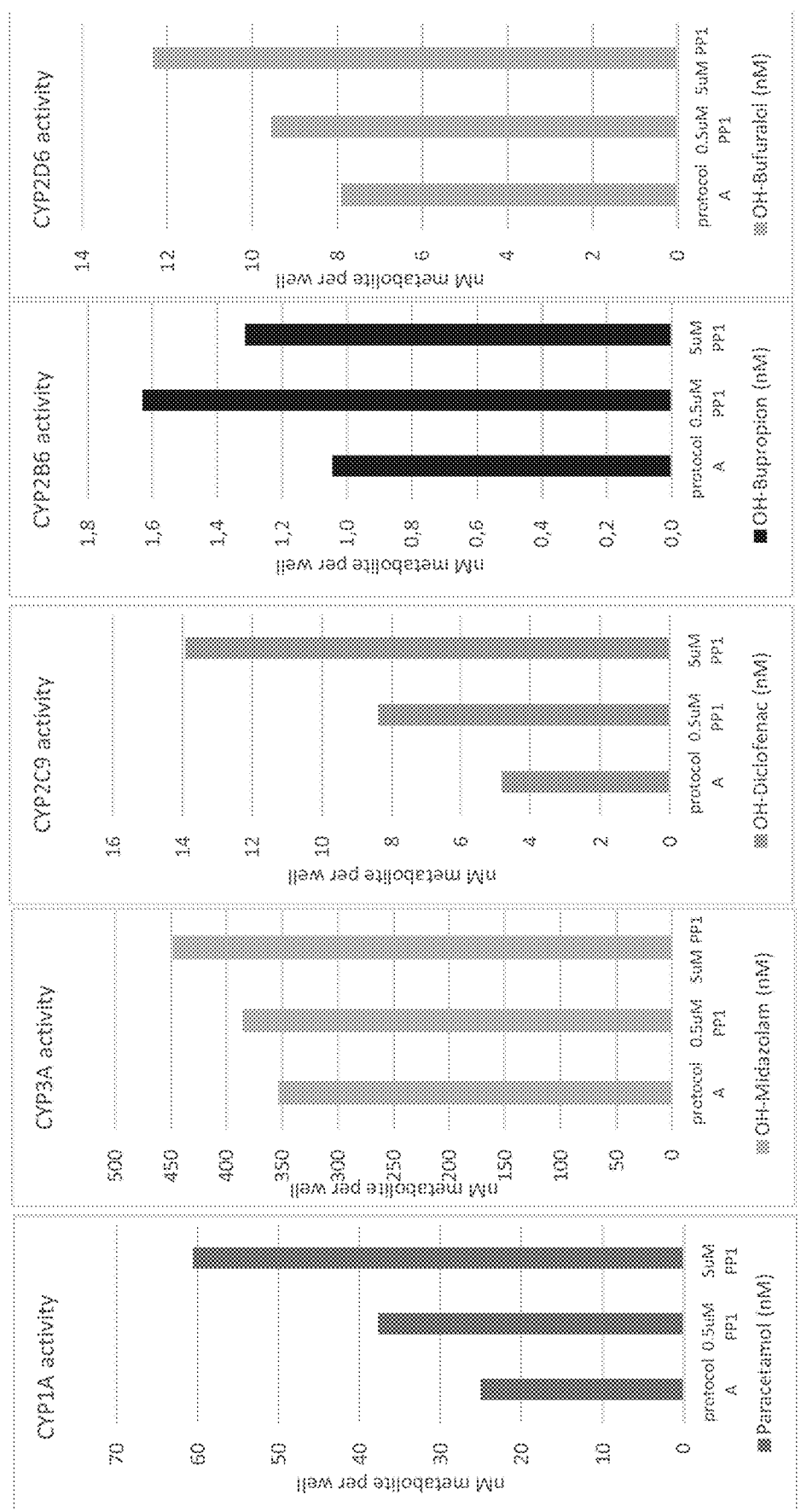
Figure 1N:
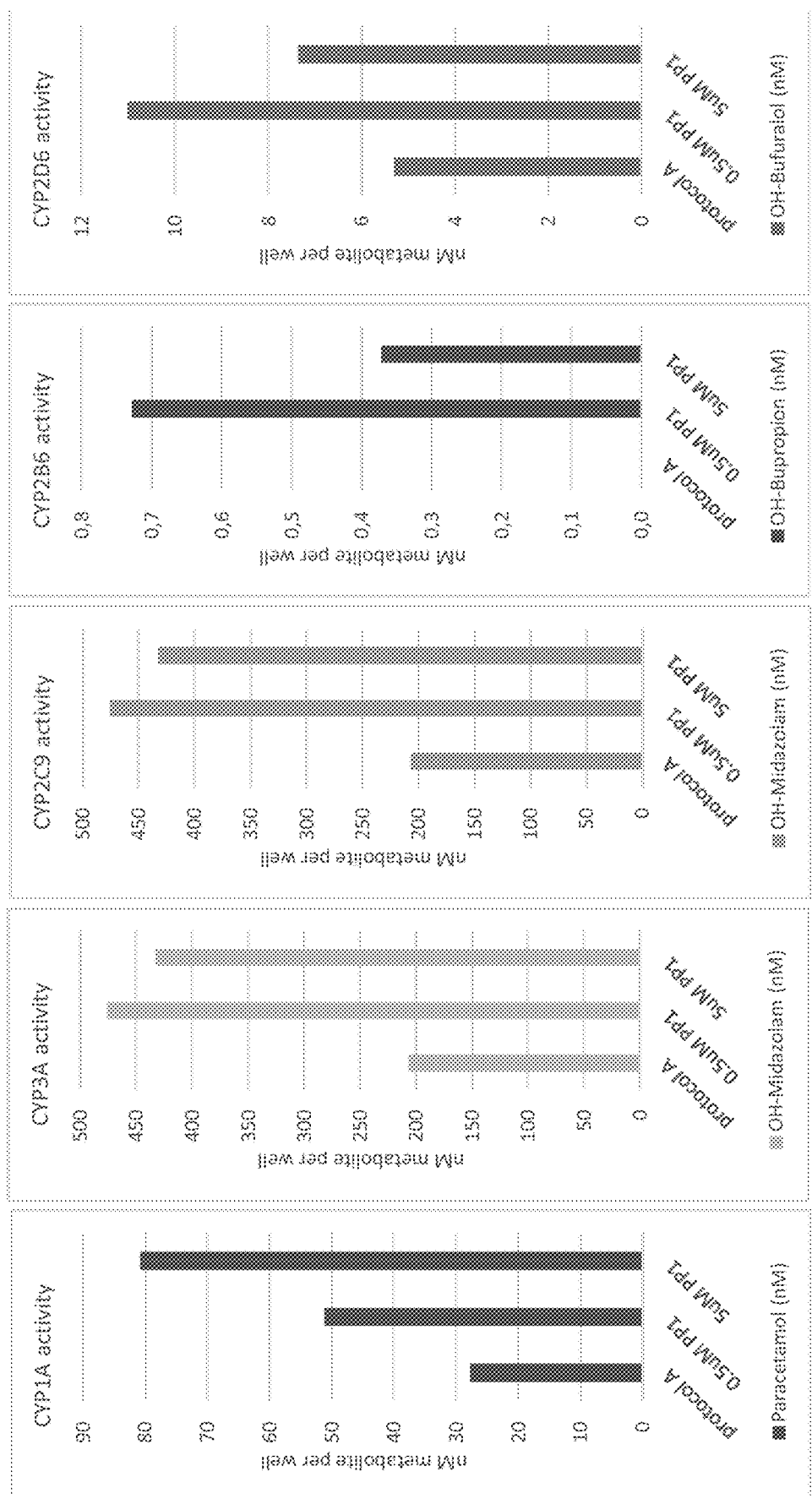
Figure 1O:
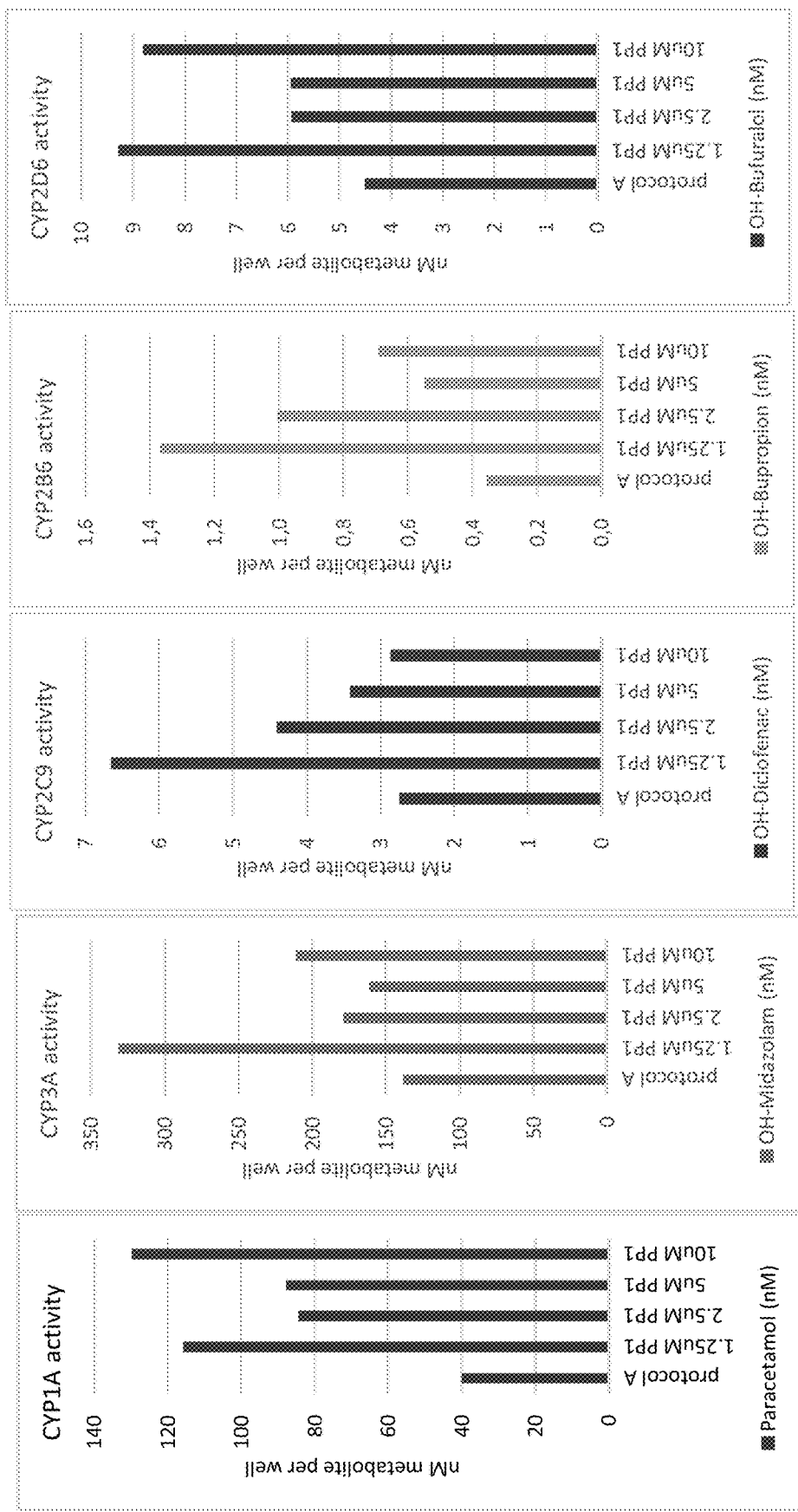
Figure 1P:
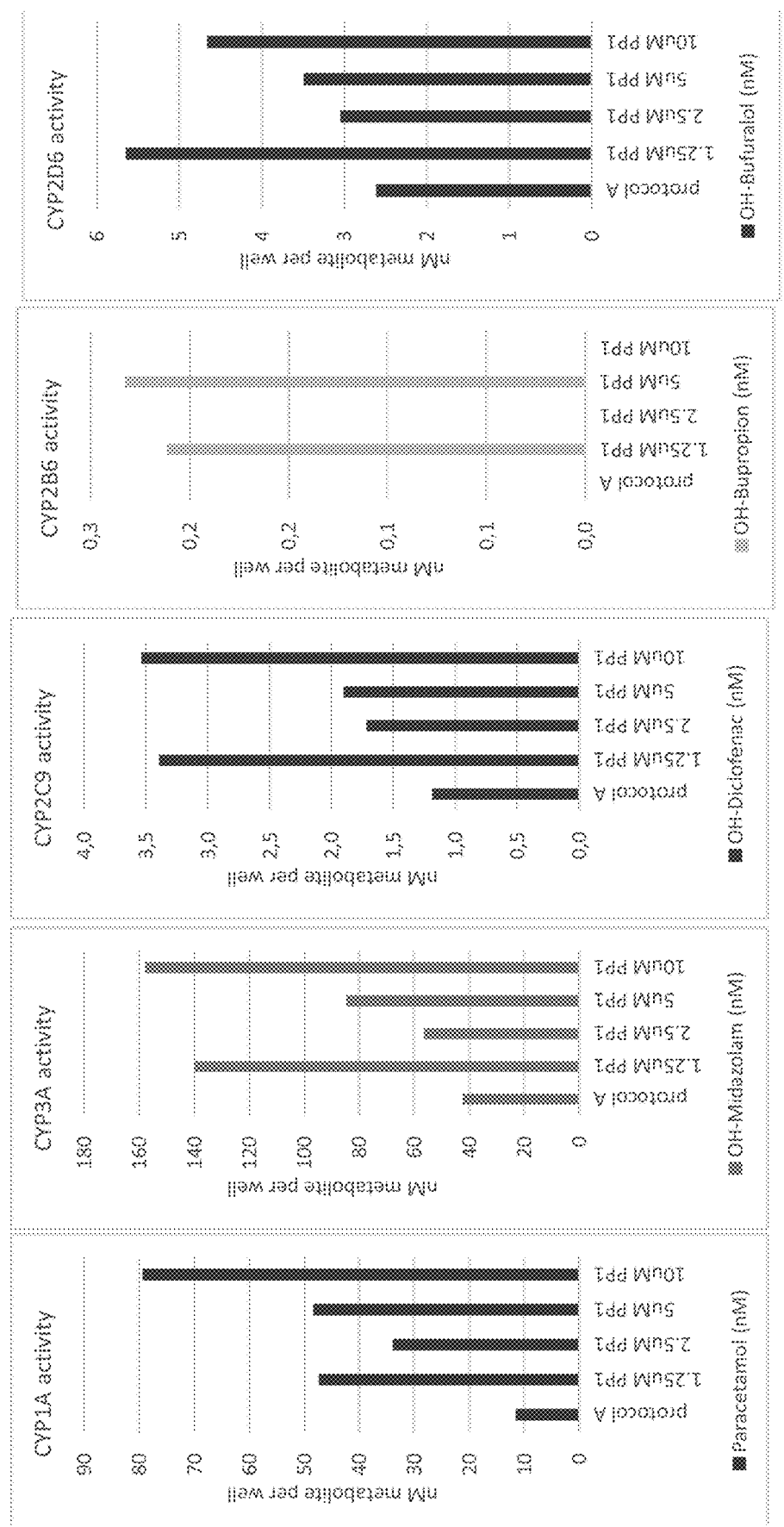
Figure 1Q:
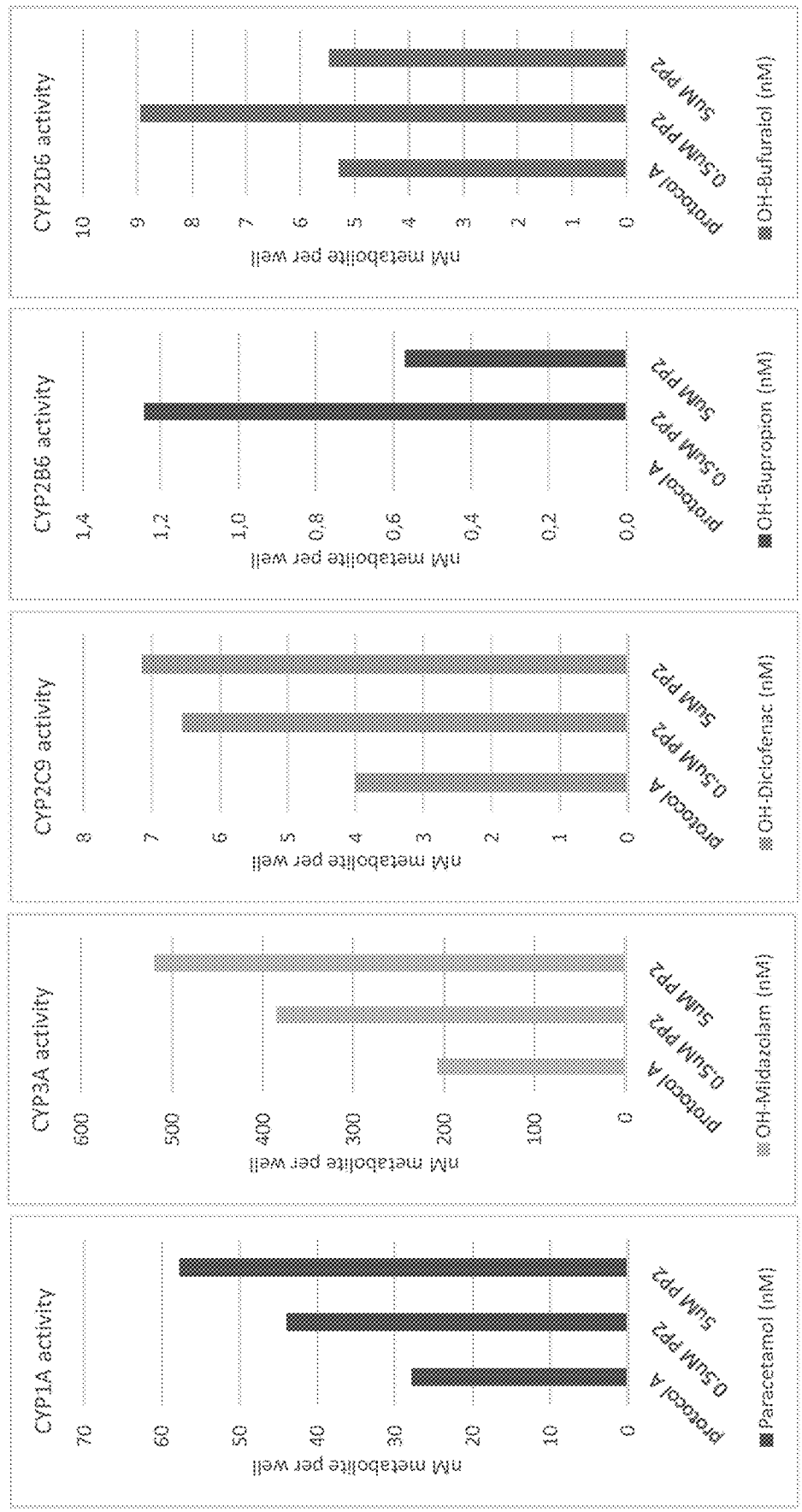
Figure 1R:
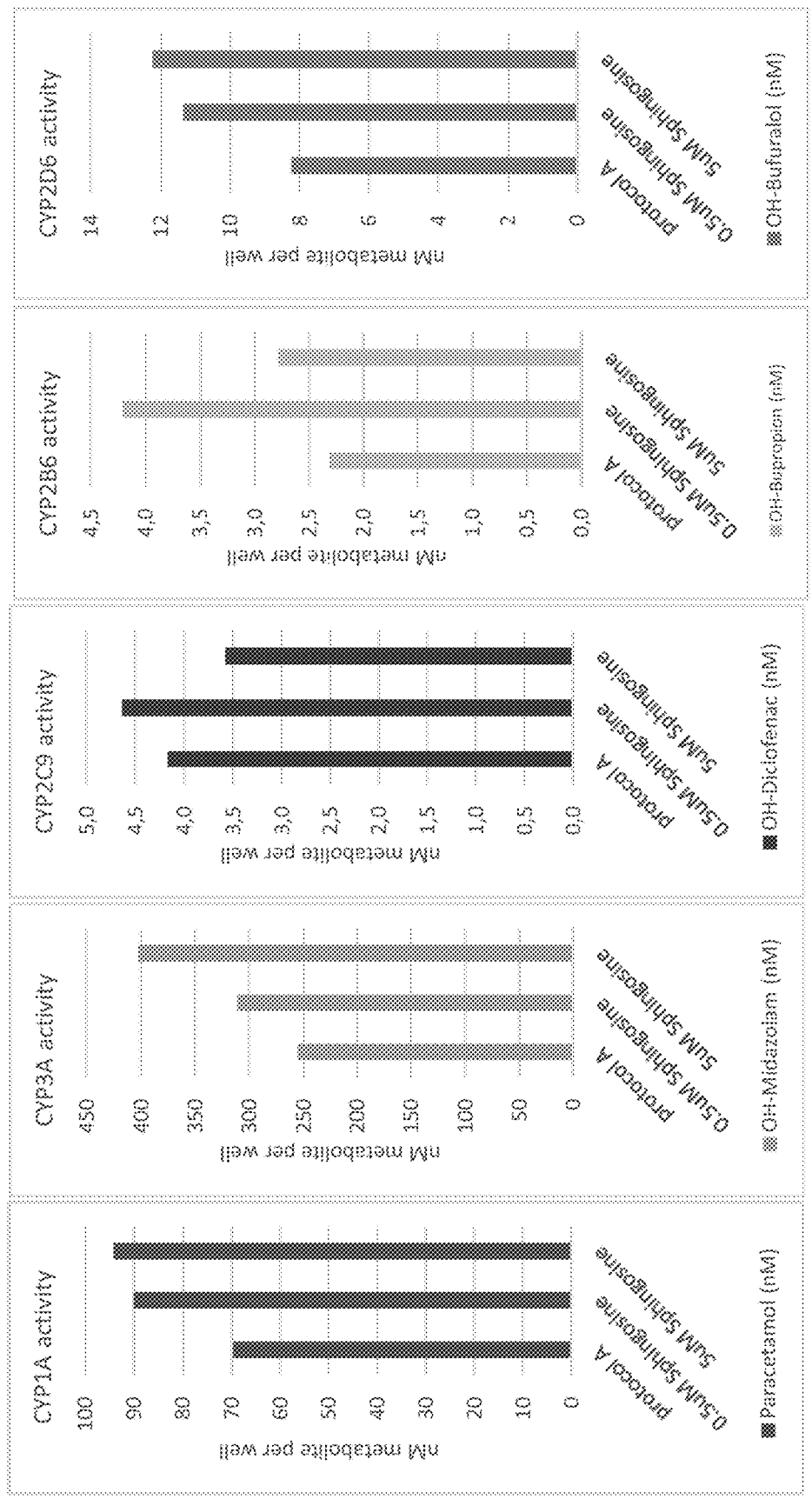
Figure 1S:
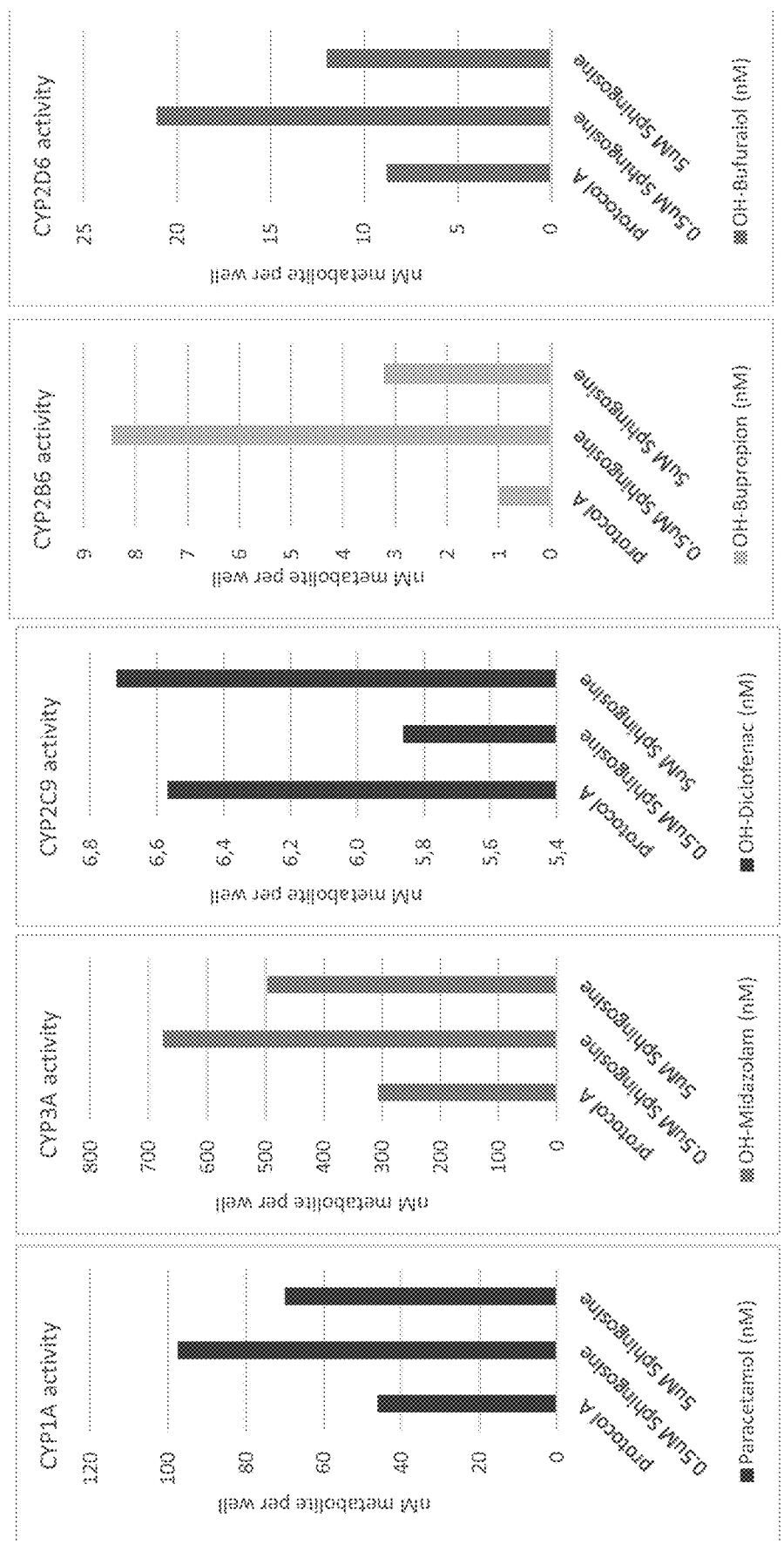
Figure 1T:
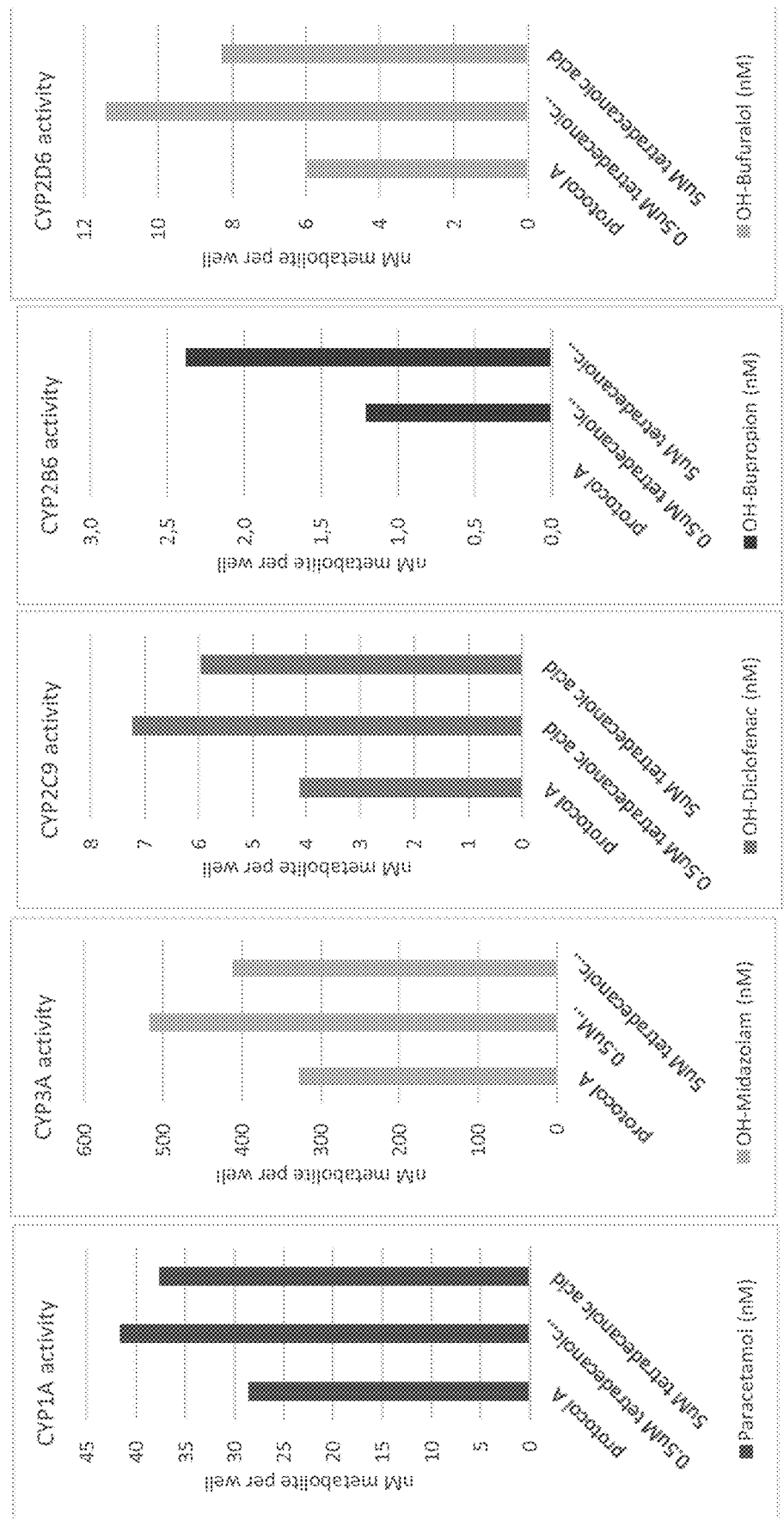
Figure 1U:
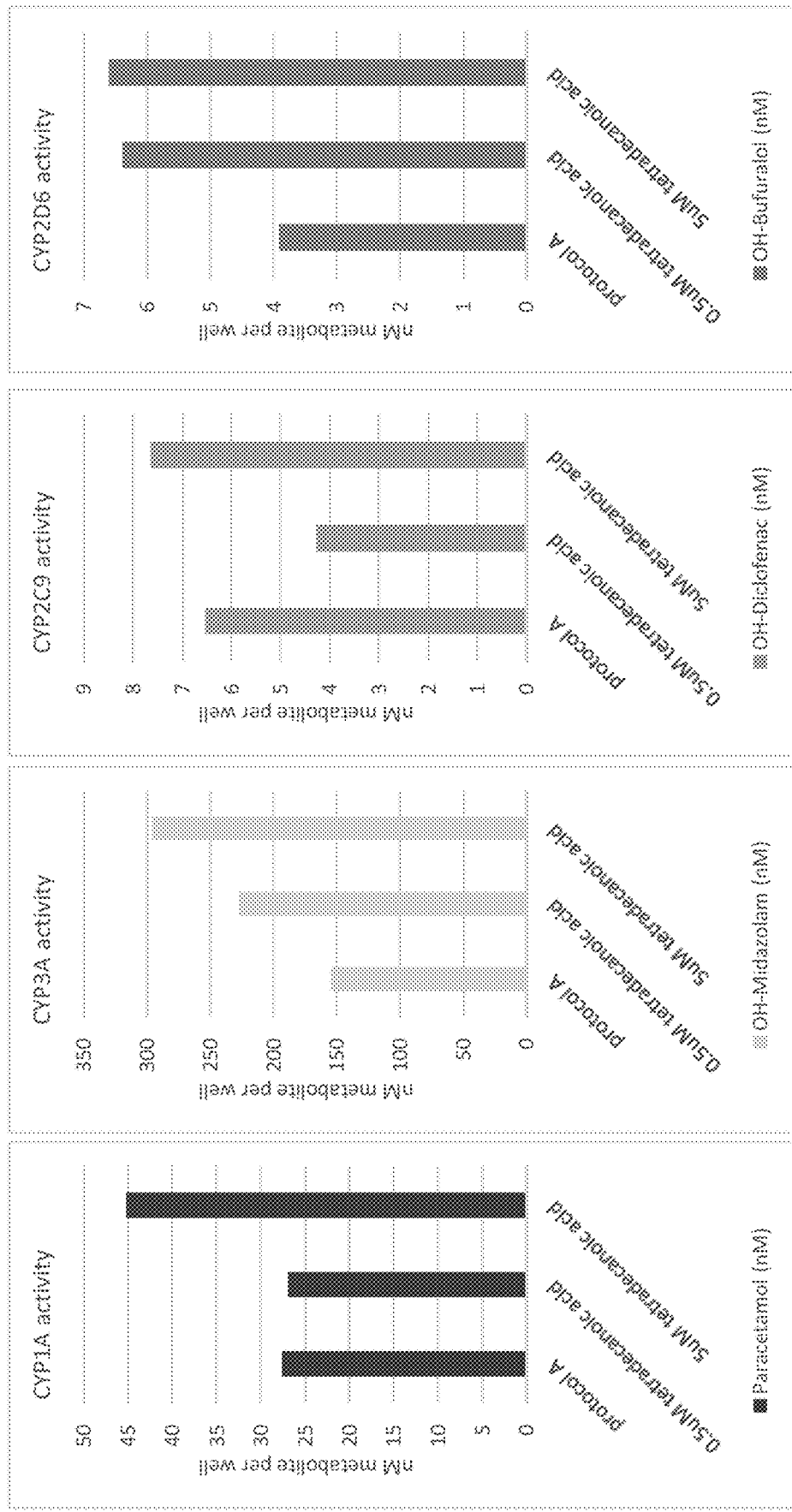
Figure 2A:
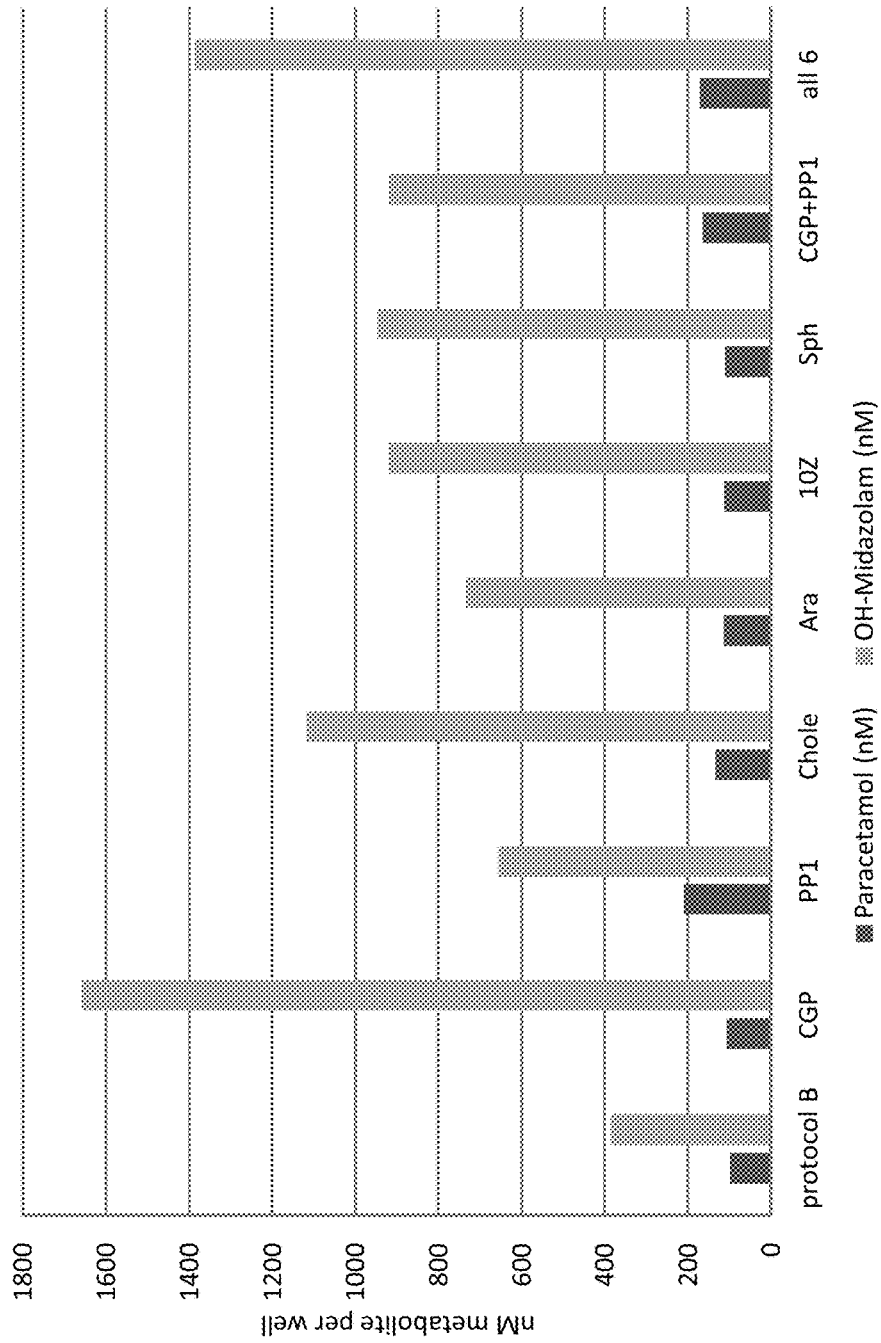
Figure 2B:
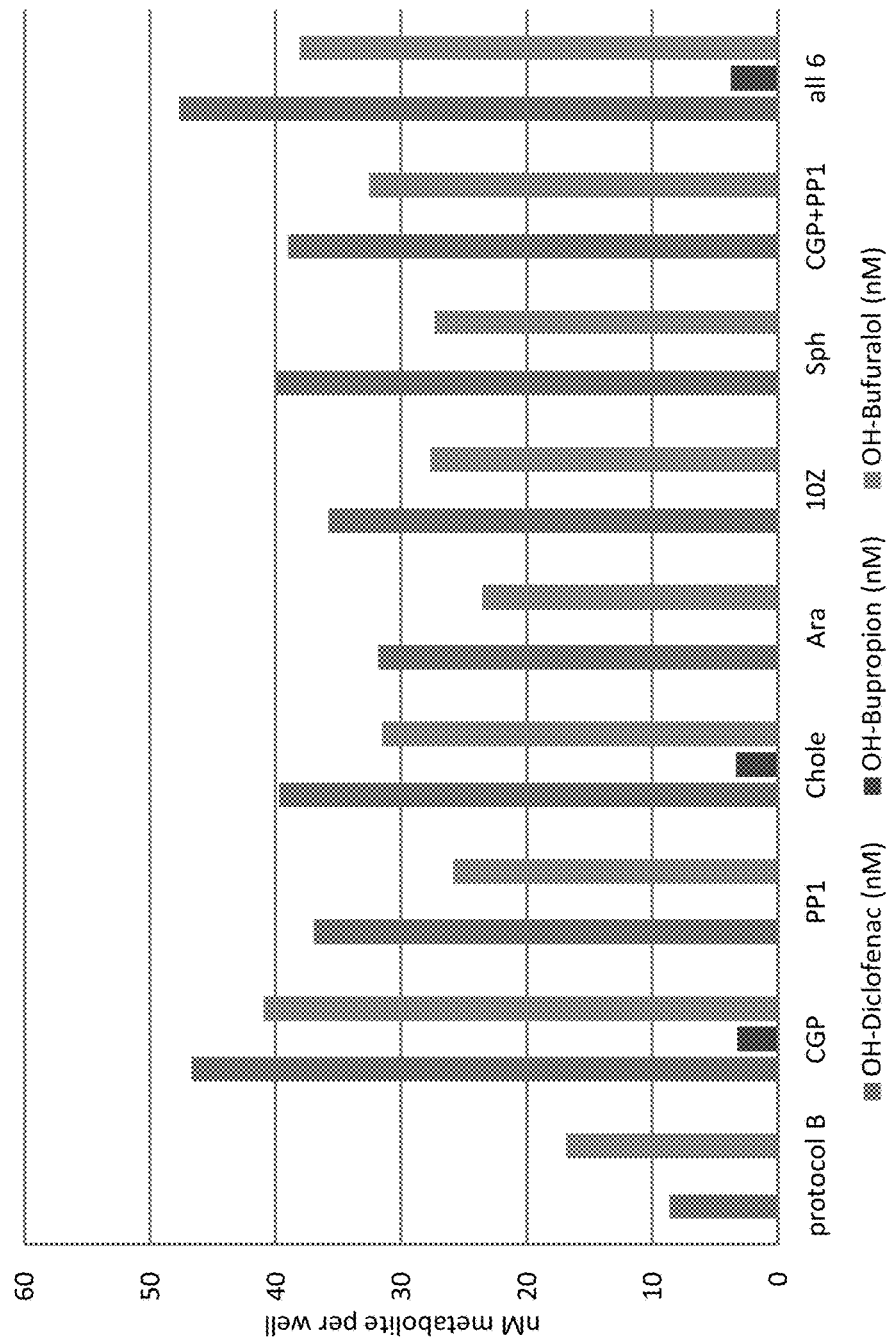
Figure 2D:
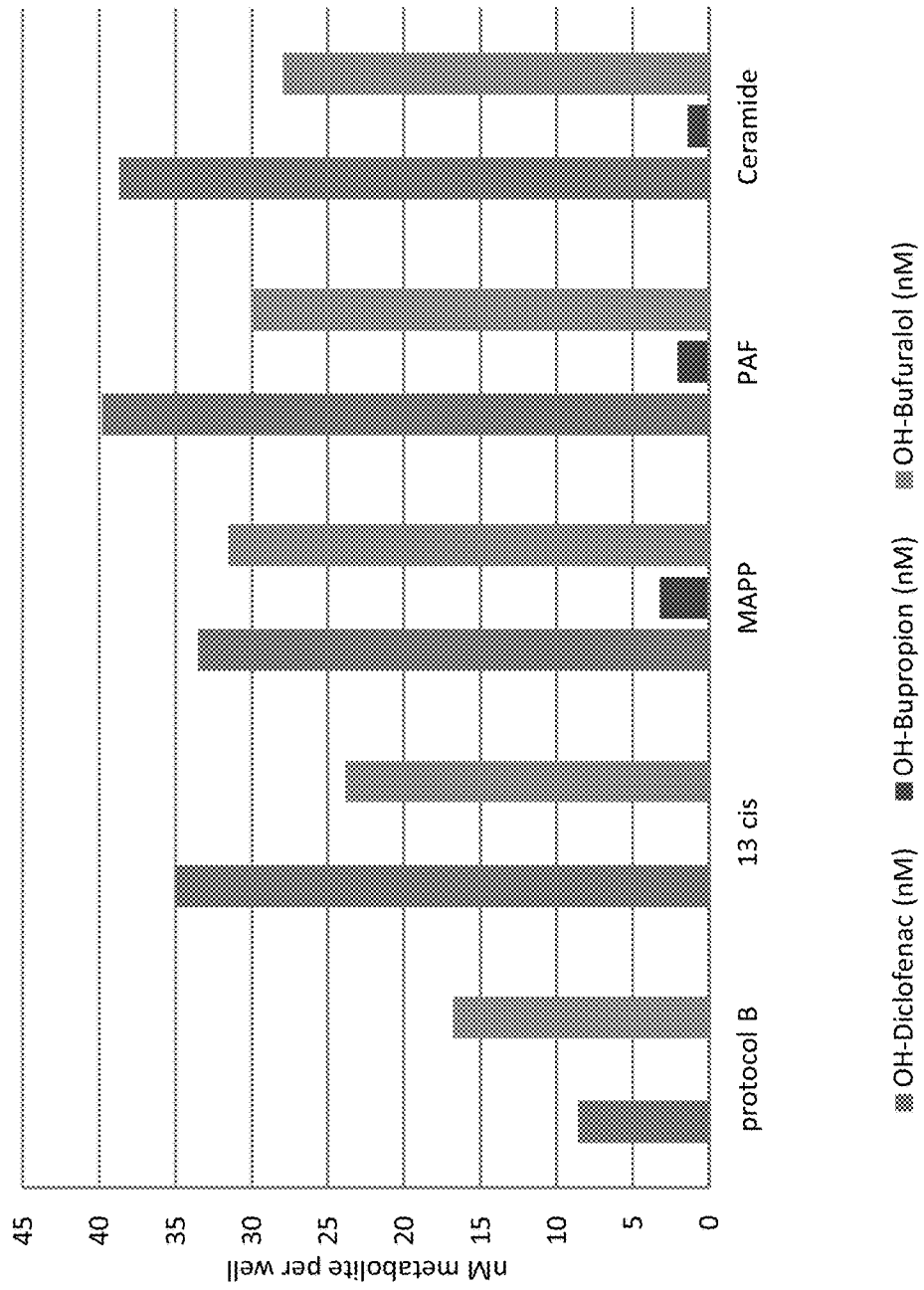
Figure 2E:
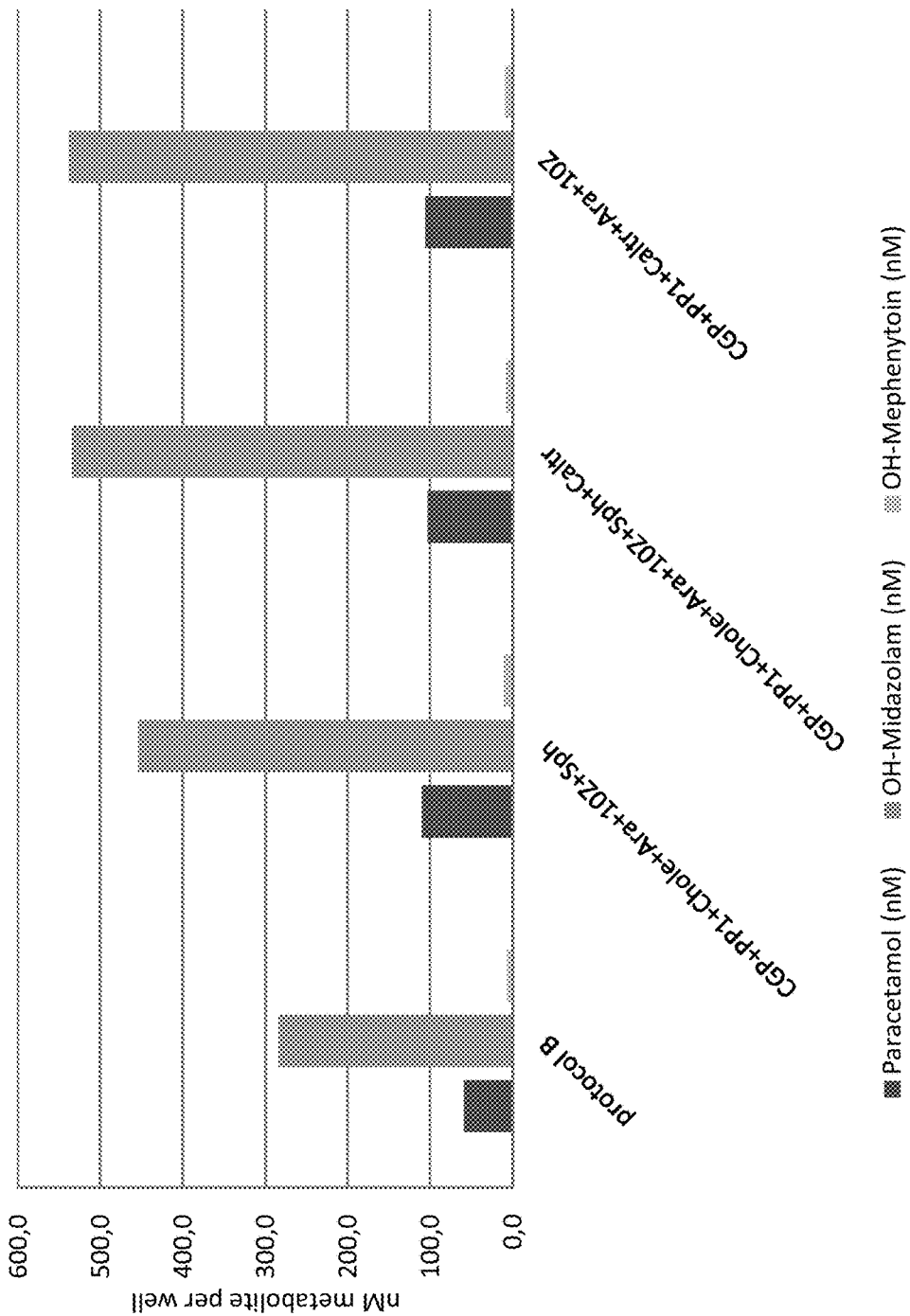
Figure 2F:
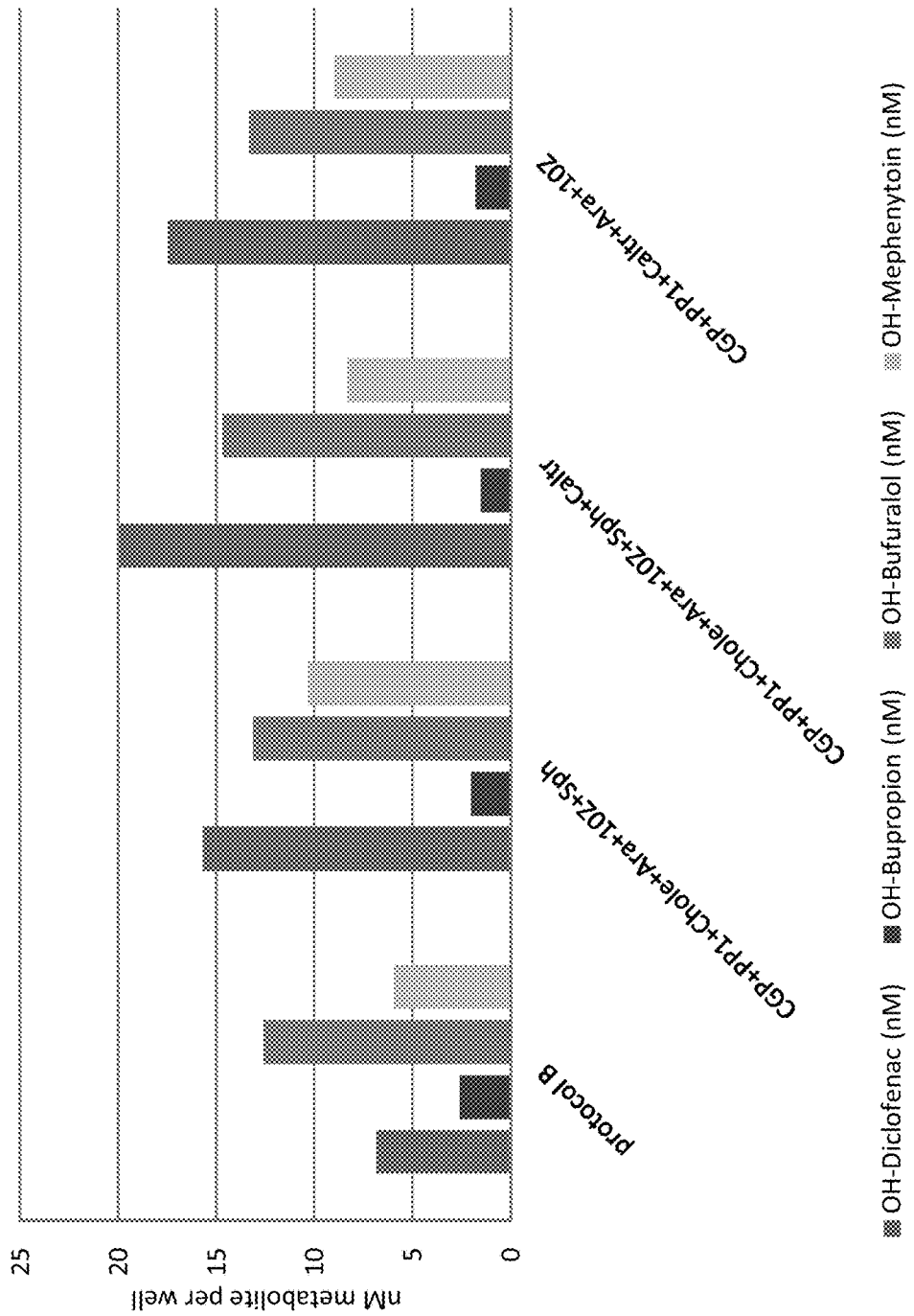
Figure 2G:
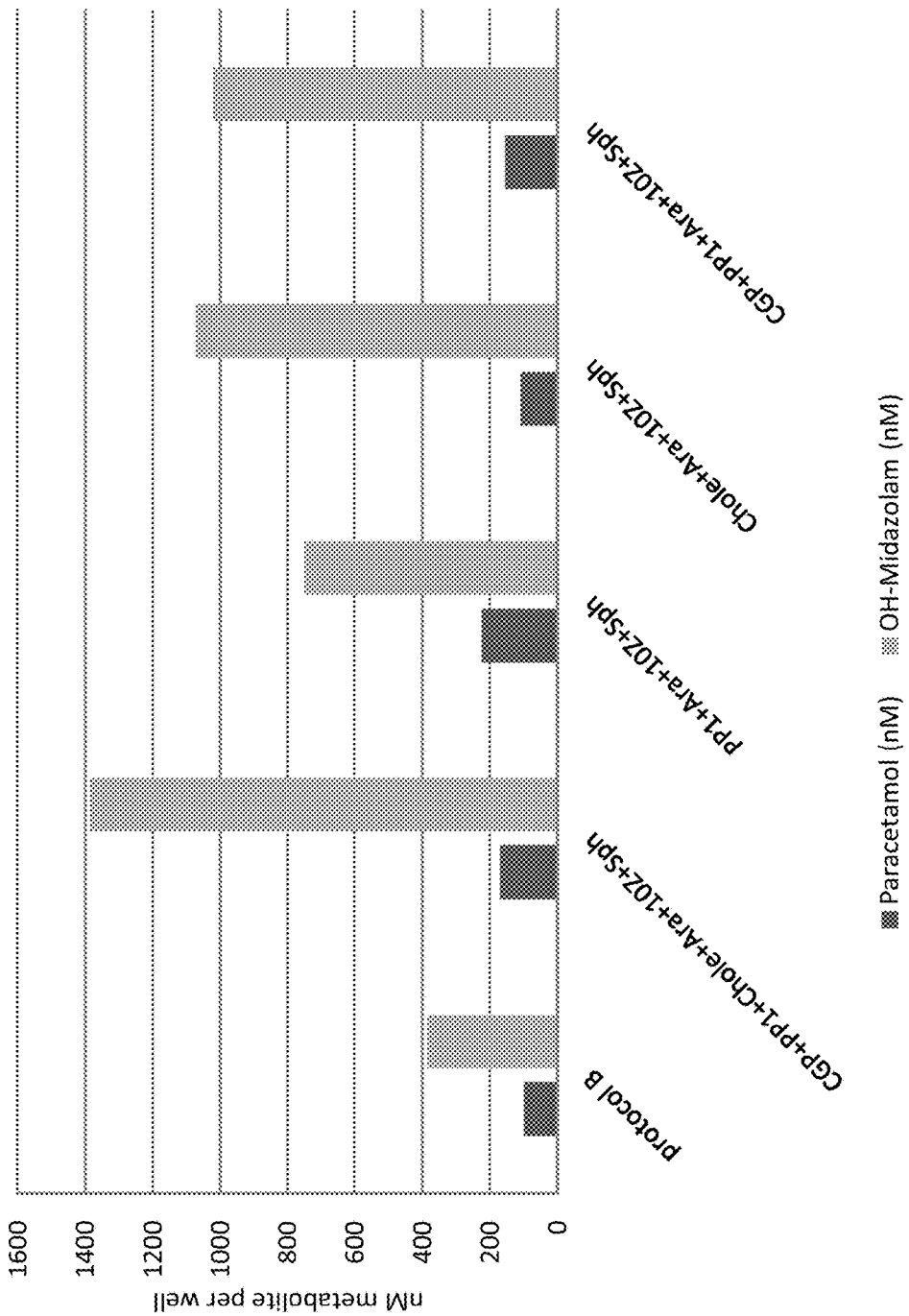
Figure 21:
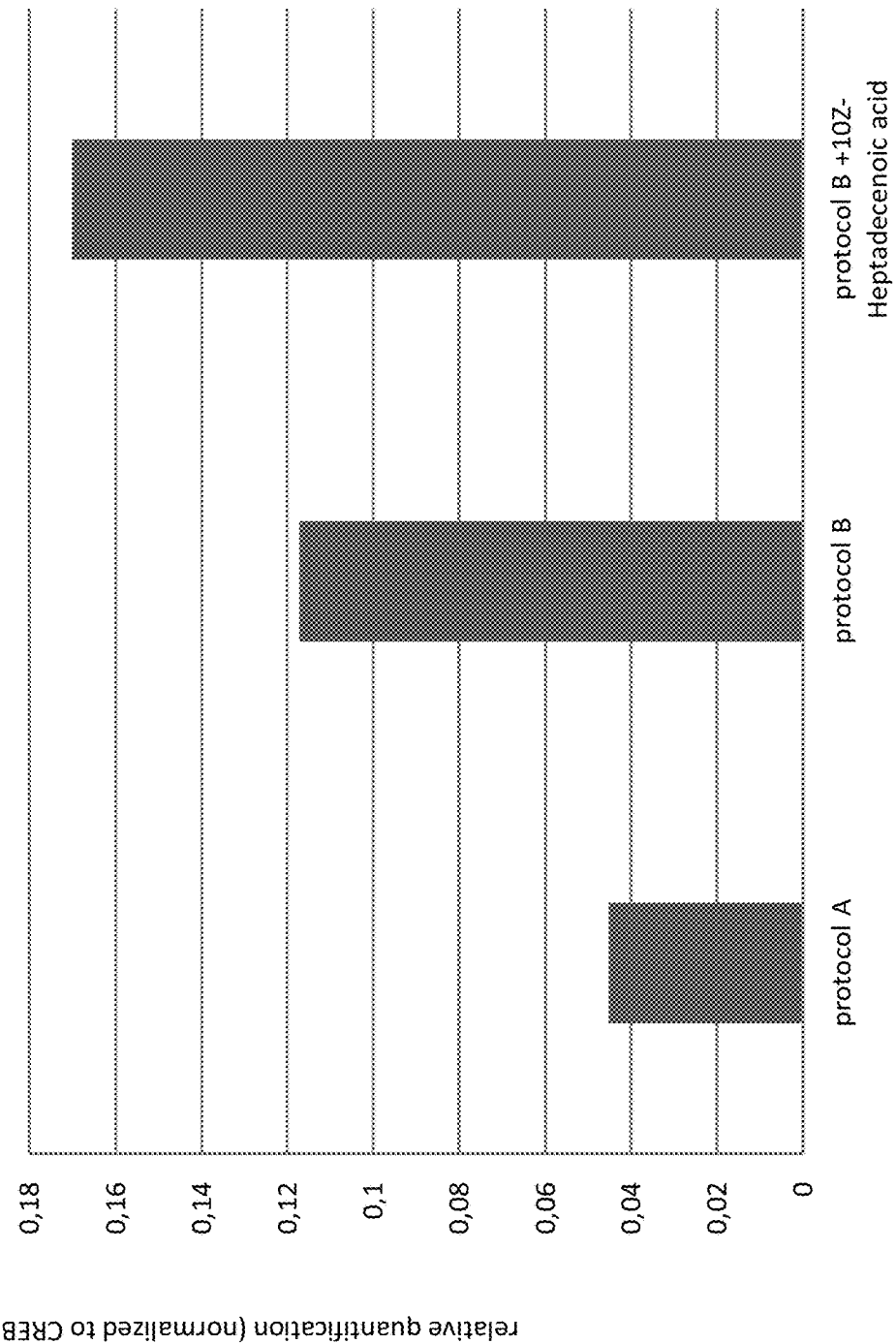
Figure 2K:
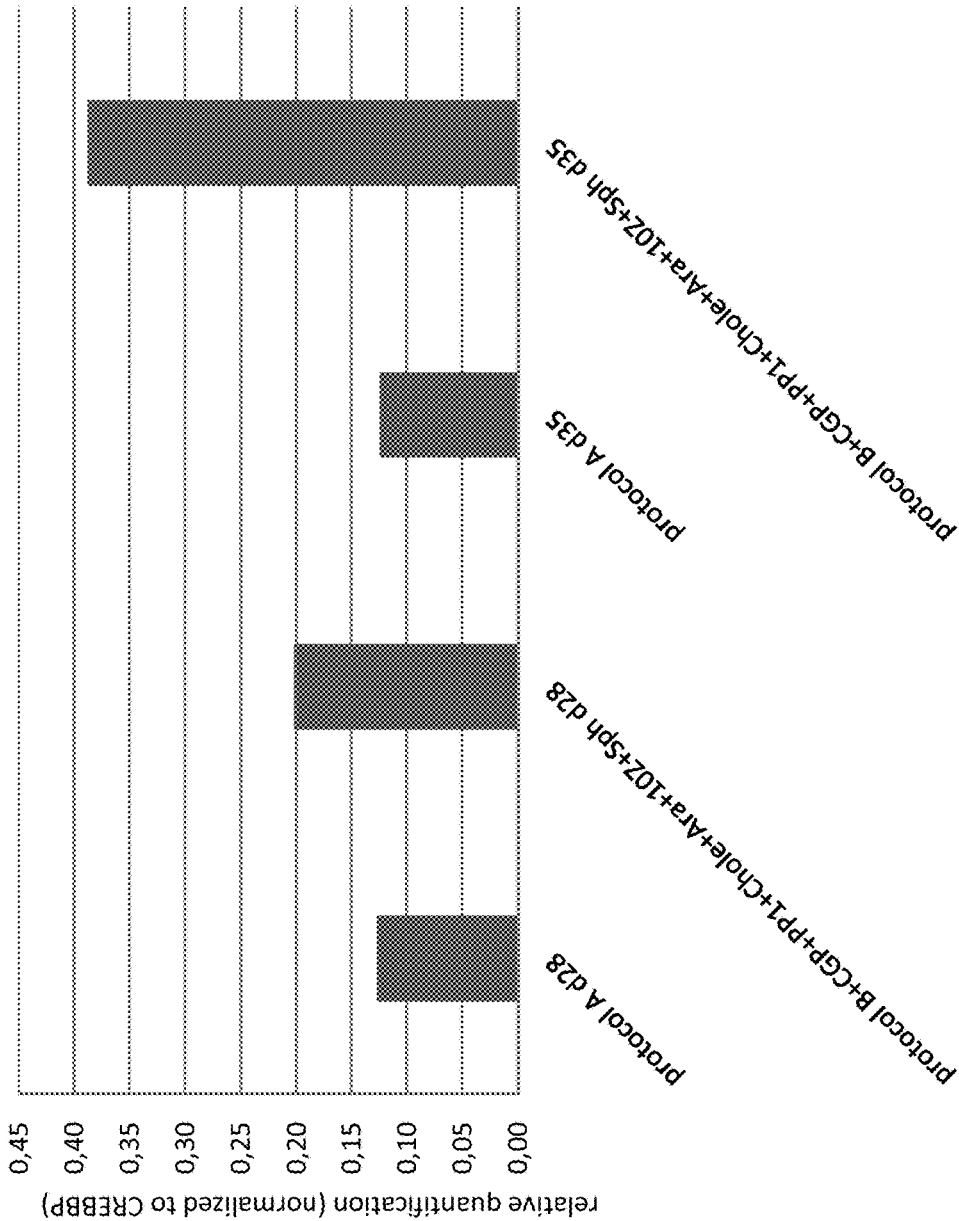
Figure 3A:
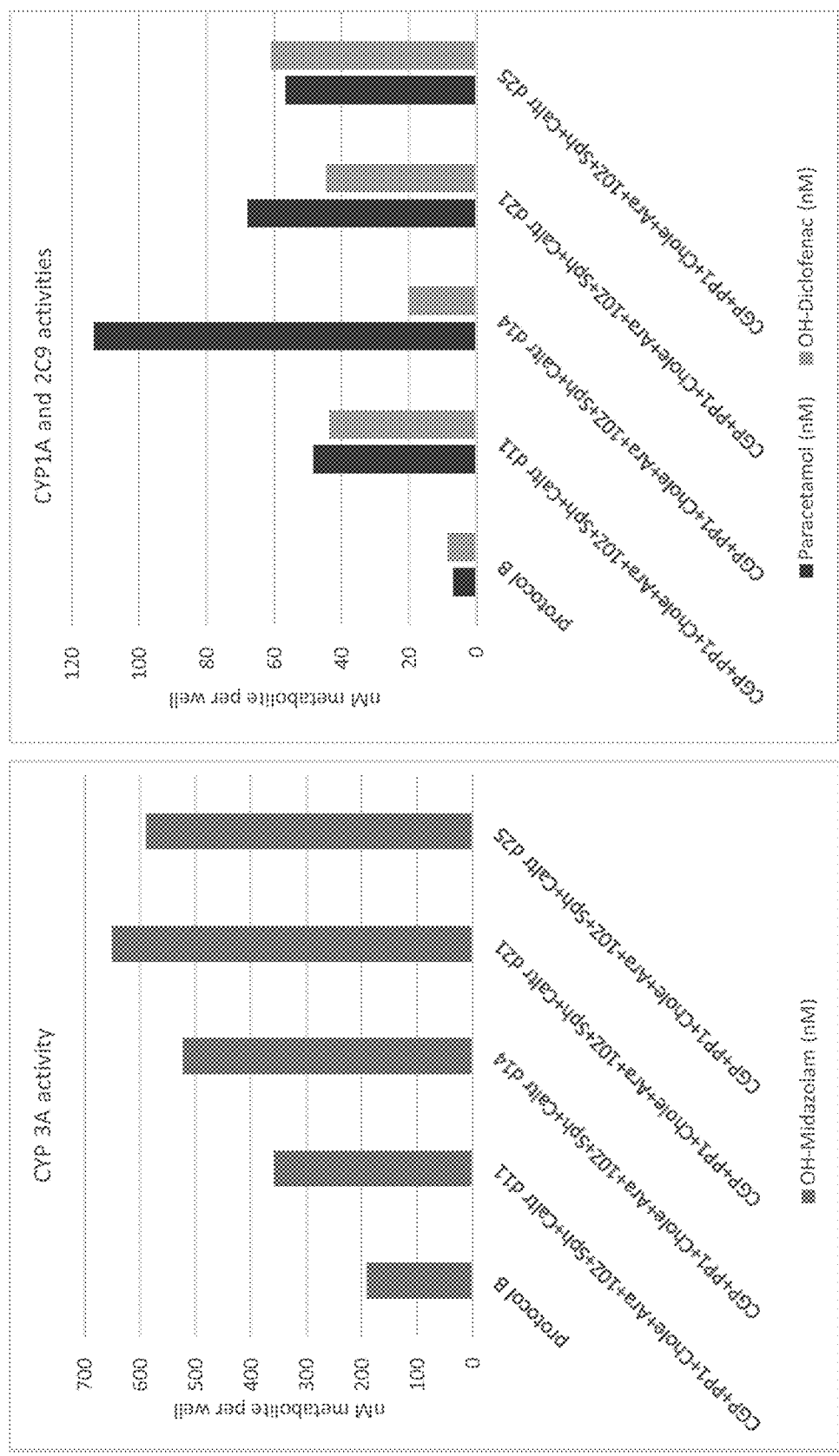
Figure 3B:
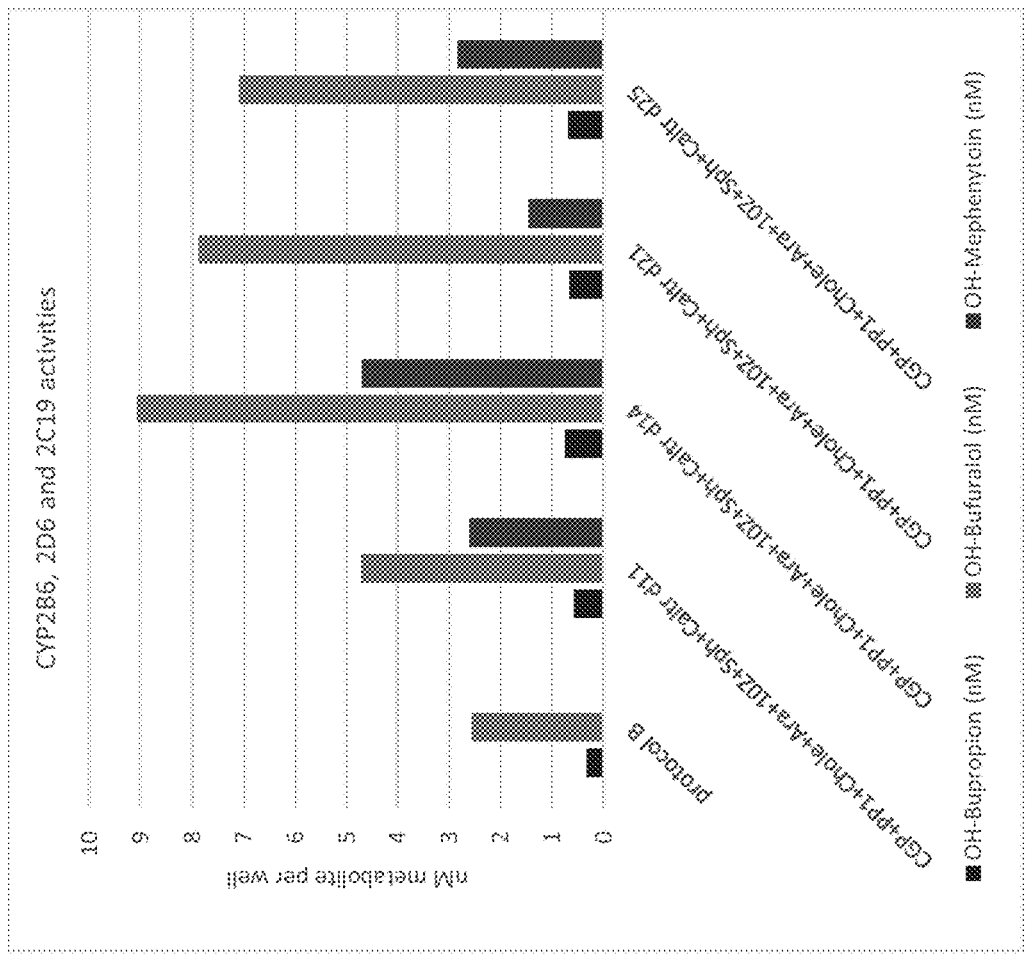
Figure 3C:
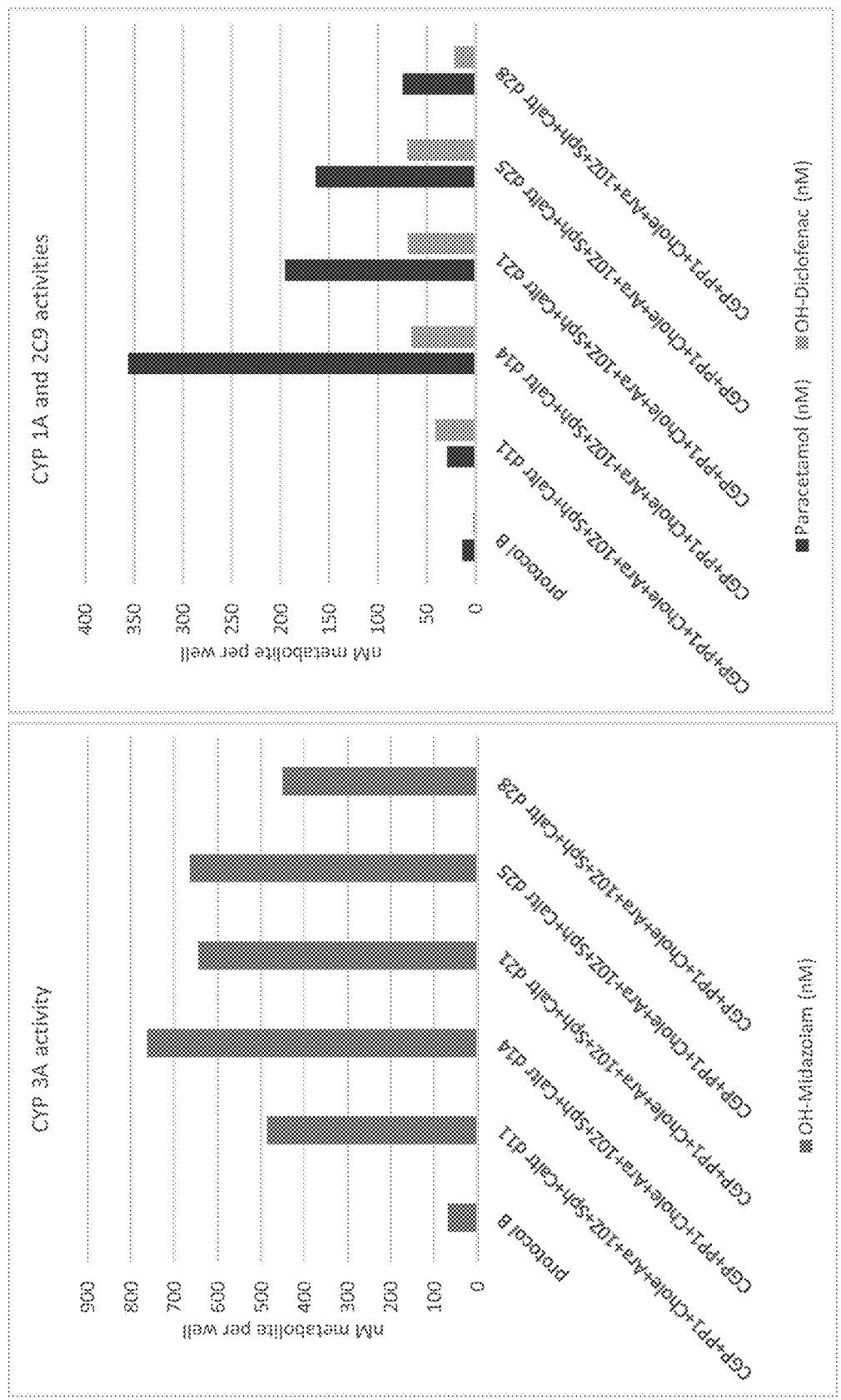
Figure 3D:
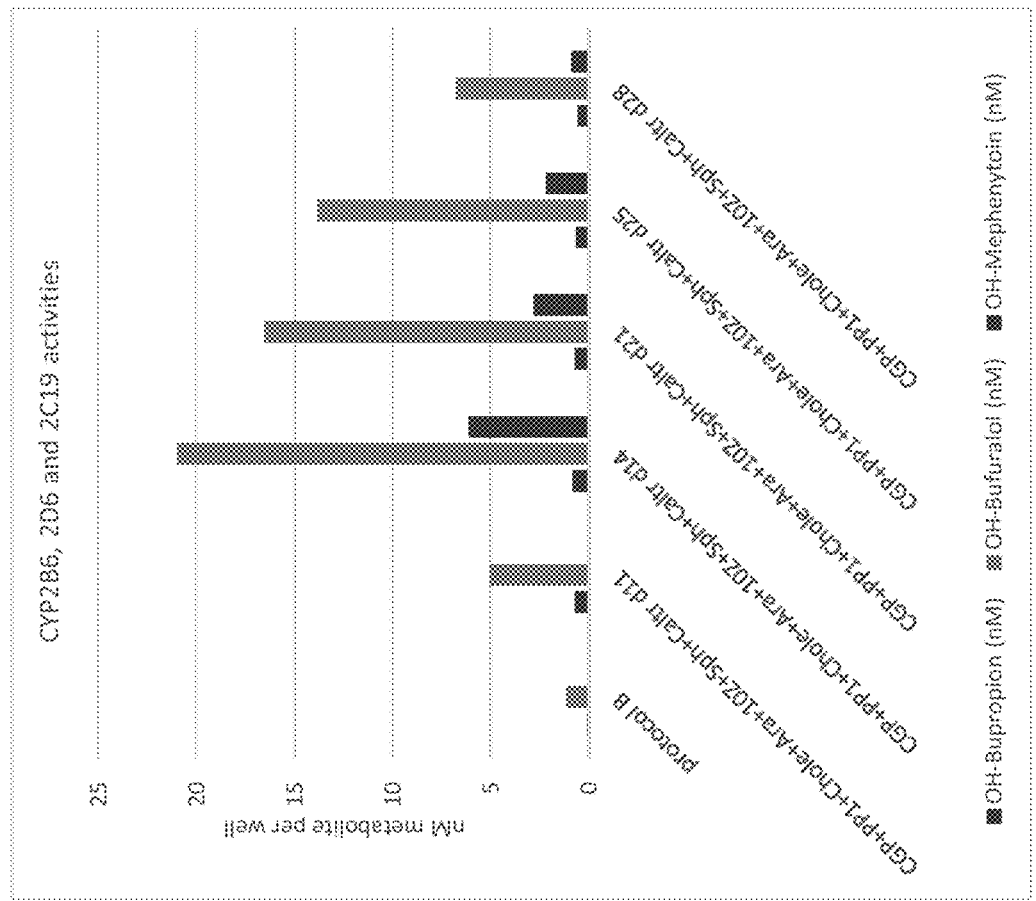
Figure 4B:
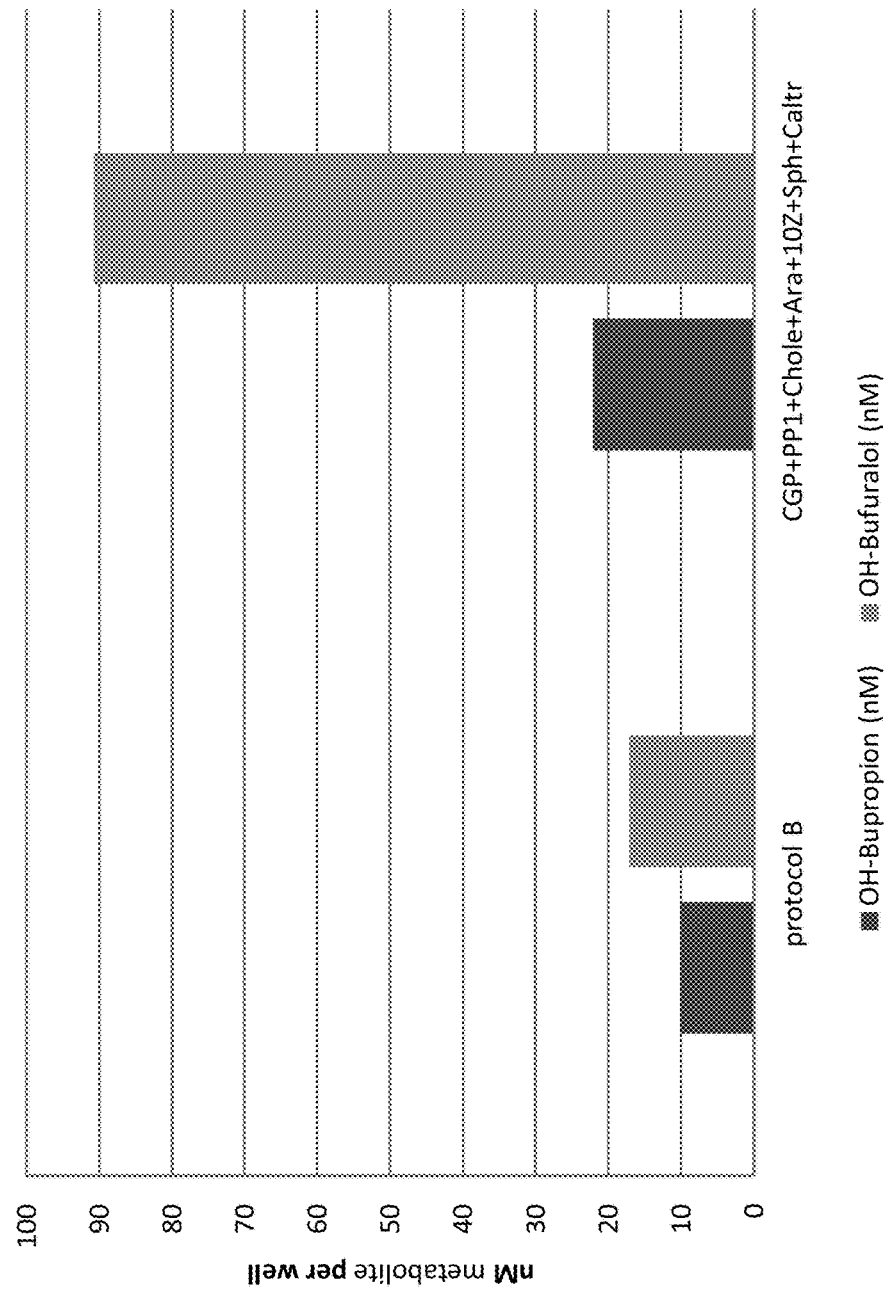
Figure 4D:
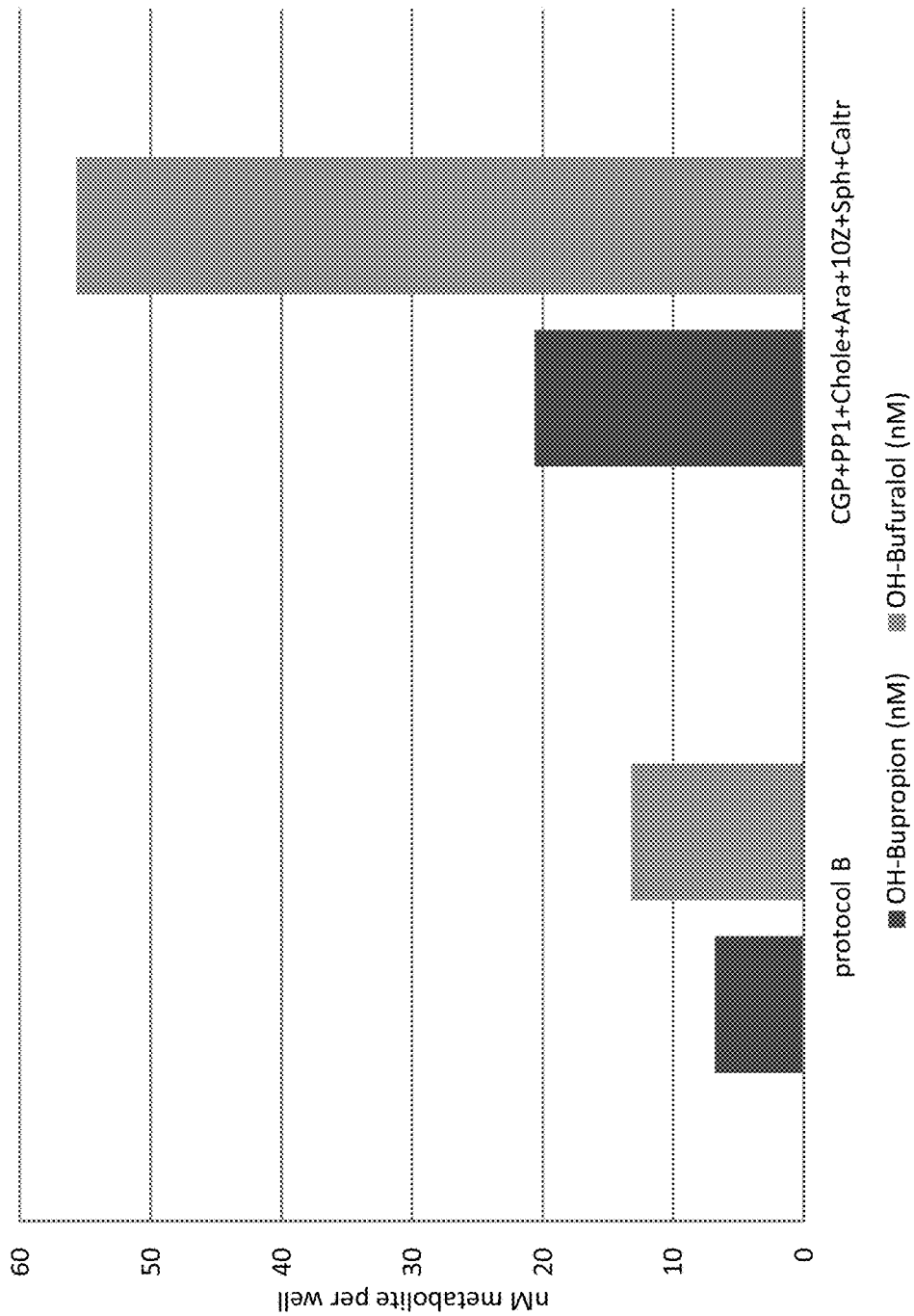
Figure 4E:
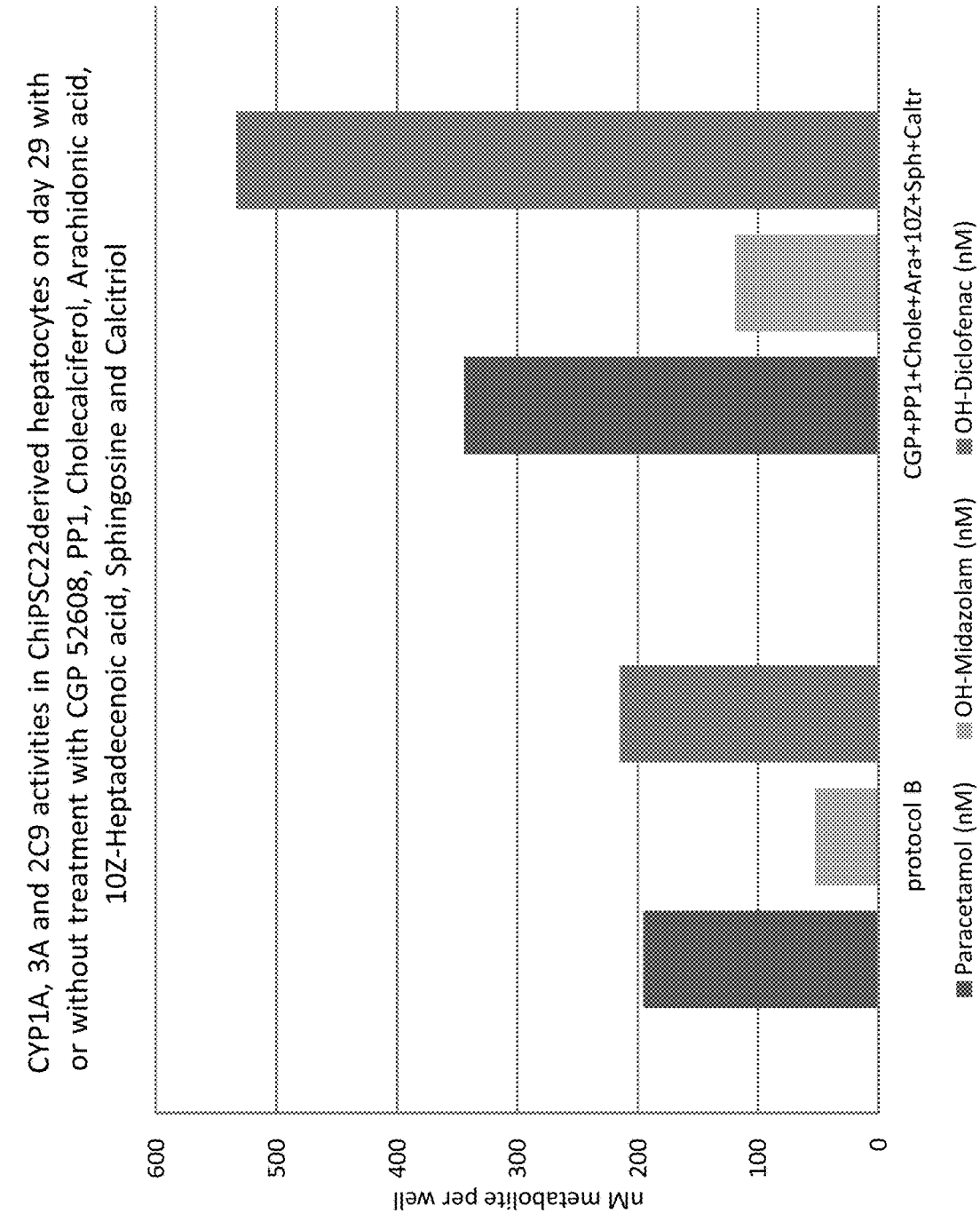
Figure 4G:
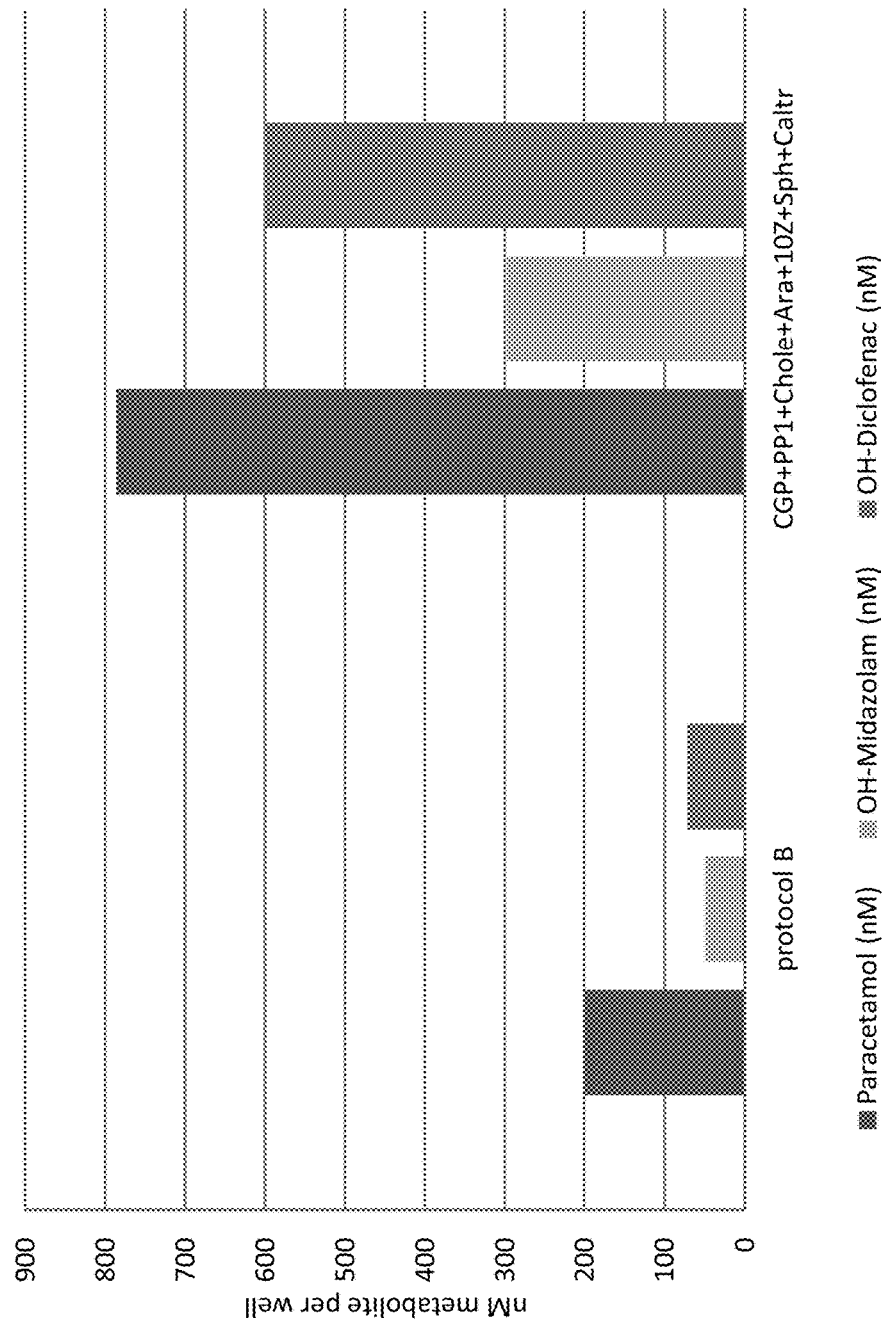
Figure 4I:
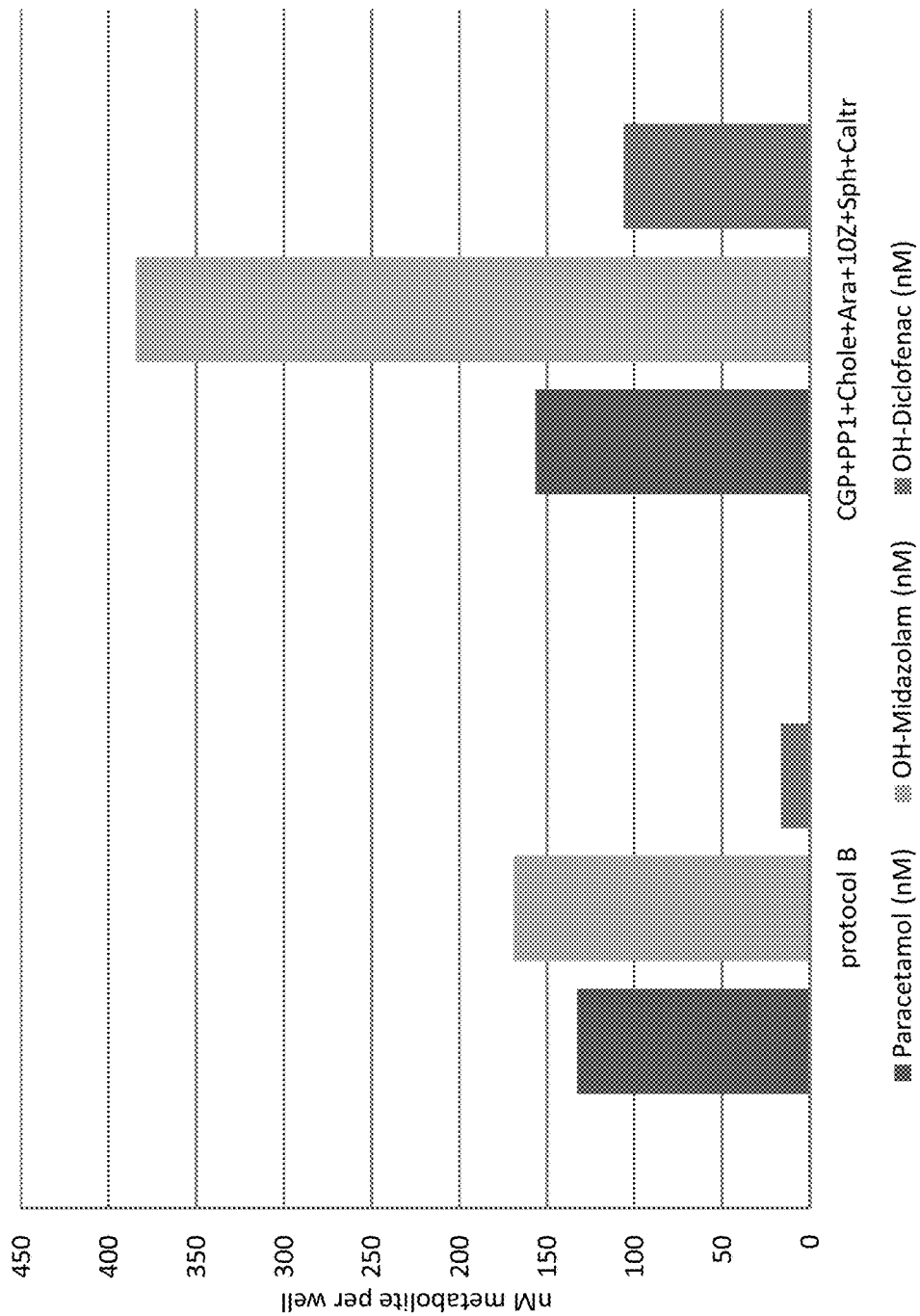
Figure 4J:
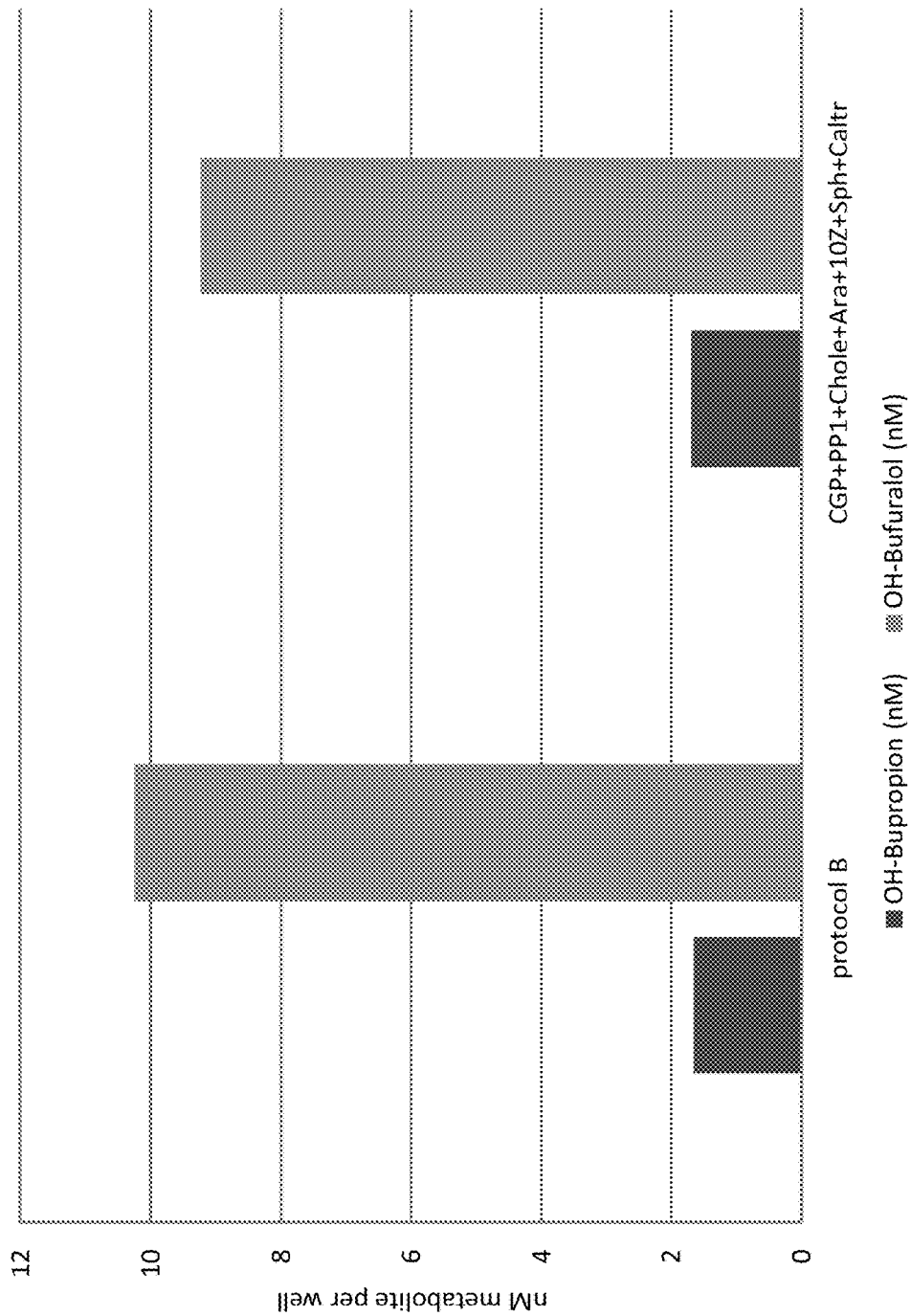
Figure 4K:
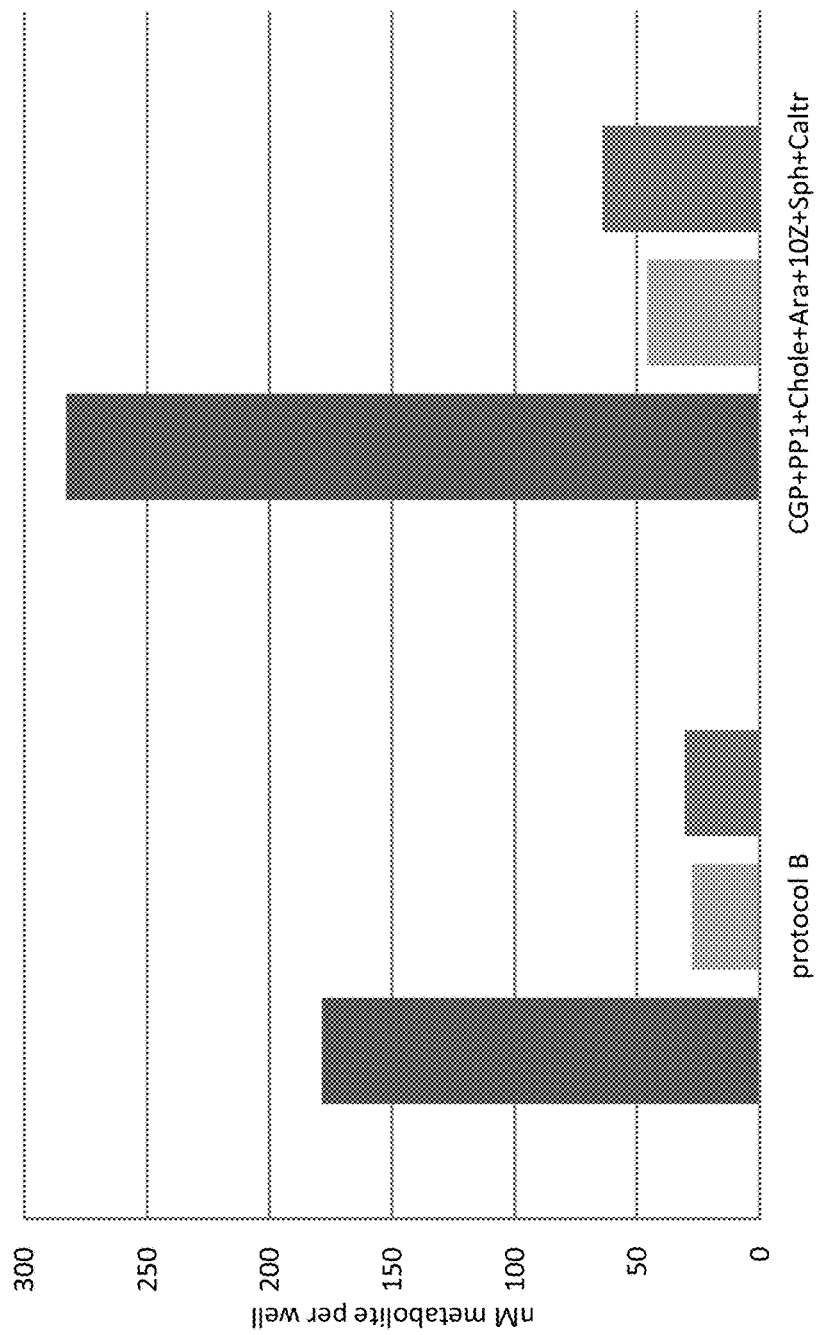
Figure 4N:
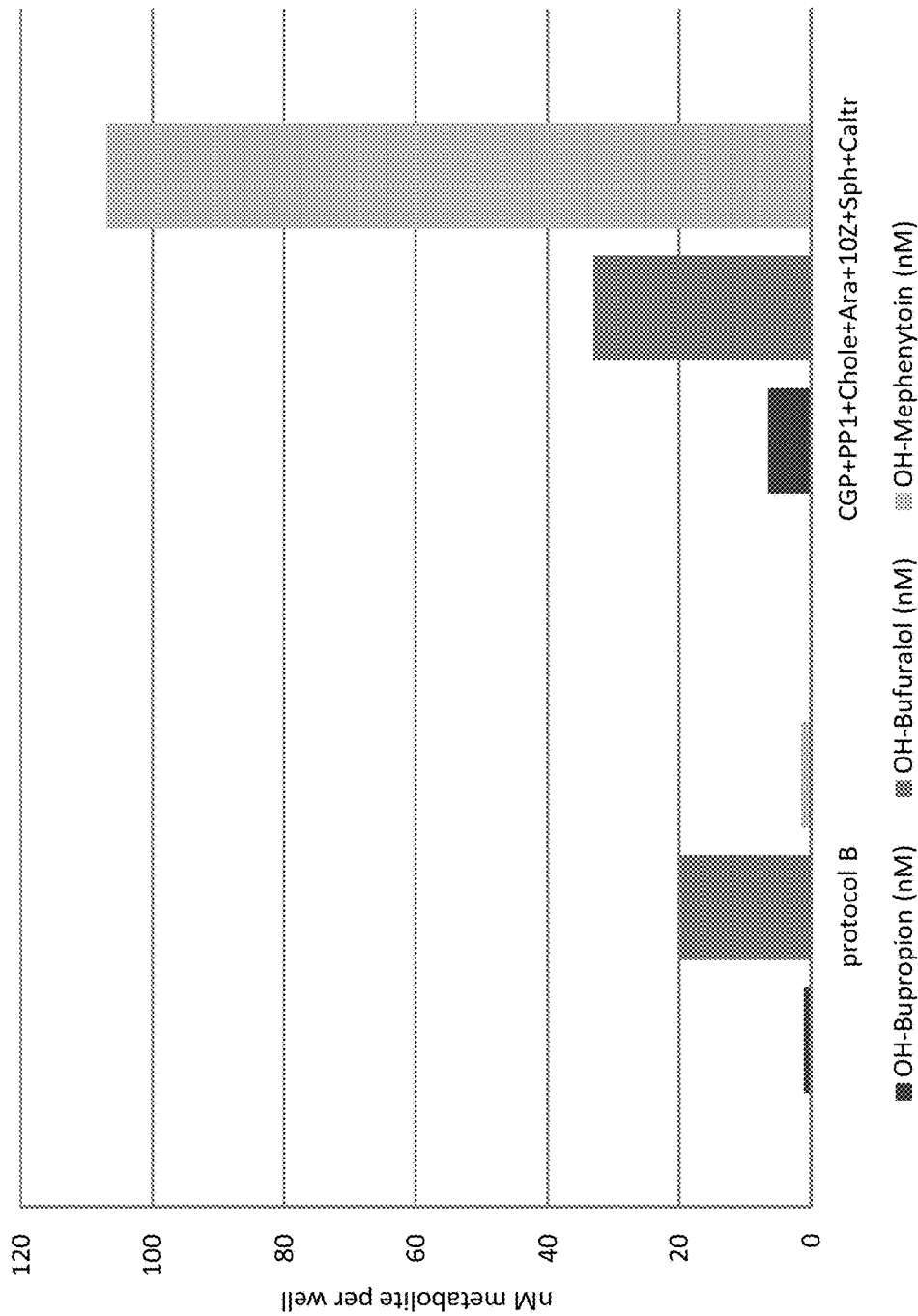

A-U: Effect of treatment with 10Z-Heptadecenoic acid (A,B), Arachidonic acid (C,D), Calcifediol (E,F), Calcitriol (E,F), Cholecalciferol (G,H), CGP 52608 (I,J), Docosahexaenoic acid (K,L), PP1 (M,N,O,P), PP2 (Q,R), D-erythro-Sphingosine (S,T), and Tetradecanoic acid (U) on CYP activities of hiPSC-derived hepatocytes on day 29 and/or 36 of the differentiation protocol.

Abbreviations: CGP=CGP 52608; CYP=Cytochrome P450; Sphingosine=D-erythro-Sphingosine.

FIG. 2.

A-D: Effect of treatment with 10Z-Heptadecenoic acid (A), Arachidonic acid (A), Calcitriol (C), Cholecalciferol (A), CGP 52608 (A), PP1 (A), D-erythro-Sphingosine (A), 13 cis-RA (B), L-erythro MAPP (B), PAF C16 (B), C16 Ceramide (B), and combinations of these compounds (A,C, D) on CYP activities of hiPSC-derived hepatocytes on day 29 and/or 36 of the differentiation protocol.

E-G: Effect of treatment with 10Z-Heptadecenoic acid (E,F) and a combination of CGP 52608, PP1, Cholecalciferol, Arachidonic acid, 10Z-Heptadecenoic acid, and D-erythro-Sphingosine (G) on mRNA expression levels of the nuclear receptor PXR (E,G) and the transporter protein OATP1B1 (F).

Abbreviations: 10Z=10Z-Heptadecenoic acid; 13 cis=13 cis retinoic acid; Ara=Arachidonic acid; Caltr=Calcitriol; Ceramide=C16 Ceramide; CGP=CGP 52608; Chole=Cholecalciferol; CYP=Cytochrome P450; MAPP=L-erythro MAPP; PAF=platelet activating factor; OATP1B1=organic anion-transporting polypeptide 1B1; PXR=pregnane X receptor; Sph=D-erythro-Sphingosine.

FIG. 3.

A,B: Effect of treatment with 10Z-Heptadecenoic acid, Arachidonic acid, Calcitriol, Cholecalciferol, CGP 52608, PP1, and D-erythro-Sphingosine starting at different time points of the differentiation protocol on CYP activities of hiPSC-derived hepatocytes on day 29 (A) and 36 (B) of the differentiation protocol.

Abbreviations: 10Z=10Z-Heptadecenoic acid; Ara=Arachidonic acid; Caltr=Calcitriol; CGP=CGP 52608; Chole=Cholecalciferol; CYP=Cytochrome P450; Sph=D-erythro-Sphingosine.

FIG. 4.

A-G: Effect of treatment of hepatocytes derived from the hiPS cell lines ChiPSC4 (A), ChiPSC6b (B), ChiPSC22 (C), P11015 (D), P11021 (E), P11032 (F), and the hES cell line SA121 (G) with 10Z-Heptadecenoic acid, Arachidonic acid, Calcitriol, Cholecalciferol, CGP 52608, PP1, and D-erythro-Sphingosine on day 29 of the differentiation protocol.

Abbreviations: 10Z=10Z-Heptadecenoic acid; Ara=Arachidonic acid; Caltr=Calcitriol; CGP=CGP 52608; Chole=Cholecalciferol; CYP=Cytochrome P450; Sph=D-erythro-Sphingosine.

FIG. 5.

A,B: Effect of treatment with 10Z-Heptadecenoic acid, Arachidonic acid, Calcitriol, Cholecalciferol, CGP 52608, PP1, and D-erythro-Sphingosine, and with or without Oncostatin M and/or HGF on CYP1A, 3A, and 2C9 (A) and CYP2B6, 2D6, and 2C19 (B) activities of hiPSC-derived hepatocytes on day 31 of the differentiation protocol.

Abbreviations: CYP=Cytochrome P450; HGF=hepatocyte growth factor; OSM=Oncostatin M.

EXAMPLES

Examples of general culturing and passaging techniques are disclosed in applications WO2004/099394, WO2003/055992, WO/2007/042225, WO2007/140968 and WO2011116930.

As laid out in the following examples, the starting material may comprise any hepatic progenitor cell type, particularly one derived through an initial differentiation towards a definitive or extraembryonic lineage from a mammalian pluripotent stem cell, such as a human pluripotent stem cell. The starting material may also be any cell of hepatic progenitor lineage.

Example 1: Maintenance of hPS Cell Types

All hPS cells (as defined above) can be used as staring material for this invention. For the examples below in particular hepatocytes were derived in vitro from undifferentiated human embryonic stem cells (hESC) established on mEF feeder cells (Heins et al 2004) and maintained under feeder-free conditions. The cell lines used for this experiment could be, but are not limited to the hES cell lines SA121, SA167, SA181, SA461 (Cellartis AB, Göteborg, Sweden) and they can be propagated as described by Heins et al. 2004 and Caisander et al. 2006.

Along with hPS obtained from hESC, hiPS (human induced pluripotent stem) cells have also been used for the derivation of hepatocytes for the examples of this invention. The hiPSC line ChiPSC4 used in this invention was derived as followed: Human dermal fibroblasts (CRL2429, ATCC) were maintained in DMEM supplemented with 10% fetal bovine serum, 1× glutamax, 5 U/ml penicillin and 5 µg/ml streptomycin at 37° C. in a humidified atmosphere of 5% $CO_2$ in air. Fibroblasts were transduced with recombinant lentiviruses encoding mouse Oct4, Sox2, Klf4 and c-myc and cultured for 5 days. The transduced cells were then dispersed with trypsin and seeded onto mitomycin C treated human dermal fibroblast feeder cells at a density of $5 \times 10^3$ cells/cm² in their normal growth medium. After 24 hours the medium was replaced with knockout DMEM supplemented with 20% knockout serum replacement, 1× non-essential amino acids, 1× glutamax, 5 U/ml penicillin, 5 µg/ml streptomycin, 100 µM 2-mercaptoethanol and 30 ng/ml bFGF at 37° C. in a humidified atmosphere of 5% $CO_2$ in air. Half of the volume of medium was replaced every day and colonies of iPS cells emerged after approximately 30 days. iPS colonies were picked, expanded in DEF-CS™, and cell banks prepared. The banked cells were then characterised to check for the expression of endogenous Oct4, Sox2, Klf4 and c-Myc, silencing of transgenes, potential to differentiate into cell types representative of all three germ layers in vitro, and to confirm their authenticity by STR profiling and comparison with the parental fibroblast cell line (ATCC).

The hiPSC line ChiPSC6b used in this invention was derived from fibroblast line P11031 (Cellectis SA) by transfecting with episomal vectors encoding OCT4, SOX2, KLF4, LIN28, and L-MYC using electroporation (Neon transfection system; Invitrogen).

All other hiPSC lines used in this invention were obtained from Cellectis SA and were derived from either peripheral blood cells (P11021) or adult dermal fibroblasts (ChiPSC18, ChiPSC22, P11015, P11021, P11032) using either episomal (P11021) or retroviral reprogramming (ChiPSC18, ChiPSC22, P11015, P11021, P11032) with OCT4, SOX2, KLF4, LIN28, and L-MYC. These 6 hiPSC lines were initially established in a Matrigel-based culture system and subsequently transferred to the DEF-CS.

Alternatively to reprogramming using lentivirus, retrovirus and episomal vectors, hiPSC lines can also be reprogrammed using Sendai virus, adenovirus, proteins and mRNAs or other techniques. Other suitable cell lines for use are those established by Chung et al. (2008), such as cell lines MA126, MA127, MA128 and MA129 (Advanced Cell Technology, Inc. Worcester, Mass., USA), which all are listed with the International stem cell registry. These cell lines have been derived (or obtained) without destruction of the human embryo by employing a single blastomere removal technique.

All hPSC lines used in this invention were cultured under standard conditions in the DEF-CS with continuous passaging twice a week and were immuno-positive for OCT4, TRA1-60, TRA1-81, and SSEA-4, and immuno-negative for SSEA-1. Pluripotency was confirmed by in vitro differentiation. Karyotyping as described by Caisander et al. 2006 showed a normal chromosomal profile.

Example 2: Differentiation of hPS Cell Types to Produce Hepatocytes

Hepatocytes may be derived from hPS cells by employing the following exemplary basic protocols A and B:
Protocol A:

Undifferentiated hPS cells are dissociated and seeded directly in day 0-medium onto a Fibronectin-based coating. The different mediums were prepared freshly and added day 0, 1, 2, 3, 4, 5, 7 and then every second or third day during the pre-hepatic phase, and differentiation and maturation phase.
Day 0
Pre-treatment medium
3 µM CHIR99021
5 µM ROCK inhibitor
Day 1
RPMI 1640 (+0.1% PEST+1% Glutamax)
1×B27
50 ng/ml Activin A
3 µM CHIR99021
5 µM LY294002
3 µM CHIR99021
Day 2
RPMI 1640 (+0.1% PEST+1% Glutamax)
1×B27
50 ng/ml Activin A
5 µM LY294002
10 nM 5-aza-2-deoxycytidine
Day 3
RPMI 1640 (+0.1% PEST+1% Glutamax)
1×B27
50 ng/ml Activin A
Day 4-7
RPMI 1640 (+0.1% PEST+1% Glutamax)
1×B27
50 ng/ml Activin A The pre-treatment medium is available from Takara Bio Europe AB (Arvid Wallgrens Backe 20, 41346 Gothenburg, Sweden) upon request.

On day 7 the cells are passaged. The cells are incubated for 3-7 minutes with TrypLE Select at 37° C., the same volume of BasHES is added and the cell suspension is centrifuged at 200-300 g, 5-6 min. Thereafter, the cells are replated onto a Fibronectin-based coating at a cell density of 50 000-350 000 cells/cm$^2$ such as e.g. 75 000-300 000 cells/cm$^2$, preferably 100 000 cells/cm$^2$. The Fibronectin-based coating has a concentration of 7.5 μg Fibronectin per cm$^2$ culture area. To prepare the coating, 50 μl of a 1 mg/ml Fibronectin stock is added per ml DPBS, and 150 μl of this coating solution is added per cm$^2$ culture area.

Day 7-14 (Pre-Hepatic)
Knockout-DMEM+1% PEST+1% Glutamax
20% Knockout-Serum Replacement
1% non-essential amino acids (NEAA)
0.2% beta-mercaptoethanol
1% DMSO
Day 14-45 (Differentiation and Maturation)
WME+1% Glutamax+0.1% PEST
0.55 mg/mL BSA-FAF
0,025 mg/mL Ascorbic Acid
0.67 μg/mL Hydrocortisone Hemisuccinate
10 μg/mL Transferrin
5 μg/mL Insulin
0.003 μg/mL EGF
0.1 μM DexM
10 ng/ml OsM
20 ng/ml HGF
0.5% DMSO
1.4 μM BIO
0.5 μM Kenpaullone
0.2 μM 9cis retinoic acid On day 14 and 16, matrix overlays are performed. To this end, 53 μl of a 1 mg/ml Fibronectin stock and 9 μl of a 3 mg/ml Collagen I stock are added per ml day 14-45 medium (RT), the medium is mixed well and then a regular medium change is perfomed. The addition of the matrix components corresponds to the addition of 25 μg Fibronectin and 12.5 μg Collagen I per cm$^2$ culture area per overlay addition.

Protocol B:

Undifferentiated hPS cells are dissociated and seeded directly in day 0-medium onto a Fibronectin-based coating. The different mediums were prepared freshly and added day 0, 1, 2, 3, 4, 5, 7 and then every second or third day during the pre-hepatic phase, and differentiation and maturation phase.

Day 0
Pre-treatment medium
3 μM CHIR99021
5 μM ROCK inhibitor
Day 1
RPMI 1640 (+0.1% PEST+1% Glutamax)
1×B27
50 ng/ml Activin A
3 μM CHIR99021
5 μM LY294002
3 μM CHIR99021
Day 2
RPMI 1640 (+0.1% PEST+1% Glutamax)
1×B27
50 ng/ml Activin A
5 μM LY294002
10 nM 5-aza-2-deoxycytidine Day 3
RPMI 1640 (+0.1% PEST+1% Glutamax)
1×B27
50 ng/ml Activin A
Day 4-7
RPMI 1640 (+0.1% PEST+1% Glutamax)
1×B27
50 ng/ml Activin A The pre-treatment medium is available from Takara Bio Europe AB (Arvid Wallgrens Backe 20, 41346 Gothenburg, Sweden) upon request.

On day 7 the cells are passaged. The cells are incubated for 3-7 minutes with TrypLE Select at 37° C., the same volume of BasHES is added and the cell suspension is centrifuged at 200-300 g, 5-6 min. Thereafter, the cells are replated onto a Collagen I-Fibronectin-based coating at a cell density of 50 000-350 000 cells/cm$^2$ such as e.g. 75 000-300 000 cells/cm$^2$, preferably 100 000 cells/cm$^2$. The Collagen I-Fibronectin-based coating has a concentration of 2 μg Fibronectin and 10 μg Collagen I per cm$^2$ culture area. To prepare the coating, 12 μl of a 1 mg/ml Fibronectin stock and 21.5 μl of a 3 mg/ml Collagen I stock is added per ml DPBS, and 150 μl of this coating solution is added per cm$^2$ culture area.

Day 7-14 (Pre-Hepatic)
Knockout-DMEM+1% PEST+1% Glutamax
20% Knockout-Serum Replacement
1% non-essential amino acids (NEAA)
0.2% beta-mercaptoethanol
1% DMSO
Day 14-45 (Differentiation and Maturation)
WME+1% Glutamax+0.1% PEST
0.55 mg/mL BSA-FAF
0,025 mg/mL Ascorbic Acid
0.67 μg/mL Hydrocortisone Hemisuccinate
10 μg/mL Transferrin
5 μg/mL Insulin
0.003 μg/mL EGF
0.1 μM DexM
10 ng/ml OsM
20 ng/ml HGF
0.5% DMSO
1.4 μM BIO
0.5 μM Kenpaullone
0.2 μM 9cis retinoic acid On day 14 and 16, matrix overlays are performed. To this end, 12 μl of a 1 mg/ml Fibronectin stock solution and 21.5 μL of a 3 mg/ml Collagen I stock solution are added per ml day 14-45 medium (RT), the medium is mixed well and then a regular medium change is perfomed. The addition of the matrix components corresponds to the addition of 6 μg Fibronectin and 31.25 μg Collagen I per cm$^2$ culture area per overlay addition.

Example 3: Effect of Treatment of hiPSC-Derived Hepatocytes with 10Z-Heptadecenoic Acid, Arachidonic Acid, Calcifediol, Calcitriol, Cholecalciferol, CGP 52608, Docosahexaenoic Acid, PP1, PP2, D-Erythro-Sphingosine, and Tetradecanoic Acid Procedure:

Following the basic protocol A, hiPS cell derived hepatocytes cultured on a Fibronectin-based coating were treated with 0.5 or 5 μM 10Z-Heptadecenoic acid, 0.5 or 5 μM Arachidonic acid, 5 μM Calcifediol, 5 μM Calcitriol, 0.2 or 0.5 μM Cholecalciferol, 5 or 50 μM CGP 52608, 0.5 or 5 μM Docosahexaenoic acid, 0.5, 1.25, 2.5, 5, or 10 μM PP1, 0.5 or 5 µM PP2, 0.5 or 5 µM D-erythro-Sphingosine, or 0.5 or 5 µM Tetradecanoic acid from day 21 of the differentiation protocol and onwards (FIG. 1).

On day 29 and 36 of the differentiation protocol, the cell cultures are subjected to a CYP activity assay according to the following protocol: Cells are washed twice with warm Williams's medium E w/o phenol red (+0.1% PEST). Then CYP activity assay, consisting of warm Williams medium E w/o phenol red (+0.1% PEST), 2 mM L-Glutamine, 25 mM HEPES, 10 µM Phenacetin (model substrate for CYP1A), 10 µM Bupropion (model substrate for 2B6), 10 µM Diclofenac (model substrate for CYP2C9), 10 µM Bufuralol (model substrate for 2D6), and 5 µM Midazolam (model substrate for CYP3A), is added to the cells (e.g. 110 µl/cm$^2$) and incubated for 16 hr at 37° C. Then 100 µl of the supernatant is transferred into a 96 well plate which is sealed with a tight seal tape and stored at −80° C. until LC/MS-analysis of metabolite formation: Acetaminophen (Paracetamol) for CYP1A, OH-Bupropion for CYP2B6, OH-Diclofenac for CYP2C9, OH-Bufuralol for CYP2D6, and OH-Midazolam for CYP3A.

Results:

FIG. 1 A-U) 10Z-Heptadecenoic acid, Arachidonic acid, Calcifediol, Calcitriol, Cholecalciferol, CGP 52608, Docosahexaenoic acid, PP1, PP2, D-erythro-Sphingosine, and Tetradecanoic acid increase CYP activity levels in hiPS cell-derived hepatocytes both on day 29 and 36 of the differentiation protocol. In some cases, 2B6 activity levels were below the detection level.

These eleven compounds increase CYP activity levels in hiPS cell-derived hepatocytes. Therefore the skilled person wishing to improve CYP activity may select from these compounds according to their interest.

Example 4: Effect of Treatment of hiPSC-Derived Hepatocytes with 10Z-Heptadecenoic Acid, Arachidonic Acid, Calcitriol, Cholecalciferol, CGP 52608, PP1, D-Erythro-Sphingosine, 13 Cis-RA, L-Erythro MAPP, PAF C16, C16 Ceramide, and Combinations of these Compounds Procedure:

Following the basic protocol B, ChiPSC4-derived hepatocytes cultured on a Collagen I-Fibronectin-based coating were treated with 0.5 µM 10Z-Heptadecenoic acid, 0.5 µM Arachidonic acid, 0.5 µM Calcitriol, 5 µM CGP 52608, 0.2 µM Cholecalciferol, 5 µM PP1, 0.5 µM D-erythro-Sphingosine, 0.2 µM 13 cis-RA, 0.5 µM L-erythro MAPP, 0.5 µM PAF C16, 0.5 µM C16 Ceramide, or different combinations of these compounds from day 21 of the differentiation protocol and onwards (FIG. 2).

On day 29 of the differentiation protocol, the cell cultures are subjected to a CYP activity assay according to the protocol described in Example 3. In some experiments, 50 µM Mephenytoin (model substrate for 2C19) was included additionally to the substrates mentioned above and then the formation of the metabolite OH-Mephenytoin was measured by LC/MS in order to determine CYP2C19 activity.

Results:

FIG. 2 A-D) 10Z-Heptadecenoic acid (10Z), Arachidonic acid (Ara), Calcitriol (Caltr), Cholecalciferol (Chole), CGP 52608 (CGP), PP1, D-erythro-Sphingosine (Sph), 13 cis-RA (13 cis), L-erythro MAPP (MAPP), PAF C16 (PAF), C16 Ceramide (Cera), or different combinations of these compounds increase CYP activity levels in hiPS cell-derived hepatocytes on day 29 of the differentiation protocol. In some cases, 2B6 activity levels were below the detection level.

FIG. 2 E,F) Protocol B and protocol B plus 10Z-Heptadecenoic acid increase OATP1B1 and PXR mRNA levels in hiPS cell-derived hepatocytes on day 36 of the differentiation protocol compared to protocol A.

FIG. 2 G) Protocol B plus CGP 52608, PP1, Cholecalciferol, Arachidonic acid, 10Z-Heptadecenoic acid, and Sphingosine increase PXR mRNA levels in hiPS cell-derived hepatocytes on day 29 and 36 of the differentiation protocol compared to protocol A.

These eleven compounds increase CYP activity levels in hiPS cell-derived hepatocytes. Therefore the skilled person wishing to improve CYP activity may select from these compounds according to their interest.

Example 5: Effect of Treatment of hiPSC-Derived Hepatocytes with 10Z-Heptadecenoic Acid, Arachidonic Acid, Calcitriol, Cholecalciferol, CGP 52608, PP1, and D-Erythro-Sphingosine Starting at Different Time Points of the Differentiation Protocol Procedure:

Following the basic protocol B, ChiPSC4-derived hepatocytes cultured on a Collagen I-Fibronectin-based coating were treated with 0.5 µM 10Z-Heptadecenoic acid, 0.5 µM Arachidonic acid, 0.5 µM Calcitriol, 5 µM CGP 52608, 0.2 µM Cholecalciferol, 5 µM PP1, and 0.5 µM D-erythro-Sphingosine starting on day 11, 14, 21, 25 and 28, respectively, of the differentiation protocol and onwards (FIG. 3).

On day 29 and 36 of the differentiation protocol, the cell cultures are subjected to a CYP activity assay according to the following described in Example 3.

Results:

FIG. 3 A,B) Treatment with 10Z-Heptadecenoic acid (10Z), Arachidonic acid (Ara), Calcitriol (Caltr), Cholecalciferol (Chole), CGP 52608 (CGP), PP1, and D-erythro-Sphingosine (Sph) starting between day 11 and 28 of the differentiation protocol increases CYP activity levels in hiPS cell-derived hepatocytes on day 29 and 36 of the differentiation protocol.

The treatment with the seven compounds starting between day 11 and 28 of the differentiation protocol increases CYP activity levels in hiPS cell-derived hepatocytes. Therefore the skilled person wishing to improve CYP activity may select from these different time points to start the treatment according to their interest.

Example 6: Effect of Treatment of Hepatocytes Derived from Several hiPS and hES Cell Lines with 10Z-Heptadecenoic Acid, Arachidonic Acid, Calcitriol, Cholecalciferol, CGP 52608, PP1, and D-Erythro-Sphingosine Procedure:

Following the basic protocol B, hepatocytes derived from the hiPS cell lines ChiPSC4, ChiPSC6b, ChiPSC22, P11015, P11021, P11032 and the hES cell line SA121 were cultured on a Collagen I-Fibronectin-based coating and treated with a combination of 0.5 µM 10Z-Heptadecenoic acid, 0.5 µM Arachidonic acid, 0.5 µM Calcitriol, 5 µM CGP 52608, 0.2 µM Cholecalciferol, 5 µM PP1, and 0.5 µM D-erythro-Sphingosine from day 21 of the differentiation protocol and onwards (FIG. 4).

On day 29 of the differentiation protocol, the cell cultures are subjected to a CYP activity assay according to the following protocol described in Example 3. In some experiments, 50 µM Mephenytoin (model substrate for 2C19) was included additionally to the substrates mentioned above and then the formation of the metabolite OH-Mephenytoin was measured by LC/MS in order to determine CYP2C19 activity.

Results:

FIG. 4 A-G) The treatment with 10Z-Heptadecenoic acid (10Z), Arachidonic acid (Ara), Calcitriol (Caltr), Cholecalciferol (Chole), CGP 52608 (CGP), PP1, and D-erythro-Sphingosine (Sph) increases CYP activity levels in hepatocytes derived from the hiPS cell lines ChiPSC4 (A), ChiPSC6b (B), ChiPSC22 (C), P11015 (D), P11021 (E), P11032 (F) and the hES cell line SA121 (G) on day 29 of the protocol.

These seven compounds increase CYP activity levels in both hiPS and hES cell-derived hepatocytes. Therefore the skilled person wishing to improve CYP activity may select from these compounds according to their interest.

Figure 5A:
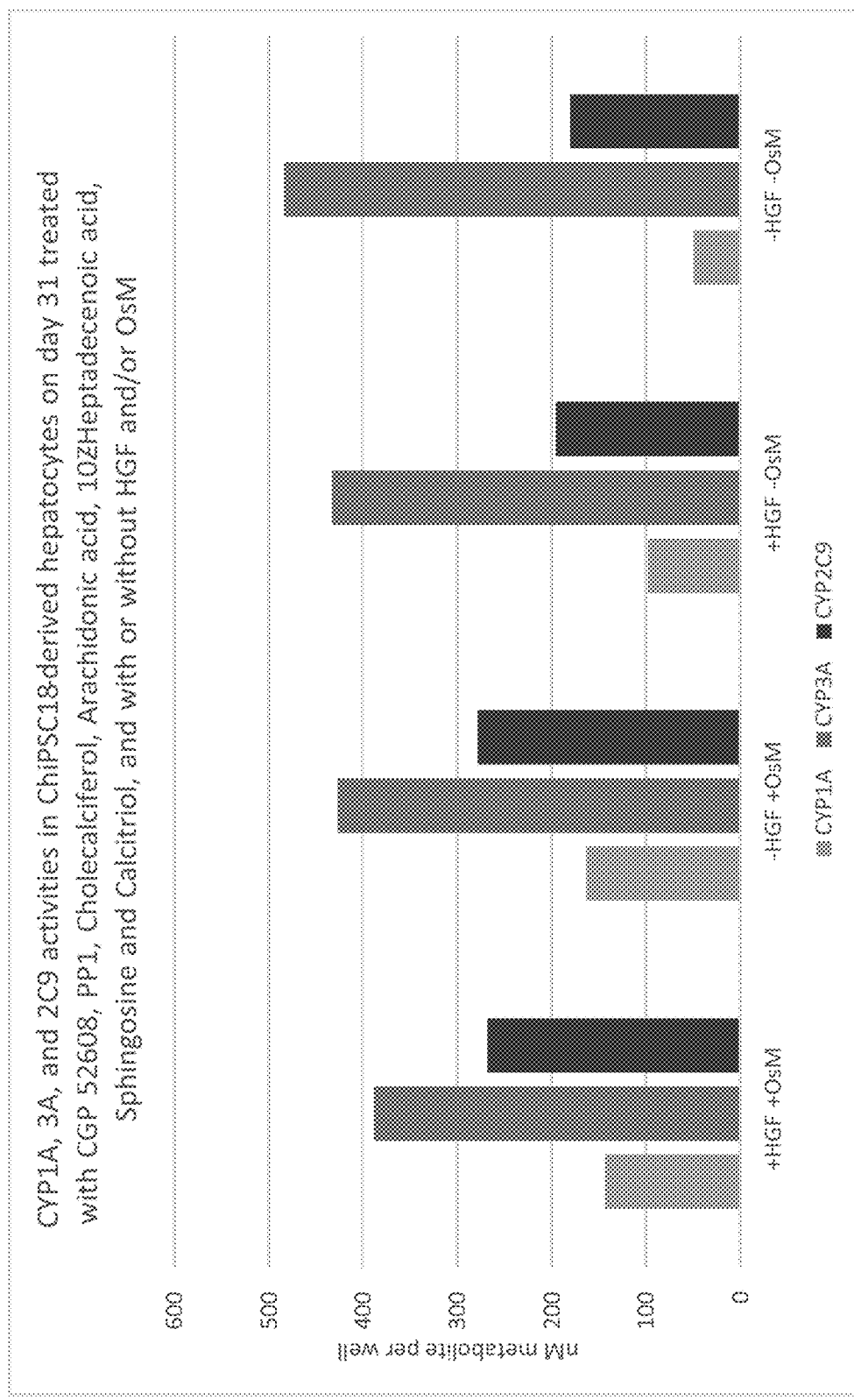
Figure 5B:
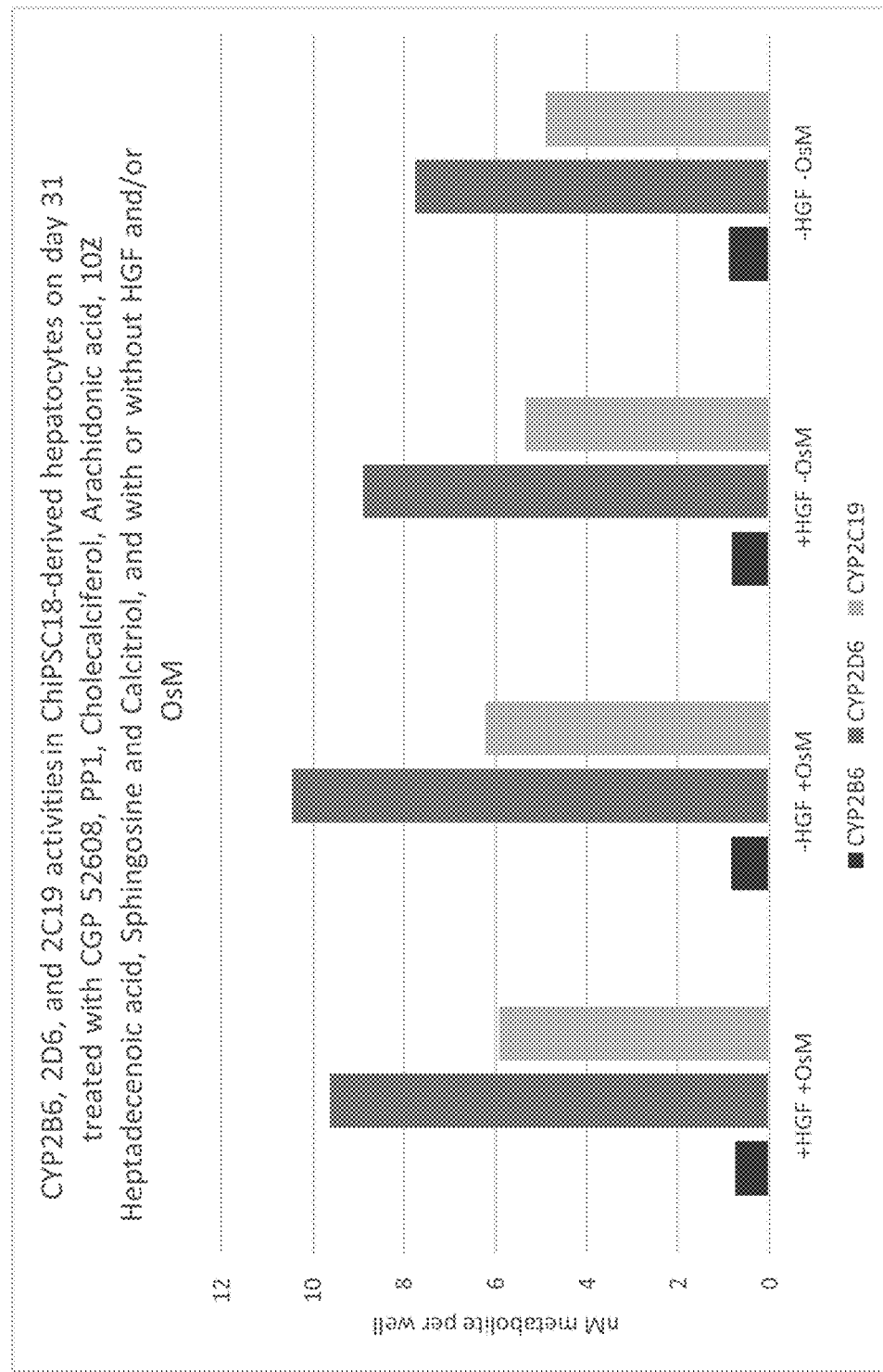

Example 7: Effect of Treatment of hiPSC-Derived Hepatocytes with 10Z-Heptadecenoic Acid, Arachidonic Acid, Calcitriol, Cholecalciferol, CGP 52608, PP1, and D-Erythro-Sphingosine with or without the Addition of Oncostatin M and/or HGF Procedure:

Following the basic protocol B, hepatocytes derived from the hiPS cell line ChiPSC18 were cultured on a Collagen I-Fibronectin-based coating and treated with a combination of 0.5 µM 10Z-Heptadecenoic acid, 0.5 µM Arachidonic acid, 0.5 µM Calcitriol, 5 µM CGP 52608, 0.2 µM Cholecalciferol, 5 µM PP1, and 0.5 µM D-erythro-Sphingosine and with or without Oncostatin M and/or HGF from day 21 of the differentiation protocol and onwards (FIG. 5).

On day 31 of the differentiation protocol, the cell cultures are subjected to a CYP activity assay according to the following protocol described in Example 3. 50 µM Mephenytoin (model substrate for 2C19) was included additionally to the substrates mentioned above and the formation of the metabolite OH-Mephenytoin was measured in order to determine CYP2C19 activity.

Results:

FIG. 5 A,B) The treatment with 10Z-Heptadecenoic acid, Arachidonic acid, Calcitriol, Cholecalciferol, CGP 52608, PP1, and D-erythro-Sphingosine, and with or without Oncostatin M and/or HGF results in similar CYP activity levels in hepatocytes derived from the hiPS cell line ChiPSC18 on day 31 of the protocol.

These seven compounds increase CYP activity levels in both hiPS and hES cell-derived hepatocytes independent of the presence of Oncostatin M and/or HGF. Therefore, the skilled person wishing to improve CYP activity may select from these compounds according to their interest and include or exclude Oncostatin M and/or HGF.

REFERENCES

Brolen, G. et al. (2010) Hepatocyte-like cells derived from human embryonic stem cells specifically via definitive endoderm and a progenitor stage. J Biotechnol. 1; 145 (3):284-94

Chen, Y. F. et al. (2012) Rapid generation of mature hepatocyte-like cells from human induced pluripotent stem cells by an efficient three-step protocol. Hepatology. 2012 55(4):1193-203

Chung, Y. et al. (2008) Human Embryonic Stem Cell Lines Generated without Embryo Destruction. doi: 10.1016/j.stem.2007.12.013

Duan, Y. et al. Differentiation and characterization of metabolically functioning hepatocytes from human embryonic stem cells. Stem Cells. 28(4):674-86

Dunn, J et al. (1991) Long-term in Vitro function of adult hepatocytes in a collagen sandwich configuration. Biotechnol. Prog. 7:237-245

D'Amour K. A. et al. (2005) Efficient differentiation of human embryonic stem cells to definitive endoderm. Nat Biotechnology. 23(12):1534-41.

Funakoshi, N. et al. (2011) Comparison of hepatic-like cell production from human embryonic stem cells and adult liver progenitor cells: CAR transduction activates a battery of detoxification genes. Stem Cell Rev. 7(3):518-31

Hay, D. et al (2007) Direct differentiation of human embryonic stem cells to hepatocyte-like cells exhibiting functional activities. Cloning Stem Cells. 2007 Spring; 9(1): 51-62.

Erratum in: Cloning Stem Cells. 2009 March; 11(1):209.

Hay, D. et al (2008) Efficient differentiation of hepatocytes from human embryonic stem cells exhibiting markers recapitulating liver development in vivo. Stem Cells. April; 26(4):894-902.

Heins, N. et al (2004) Derivation, characterization, and differentiation of human embryonic stem cells. Stem Cells. 22(3):367-76.

Klimanskaya, I. et al (2006) Human embryonic stem cell lines derived from single blastomeres. Nature, November 23; 444(7118):481-5. Epub 2006 Aug. 23. Erratum in: Nature. 2006 Nov. 23; 444(7118):512. Nature. 2007 Mar. 15; 446(7133):342.

Martin M. et al (2005) Human embryonic stem cells express an immunogenic nonhuman sialic acid. Nat Med. February; 11(2):228-32.

Mercader, A. et al (2009) Human Embryo Culture. Essential Stem Cell Methods, Chapter 16, Academic Press, 1$^{st}$ Edition, Eds. Lanza, R. and Klimanskaya, I.

Page, J et al. (2007) Gene expression profiling of extracellular matrix as an effector of human hepatocyte phenotype in primary cell culture. Tox. Sci. 97(2):384-397

Si-Tayeb, K. et al. (2010) Highly efficient generation of human hepatocyte-like cells from induced pluripotent stem cells Hepatology. 51(1):297-305.

Song. Z. et al. (2009) Efficient generation of hepatocyte-like cells from human induced pluripotent stem cells. Cell Res. 19(11):1233-42

Sullivan, G. J. et al. (2010) Generation of functional human hepatic endoderm from human induced pluripotent stem cells. Hepatology. 51(1):329-35.

Siller, R. et al. (2015) Small-molecule-driven hepatocyte differentiation of human pluripotent stem cells. Stem Cell Reports 4(5):939-52.

Takahashi, K. et al (2007) Induction of pluripotent stem cells from adult human fibroblasts by defined factors. Cell November 30; 131(5):861-72.

Thomson, J. et al. (1998) Embryonic stem cell lines derived from human blastocysts. Science. November 6; 282 (5391):1145-7. Erratum in: Science 1998 Dec. 4; 282 (5395):1827.

Turner, R. et al. (2011) Human hepatic stem cell and maturational liver lineage biology. Hepatology. 53(3): 1035-45

Wang, Y. et al. (2011) Lineage restriction of human hepatic stem cells to mature fates is made efficient by tissue-specific biomatrix scaffolds. Hepatology. 53(1):293-305.

Yu, J. and Thomson, J. (2009) Induced Puripotent Stem Cell Derivation. Essentials of Stem Cell Biology, Chapter 37, Academic Press, 2$^{nd}$ Edition (2009), Eds. Lanza, R. et al.

Zhou H. et al (2009). Generation of induced pluripotent stem cells using recombinant proteins. Cell Stem Cell. 4(5): 381-4.

The invention claimed is:

1. A method for promoting the maturation of human hepatocytes, which have been derived in vitro from human pluripotent stem cells or human hepatic progenitor cells, the method comprising: exposing said hepatocytes to at least one Src kinase inhibitor selected from the group consisting of 4-Amino-1-tert-butyl-3-(4-methylphenyl)pyrazolo[3,4-d]pyrimidine (PP1), 4-Amino-5-(4-chlorophenyl)-7-(dimethylethyl)pyrazolo[3,4-d]pyrimidine (PP2), 4-Amino-1-tert-butyl-3-(1'-naphthyl)pyrazolo[3,4-d]pyrimidine (1-NA PP1), 4-Amino-1-tert-butyl-3-(1'-naphthylmethyl)pyrazolo[3,4-d]pyrimidine (1-NM-PP1), Src Inhibitor-1 (Src-I1), Src Kinase Inhibitor I, Src Kinase Inhibitor II, A-419529, A-770041, AZM 475271, bosutinib, CGP77675, Damnacanthal, dasatinib, dasatinib monohydrate, ER 27319 maleate, Fingolimod (FTY720), Geldanamycin, Herbimycin A, KB SRC 4, KX2-391, KX1-004, Lavendustin A, Lavendustin C, LCK inhibitor 2, Lyn peptide inhibitor, MLR-1023, MNS, N-Acetyl-O-phosphono-Tyr-Glu Dipentylamide, N-Acetyl-O-phosphono-Tyr-Glu-Glu-Ile-Glu, NVP-BHG712, PD 166285, PD173952, PD 180970, pp60 c-src, quercetin, radicicol from *Diheterospora chlamydosporia* solid, saracatinib, SU 6656, TC-S 7003, TG 100572, WH-4-023, ZM 306416, and combinations thereof, optionally in combination with at least one maturation factor selected from the group consisting of vitamin D including precursors, metabolites and analogs thereof, hypoxia inducing compounds, sphingosine and sphingosine derivatives, activators of peroxisome proliferator-activated receptors (PPARs), platelet-activating factor (PAF), and PKC inhibitors.

2. Method according to claim 1, wherein said at least one Src kinase inhibitor is PP1, PP2 or a combination thereof.

3. The method according to claim 1, wherein said human hepatocytes are exposed to at least one vitamin D, vitamin D precursor, vitamin D metabolite or vitamin D analog.

4. The method according to claim 3, wherein said at least one vitamin D is selected from the group consisting of cholecalciferol, calcifediol, calcitriol, and combinations thereof.

5. The method according to claim 1, wherein said human hepatocytes are exposed to at least one hypoxia inducing compound.

6. The method according to claim 1, wherein said human hepatocytes are exposed to at least one hypoxia inducing compound selected from the group consisting of RAR-related orphan receptor alpha (ROR-alpha) ligands, $CoCl_2$, and $NaN_3$.

7. The method according to claim 6, wherein said at least one RAR-related orphan receptor alpha (ROR-alpha) ligand is selected from the group consisting of CGP52608, a CGP52608 analog, melatonin, melatonin analogs, cholesterol, cholesterol derivatives, and combinations thereof.

8. The method according to claim 1, wherein said human hepatocytes are exposed to at least one sphingosine or sphingosine derivative.

9. The method according to claim 8, wherein said sphingosine is D-erythro-sphingosine.

10. The method according to claim 8, wherein said sphingosine derivative is sphingosine-1-phosphate or sphingolipid.

11. The method according to claim 10, wherein said sphingolipid is a ceramide or a ceramide analog.

12. The method according to claim 11, wherein said ceramide analog is L-erythro MAPP or D-erythro MAPP.

13. The method according to claim 1, wherein said human hepatocytes are exposed to at least one activator of peroxisome proliferator-activated receptors (PPARs).

14. The method according to claim 13, wherein said at least one activator of peroxisome proliferator-activated receptors (PPARs) is selected from the group consisting of thiazolidinediones, free fatty acids (FFAs), eicosanoids including eicosanoid precursors and eicosanoid analog, and combinations thereof.

15. The method according to claim 13, wherein said at least one activator of peroxisome proliferator-activated receptors is at least one unsaturated fatty acid selected from the group consisting of IOZ-heptadecenoic acid, arachidonic acid (AA), 9(Z),II(E)-Conjugated Linoleic Acid, eicosadienoic acid, eicosatrienoic acid (ETE), eicosapentaenoic acid (EPA), docosapentaenoic acid (DPA), docosahexaenoic acid (DHA), linoleic acid, gamma-linolenic acid, dihomo-gamma-linolenic acid, docosadiennoic acid, adrenic acid, mead acid, ricinoleic acid, docosatrienoic acid, and combinations thereof.

16. The method according to claim 15, wherein said at least one activator of peroxisome proliferator-activated receptors is at least one saturated fatty acid selected from the group consisting of dodecanoic acid, tridecanoic acid, tetradecanoic acid, pentadecanoic acid, hexadecanoic acid, heptadecanoic acid, eicosanoic acid, heneicosanoic acid, docosanoic acid, tricosanoic acid, tetracosanoic acid, pentacosanoic acid, hexacosanoic acid, and combinations thereof.

17. The method according to claim 16, wherein said at least one PKC inhibitor is selected from the group consisting of Bisindolylmaleimide I, Bisindolylmaleimide II, Bisindolylmaleimide III, Bisindolylmaleimide V, Bisindolylmaleimide VI, Bisindolylmaleimide VII, Bisindolylmaleimide VIII, Bisindolylmaleimide X, HBDDE, Rottlerin, Palmitoyl-DL-carnitine, R-Stearoyl Carnitine Chloride, Piceatannol, p-PKC δ antibody (H-9), N-[2-(methylamino)ethyl]-5-isoquinolinesulfonamide, dihydrochloride (H-8), 1-(5-Isoquinolinesulfonyl)-3-methylpiperazine, HA-100 dihydrochloride, N-(2-Guanidinoethyl)-5-isoquinolinesulfonamide (HA-1004), 1-(5-Isoquinolinylsulfonyl)homopiperazine (HA-1077), 5-Iodotubericidin, Ro-32-0432, Ro-31-7549, Enzastaurin (LY317615), Sotrastaurin, Dequalinium Chloride, Go 6976, Go 6983, Go 7874, Myricitrin, 4-Hydroxy-Tamoxifen,N-Desmethyltamoxifen HCl, Safingol, Phloretin, UCN-01, 7-Oxostaurosporine, K-252a, K-252b, K-252c, Melittin, Hispidin, Calphostin C, Ellagic acid, PKC Inhibitor Peptide 19-31, PKC Inhibitor Peptide 19-36, PKC epsilon Translocation Inhibitor II, EGF-R Fragment 651-658, PKC beta inhibitor (CAS 257879-35-9), PKC 20-28, PKCβII/EGFR Inhibitor (CAS 145915-60-2), PKCθ Pseudosubstrate Inhibitor, PKCθ/δ Inhibitor, [Ala107]-MBP (104-118), [Ala113]-MBP (104-118), zeta-Pseudosubstrate inhibitory peptide (ZIP), 1-(5-Isoquinolinesulfonyl)-3-methylpiperazine (C-1), Bryostatin 1, LY 333531 hydrochloride, CGP 53353, Chelerythrine Chloride, TCS 21311, CID 755673, Gossypol, ET-18-OCH3, 1-O-Hexadecyl-2-O-methyl-rac-glycerol, NPC-15437 dihydrochloride, NGIC-I, MDL-27,032, DAPH-7, 7-Aminoindole, 5-Amino-2-methylindole, rac-2-Methoxy-3-hexadecanamido-1-propylphosphocholine, Copper bis-3,5-diisopropylsalicylate, D,L-3,4-Dihydroxymandelic Acid, rac-3-Octadecanamido-2-Methoxypropan-1-ol Phosphocholine, KRIBB3, Ilmofosine, rac-2-Methoxy-3-hexadecanamido-1-propylphosphocholine, and combinations thereof.

18. The method according to claim 15, wherein said at least one activator of peroxisome proliferator-activated receptors is at least one eicosanoid, eicosanoid precursor or eicosanoid analog.

19. The method according to claim 15, wherein said at least one activator of peroxisome proliferator-activated receptors is at least an eicosanoid, eicosanoid precursor or eicosanoid analog selected from the group consisting of Diacylglycerol, Eicosapentaenoic acid, Dihomo-gamma-linolenic acid, Arachidonic acid, ETYA (5,8,11,14-eicosatetraynoic acid), members of the hydroxyeicosatetraenoic acid (HETE) family, including 5-HETE and 15-HETE, members of the hydroxyoctadecadieonic acid (HODE) family, including 9-HODE and 13-HODE, classic eicosanoids, and non-classic eicosanoids.

20. The method according to claim 1, wherein said human hepatocytes are exposed to at least one platelet-activating factor (PAF).

21. The method according to claim 1, wherein said human hepatocytes are exposed to at least one protein kinase C (PKC) inhibitor.

\* \* \* \* \*